(12) United States Patent
Kim et al.

(10) Patent No.: US 9,799,835 B2
(45) Date of Patent: *Oct. 24, 2017

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Hyeryeong Kim, Cheonan-si (KR); Sunhee Lee, Cheonan-si (KR); Wonsam Kim, Cheonan-si (KR); Jaewan Jang, Cheonan-si (KR); Yuri Kim, Wonju-si (KR); Junghwan Park, Seoul (KR); Seongje Park, Busan (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 128 days.

This patent is subject to a terminal disclaimer.

(21) Appl. No.: 14/775,803

(22) PCT Filed: Mar. 7, 2014

(86) PCT No.: PCT/KR2014/001864
§ 371 (c)(1),
(2) Date: Sep. 14, 2015

(87) PCT Pub. No.: WO2014/142472
PCT Pub. Date: Sep. 18, 2014

(65) Prior Publication Data
US 2016/0020410 A1    Jan. 21, 2016

(30) Foreign Application Priority Data
Mar. 15, 2013 (KR) .................. 10-2013-0027621

(51) Int. Cl.
*H01L 51/50* (2006.01)
*H01L 51/00* (2006.01)
(Continued)

(52) U.S. Cl.
CPC ........ *H01L 51/0072* (2013.01); *C07D 471/04* (2013.01); *C07D 487/04* (2013.01);
(Continued)

(58) Field of Classification Search
None
See application file for complete search history.

(56) References Cited

U.S. PATENT DOCUMENTS

2005/0110005 A1* 5/2005 Forrest ............... H01L 51/0504
257/40
2008/0207917 A1   8/2008 Li et al.
2012/0268786 A1* 10/2012 Noguchi .............. G03G 15/50
358/1.15

FOREIGN PATENT DOCUMENTS

CN    104245690 A    12/2014
CN    104736542 A     6/2015
(Continued)

OTHER PUBLICATIONS

The First Office Action dated May 4, 2016 for CN Application No. 201480015670.9, with English Translation.
(Continued)

*Primary Examiner* — Gregory Clark
(74) *Attorney, Agent, or Firm* — Vorys, Sater, Seymour & Pease LLP; Mih Suhn Koh

(57) ABSTRACT

The present invention provides a novel compound capable of improving light emitting efficiency, stability, and lifespan of the element, an organic electric element using the same, and an electronic device for the same.

8 Claims, 1 Drawing Sheet

(51) Int. Cl.
   *C07D 487/04* (2006.01)
   *C09K 11/06* (2006.01)
   *C07D 471/04* (2006.01)
   *C07D 491/048* (2006.01)

(52) U.S. Cl.
   CPC ......... *C07D 491/048* (2013.01); *C09K 11/06* (2013.01); *H01L 51/0059* (2013.01); *H01L 51/0067* (2013.01); *H01L 51/0071* (2013.01); *H01L 51/0073* (2013.01); *H01L 51/0074* (2013.01); *C09K 2211/1007* (2013.01); *C09K 2211/1011* (2013.01); *C09K 2211/1029* (2013.01); *C09K 2211/1033* (2013.01); *C09K 2211/1044* (2013.01); *C09K 2211/1059* (2013.01); *C09K 2211/1088* (2013.01); *C09K 2211/1092* (2013.01); *H01L 51/0052* (2013.01); *H01L 51/0061* (2013.01); *H01L 51/5012* (2013.01); *H01L 51/5016* (2013.01); *Y02E 10/549* (2013.01)

(56) References Cited

FOREIGN PATENT DOCUMENTS

| | | | |
|---|---|---|---|
| EP | 0 906 947 A1 | 4/1999 | |
| KR | 10-2011-0007233 A | 1/2011 | |
| WO | WO 2013/154325 | * 10/2013 | ............. C09K 11/06 |
| WO | 2014/061546 A1 | 4/2014 | |

OTHER PUBLICATIONS

Japanese Office Action for Japanese application No. 2015-562905, one page, dated Sep. 15, 2016.

Hu, Nan-Xing et al., "Novel high TG hole-transport molecules based on indolo[3,2-b]carbazoles for organic light-emitting devices", Synthetic Metals, vol. 111-112, pp. 421-424, (2000).

* cited by examiner

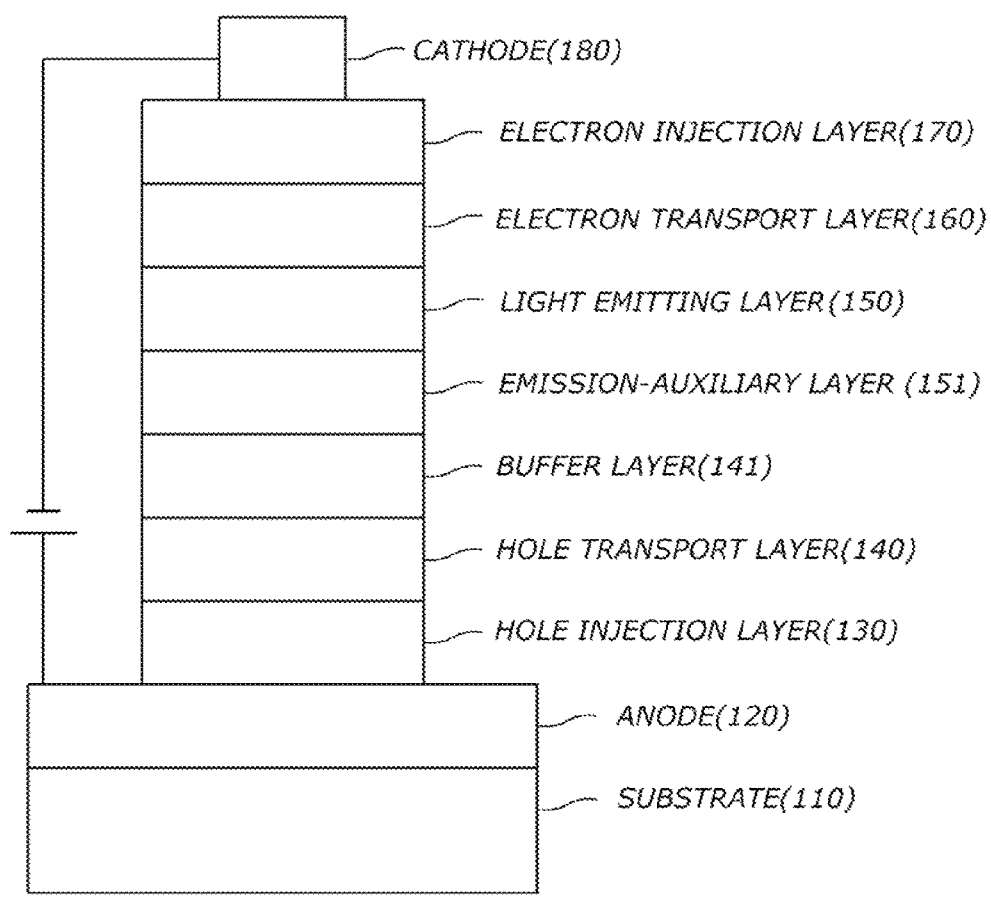

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application claims priority from and the benefit under 35 U.S.C. §119(a) of Korean Patent Application No. 10-2013-0027621, filed on Mar. 15, 2013, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed.

Accordingly, there is a continuous need to develop new materials for an organic material layer.

SUMMARY

In order to solve one or more of the above-mentioned problems in prior art, an aspect of the present invention is to provide a compound which allows an organic electric element to have high luminous efficiency, low driving voltage and high heat-resistant and to be improved in color purity and life span, an organic electric element using the same, and an electronic device including the organic electric element.

In accordance with an aspect of the present invention, a compound represented by the following formula is provided:

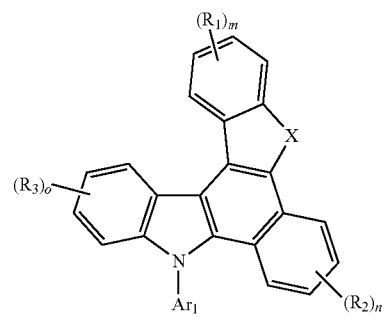

In another aspect of the present invention, an organic electric element comprising the compound represented by the formula above and an electronic device comprising the organic electric element are provided.

By using the compound according to embodiments of the present invention, an organic electric element according to one or more embodiments of the present invention not only has high luminous efficiency, low driving voltage and high heat-resistant and, but can also be significantly improved in color purity, and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine, chlorine, bromine, or iodine.

Unless otherwise stated, the term "alkyl" or "alkyl group" as used herein has, but not limited to, a single bond of 1 to 60 carbon atoms.

Unless otherwise stated, the term "alkenyl" or "alkynyl" as used herein has, but not limited to, double or triple bonds of 2 to 60 carbon atoms.

Unless otherwise stated, the term "cycloalkyl" as used herein means, but not limited to, alkyl forming a ring having 3 to 60 carbon atoms.

Unless otherwise stated, the term "alkoxyl group" as used herein has, but not limited to, 1 to 60 carbon atoms.

Unless otherwise stated, the term "aryl group" or "arylene group" as used herein has, but not limited to, 6 to 60 carbon atoms.

Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, a spirofluorene group, or a spirobifluorene group.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, includes both monocyclic and polycyclic rings, and may also be formed in conjunction with an adjacent group.

Unless otherwise stated, the term "heterocycloalkyl", "heterocyclic group" as used herein contains one or more heteroatoms, but not limited to, has 2 to 60 carbon atoms, includes both monocyclic and polycyclic rings, and may be formed in conjunction with an adjacent group. Also, the heterocyclic group may mean alicyclic and/or aromatic group containing heteroatoms.

Unless otherwise stated, the term "heteroatom" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "saturated or unsaturated ring" means a saturated or unsaturated aliphatic ring or an aromatic ring having 6 to 60 carbon atoms or a hetero ring.

Hetero compounds other than the above-mentioned hetero compounds or hetero radicals each contain, but not limited to, one or more heteroatoms.

Unless otherwise stated, the term "substituted or unsubstituted" as used herein means that substitution is substituted by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer formed on at least one of the sides the first and second electrodes, which is a side opposite to the organic material layer.

The inventive compound employed in the organic material layer may be used as materials of the hole injection layer 130, the hole transport layer 140, the electron transport layer 160, the electron injection layer 170, a host material or a dopant material of the light emitting layer 150, or a capping layer material.

The organic electric element according to an embodiment of the present invention may be manufactured using a PVD (physical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

Further, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below:

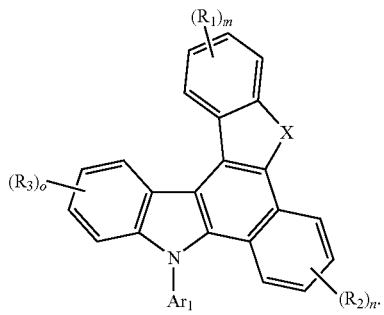

[Formula 1]

In Formula 1 above, m, n and o may be each an integer from 1 to 4.

$R_1$ to $R_3$ may be independently selected from the group consisting of hydrogen, deuterium, tritium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a fluorenyl group, and -$L_1$—$N(Ar_2)(Ar_3)$.

Also, any two adjacent groups of $R_1$ to $R_3$ may be optionally linked together to form a fused ring. Here, when $R_1$ to $R_3$ don't form a fused ring, $R_1$ to $R_3$ may respectively be as defined in Formula 1. For example, when both of m and n is 2, $R_1$ may form a fused ring together with adjacent group, and $R_2$ may independently be an aryl group or a heterocyclic group, though it has an adjacent group.

Of course, when m is an integer of 2 or more, plural $R_1$ may be the same or different, and any two adjacent groups are optionally linked together to form a ring, and other groups don't formed a ring may be selected from the substituted group defined above. When n or O is an integer of 2 or more, the same means as defined in above.

Meanwhile, a ring formed between any two adjacent groups may be a $C_3$-$C_{60}$ aliphatic ring, a $C_6$-$C_{60}$ aromatic ring, a $C_2$-$C_{60}$ heterocyclic ring or fused ring formed by combination of each of them, and not only mono or poly cyclic ring but also saturated or unsaturated ring.

X is $NR_4$ or O (oxygen), herein, $R_4$ may be selected from the group consisting of a $C_6$-$C_{60}$ aryl group, a $C_2$-$C_{60}$ heterocyclic group containing at least one heteroatom selected from the group consisting of O, N, S, Si, and P, $C_1$-$C_{50}$ alkyl group, a fluorenyl group, and -$L_1$—$N(Ar_2)(Ar_3)$.

$Ar_1$ may be selected from the group consisting of a $C_6$-$C_{60}$ aryl group, a $C_2$-$C_{60}$ heterocyclic group containing at least one heteroatom selected from the group consisting of O, N, S, Si, and P, $C_1$-$C_{50}$ alkyl group, a fluorenyl group, and -$L_1$—$N(Ar_2)(Ar_3)$.

Herein, $Ar_2$ and $Ar_3$ may be independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, and a fluorenyl group.

$L_1$ may be selected from the group consisting of a single bond, a $C_6$-$C_{60}$ arylene group, a $C_2$-$C_{60}$ heteroarylene group containing at least one heteroatom selected from O, N, S, Si, and P, a fluorenylene group, and also, the arylene group, heteroarylene group, fluorenylene group may be respectively substituted by one or more substituents selected from the group consisting of a nitro group, a cyano group, a halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group and an amino group.

Also, the compound represented by Formula 1 above may be represented by one of Formulas below:

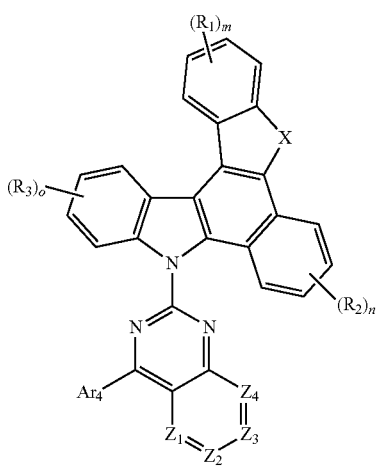

[Formula 2]

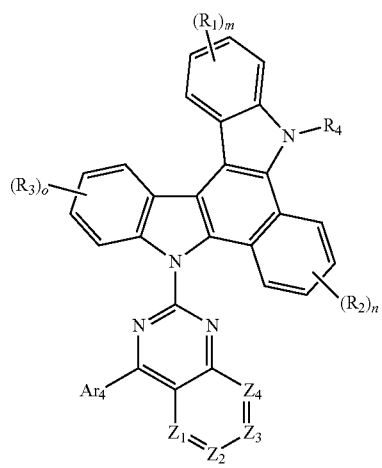

[Formula 3]

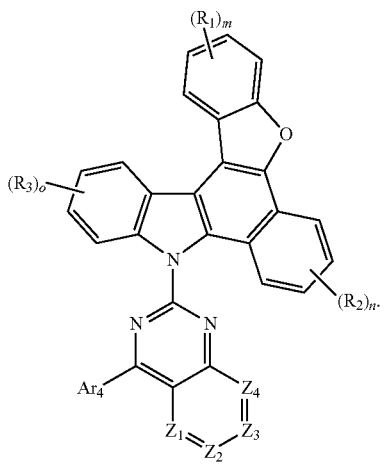

[Formula 4]

In Formulas 2 to 4, $R_1$ to $R_4$, X, m, n and o may be as defined in Formula 1.

$Ar_4$ may be selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, and a fluorenyl group.

Also, $Z_1$ to $Z_4$ may be independently $CR_5$ or N, herein, $R_5$ may be selected from the group consisting of hydrogen, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, and a fluorenyl group.

The aryl group, fluorenyl group, heterocyclic group and alkyl group may be respectively substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Here, in the case of an aryl group above, the aryl group may have 6 to 60 carbon atoms, preferably, 6 to 30 carbon atoms and more preferably, 6 to 20 carbon atoms, in the case of an heterocyclic group above, the heterocyclic group may have 2 to 60, preferably, 2 to 30 and more preferably, 2 to 20, in the case of an arylene group above, the arylene group may have 6 to 60 carbon atoms, preferably, 6 to 30 carbon atoms and more preferably, 6 to 20 carbon atoms, in the case of an alkyl group above, the alkyl group may have 1 to 50 carbon atoms, preferably, 1 to 30 carbon atoms, more preferably, 1 to 20 carbon atoms, much more preferably, 1 to 10 carbon atoms.

Specifically, the compound represented by Formulae 1 above may be represented by one of the compounds below.

1-1

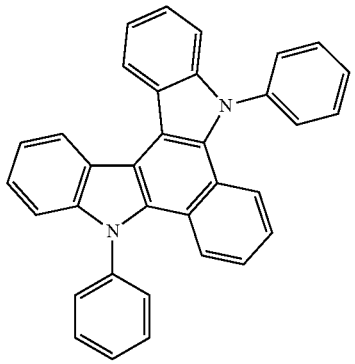

1-2

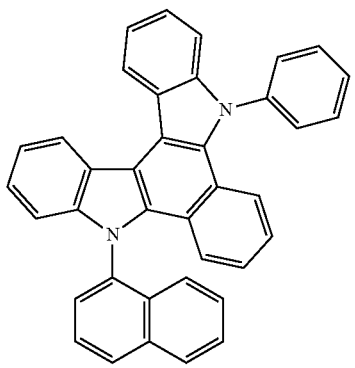

1-3

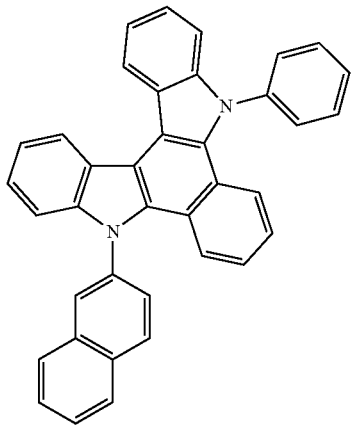

1-4

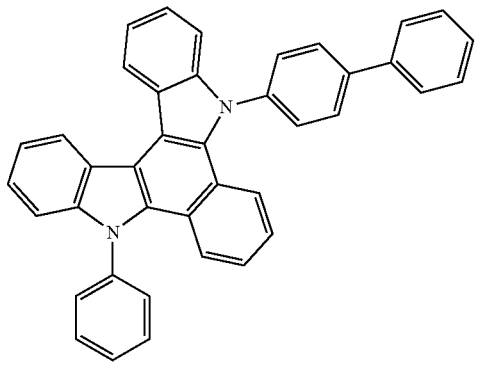

1-5

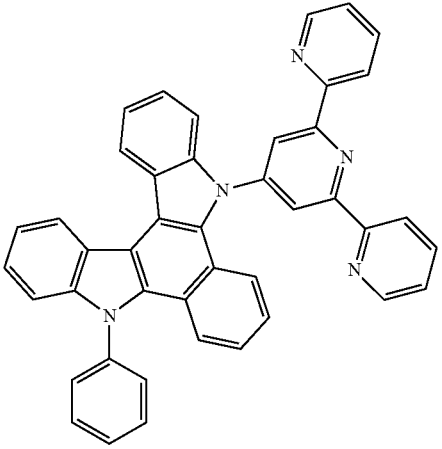

1-6
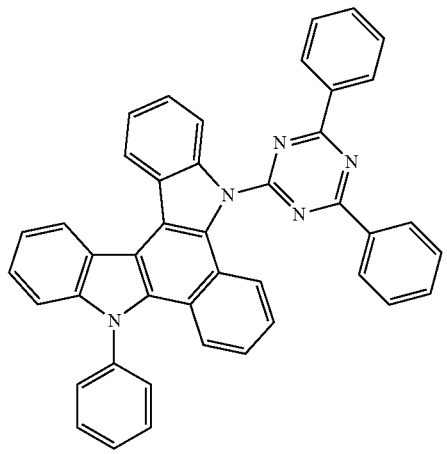
1-7
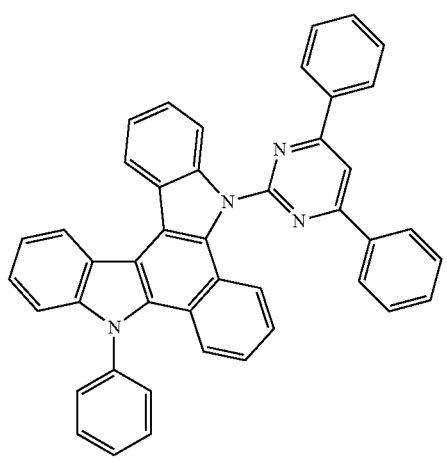
1-8
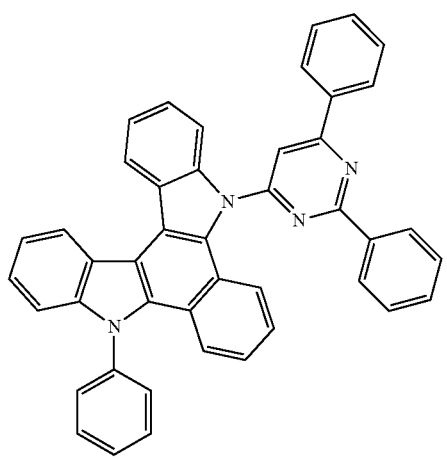
1-9
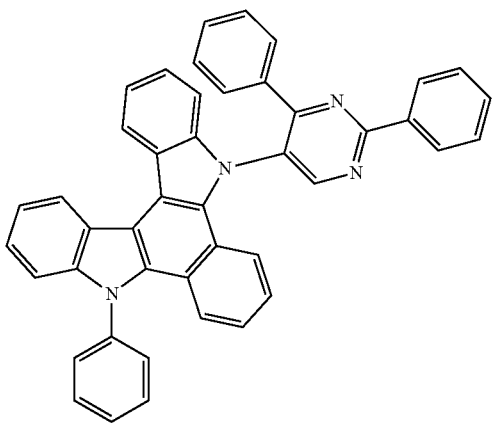
1-10
1-11
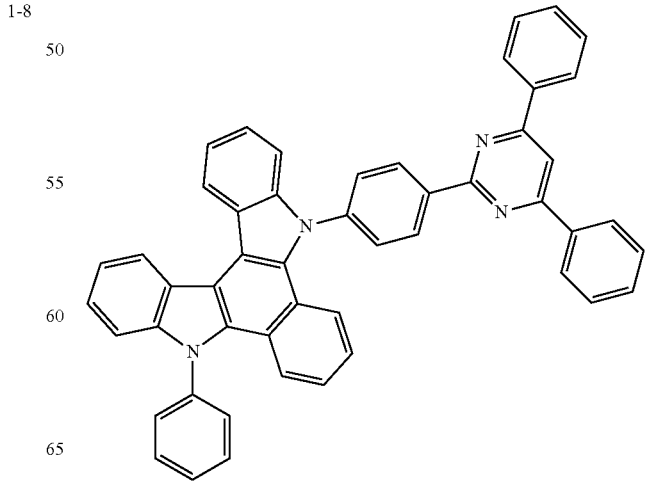

1-12
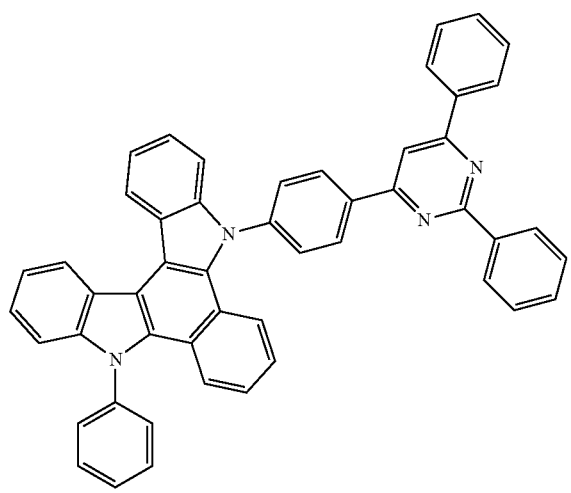
1-13
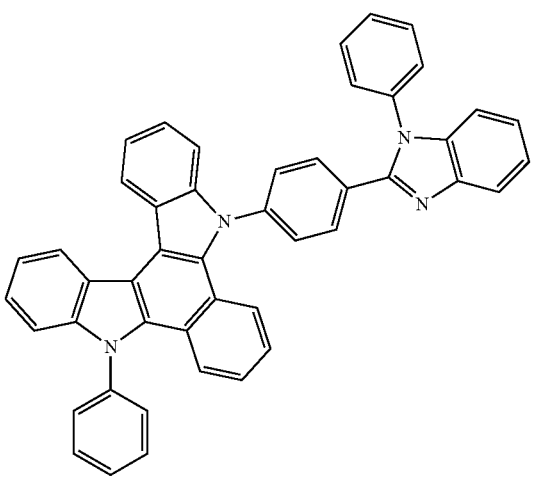
1-14
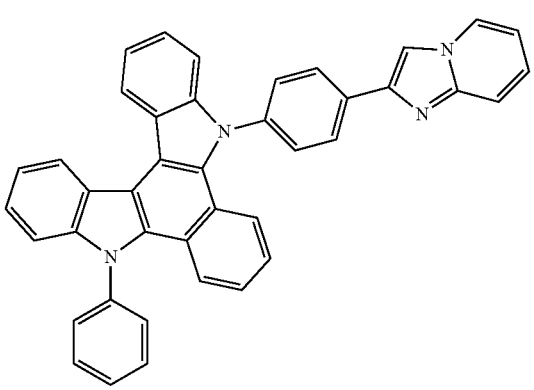
1-15
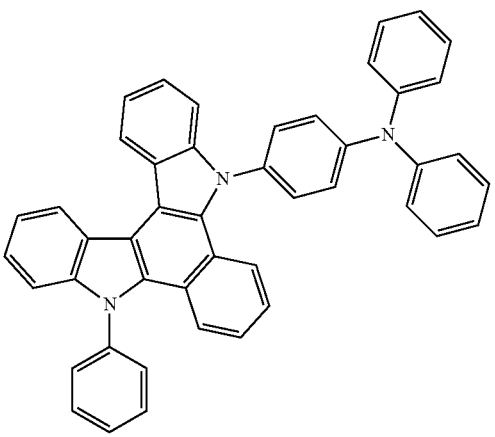
1-16
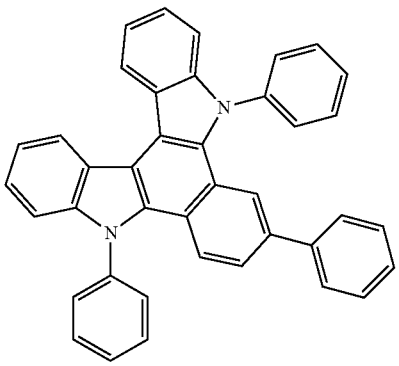
1-17
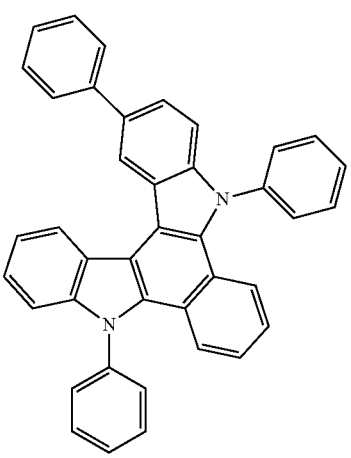

1-18
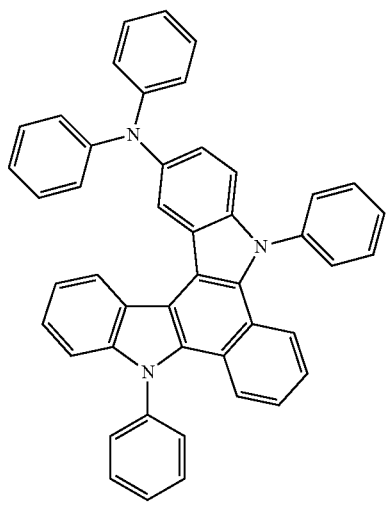
1-19
1-20
1-21
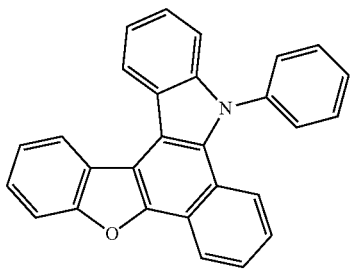
1-22
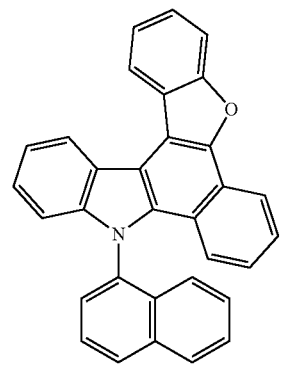
1-23
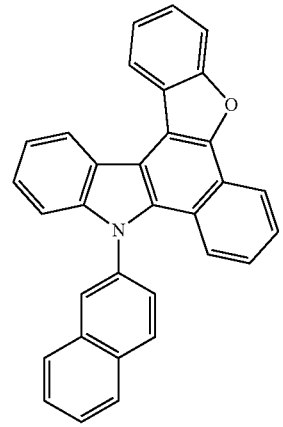
1-24
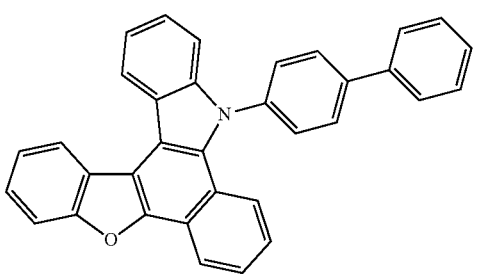

1-25
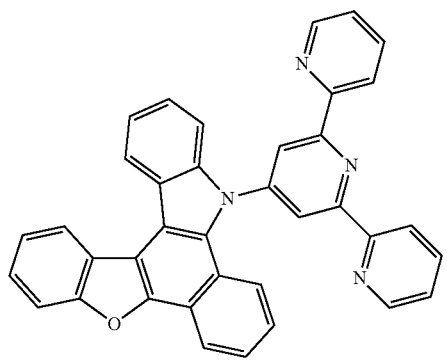
1-26
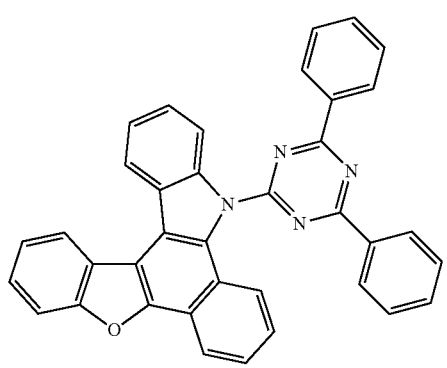
1-27
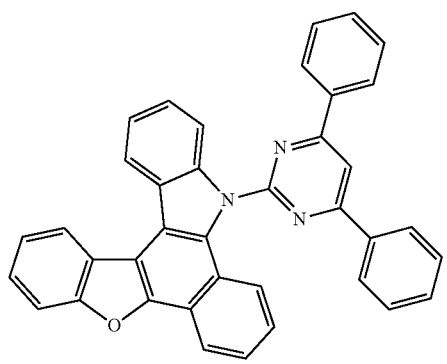
1-28
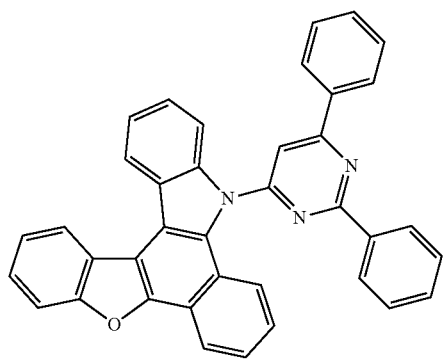
1-29
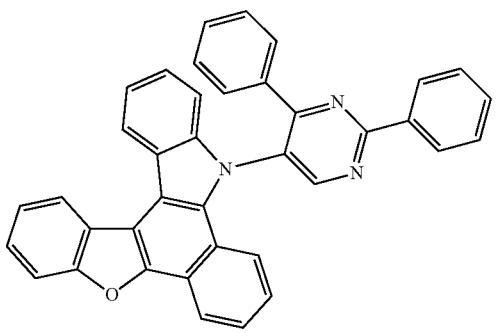
1-30
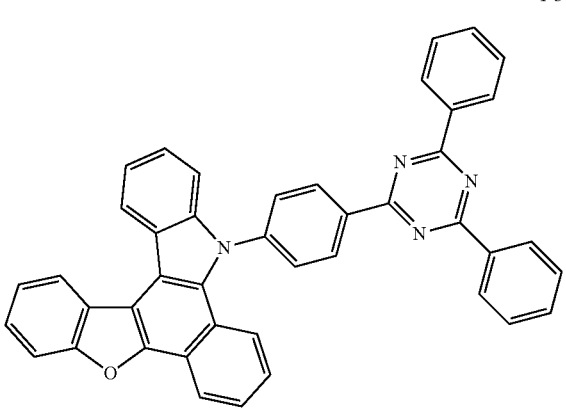
1-31
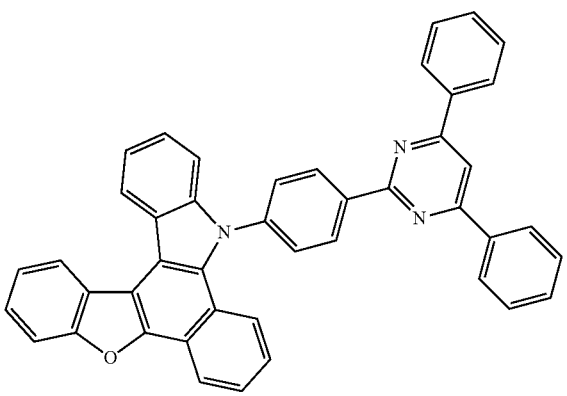
1-32
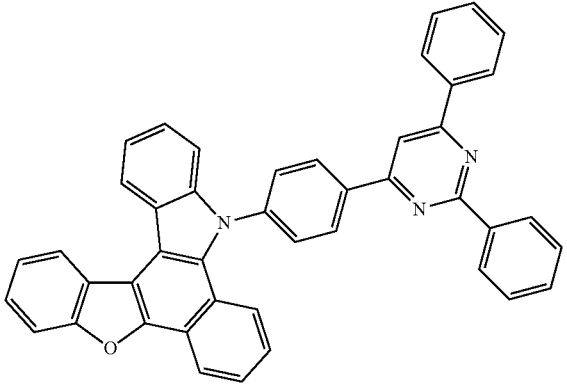

-continued
1-33
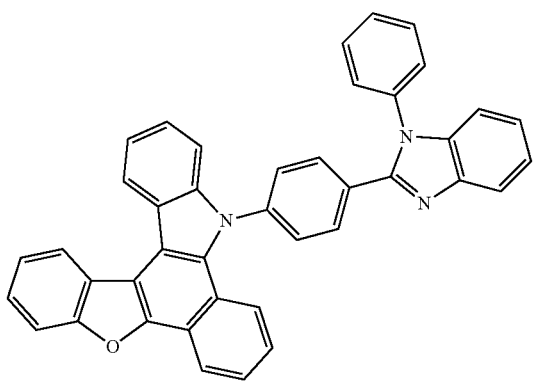
1-34
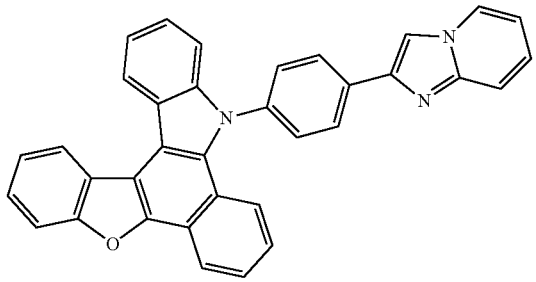
1-35
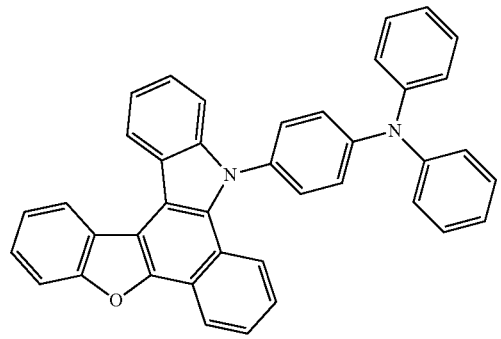
1-36
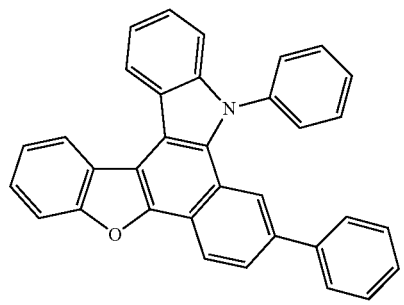
-continued
1-37
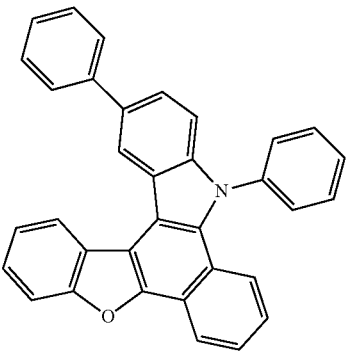
1-38
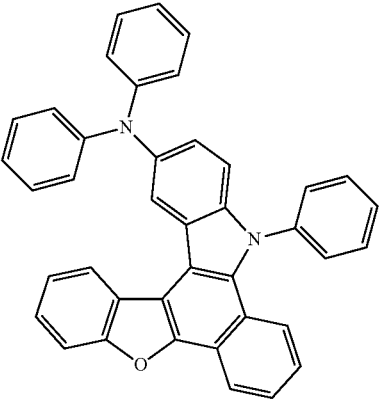
1-39
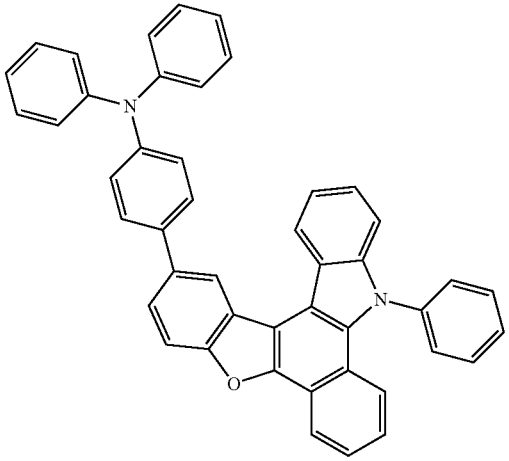
1-40
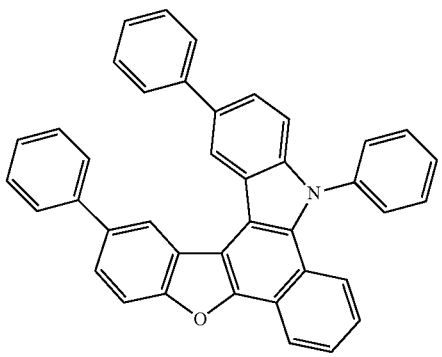

2-1
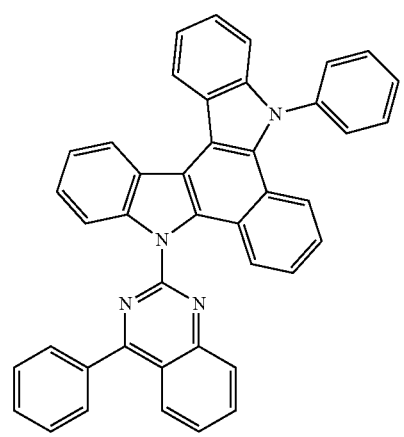
2-2
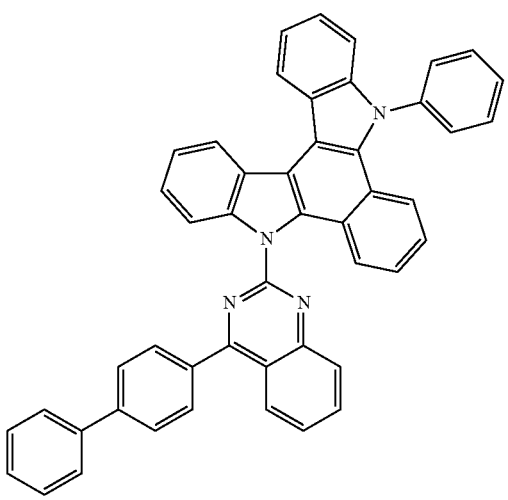
2-3
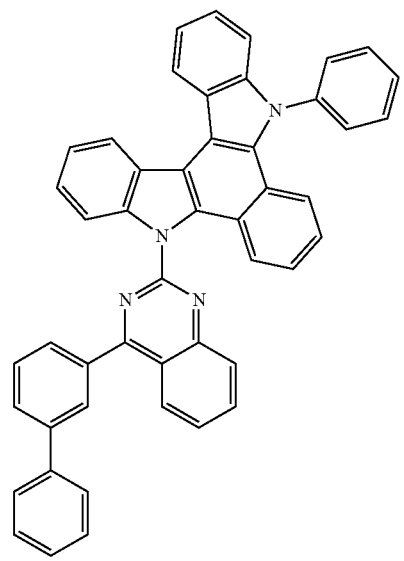
2-4
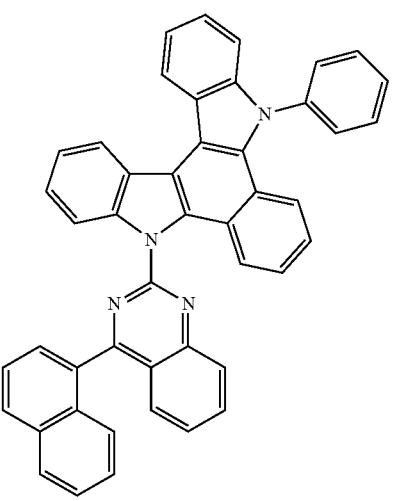
2-5
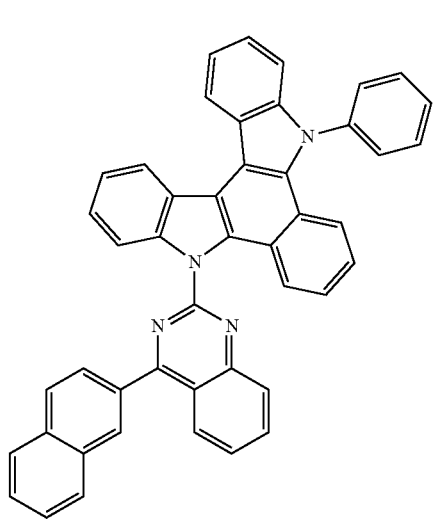
2-6
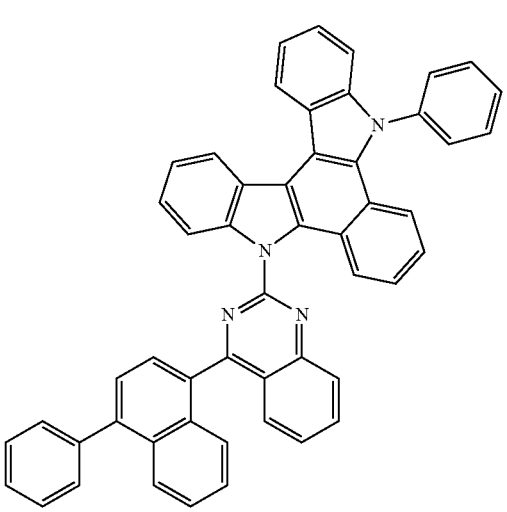

-continued
2-7
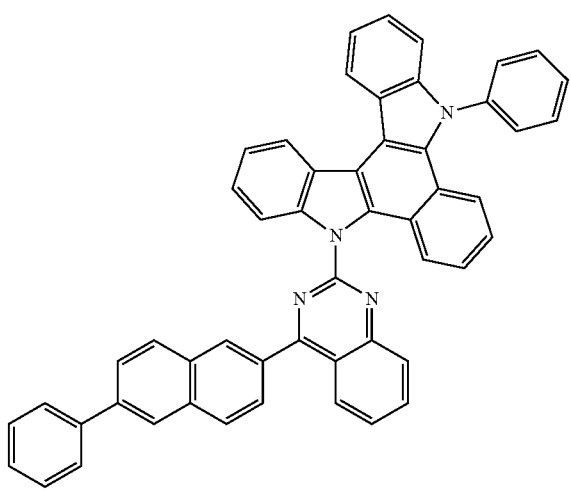
2-8
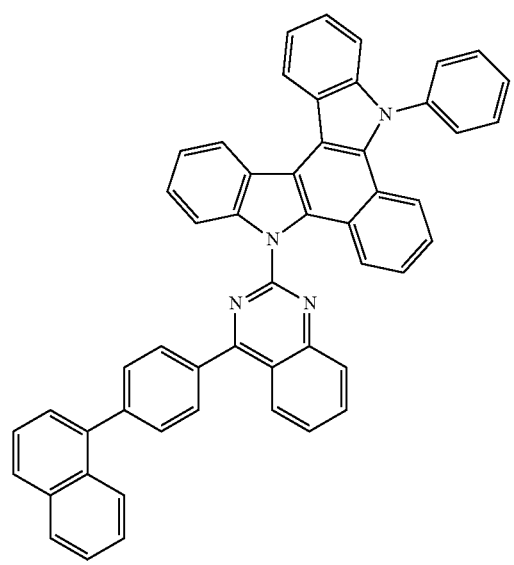
2-9
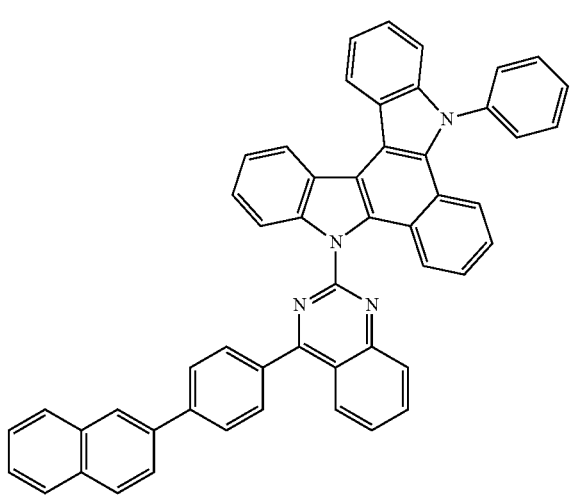
-continued
2-10
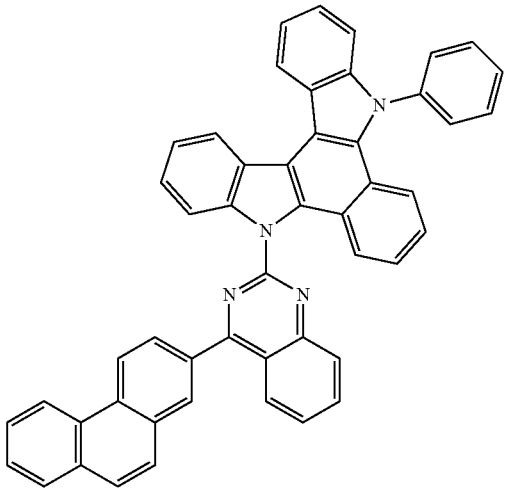
2-11
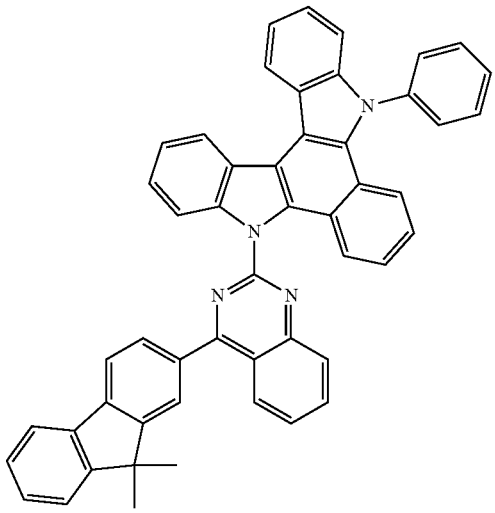
2-12
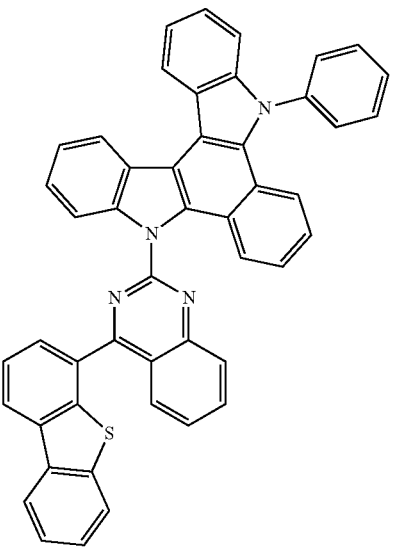

-continued
2-13
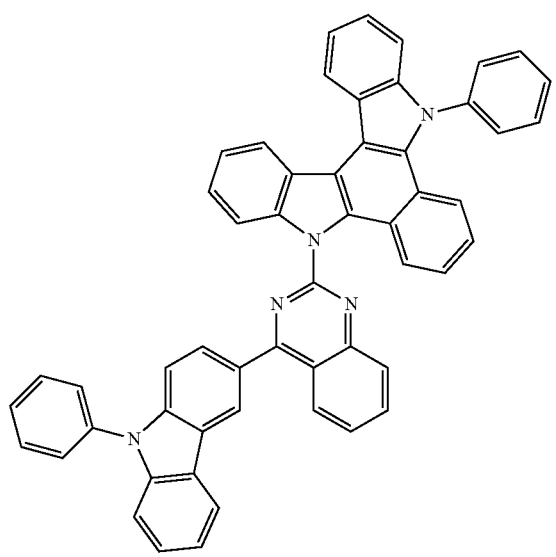
2-14
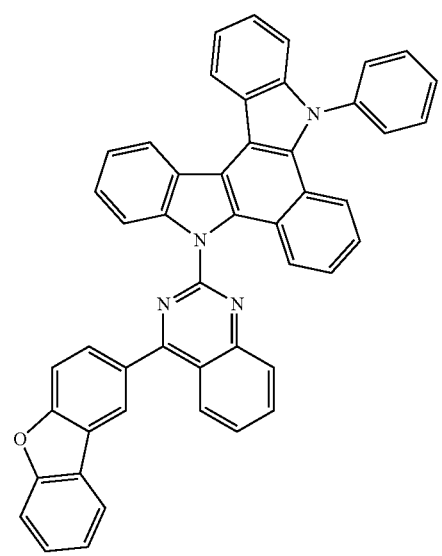
2-16
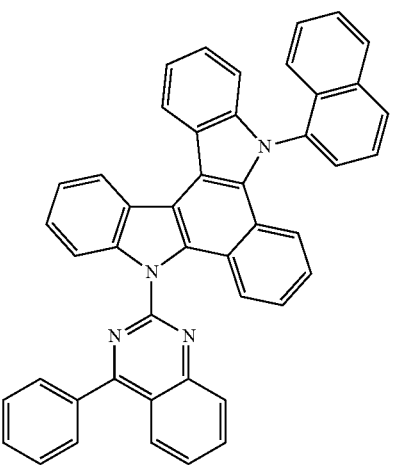
2-17
2-15
2-18
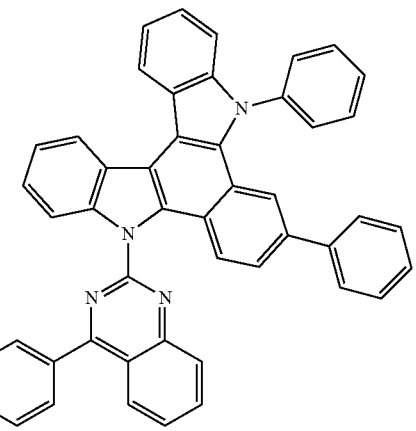

2-19
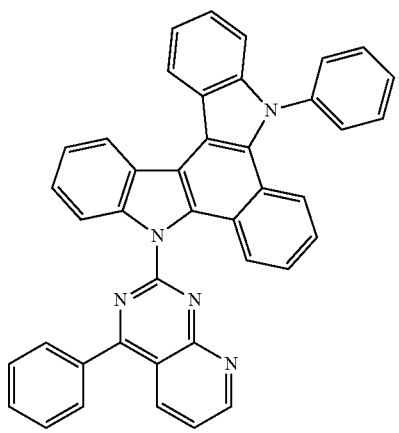
2-20
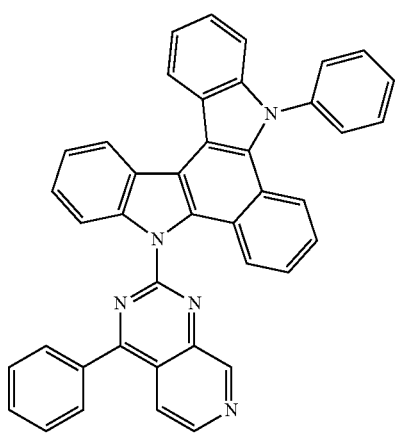
2-21
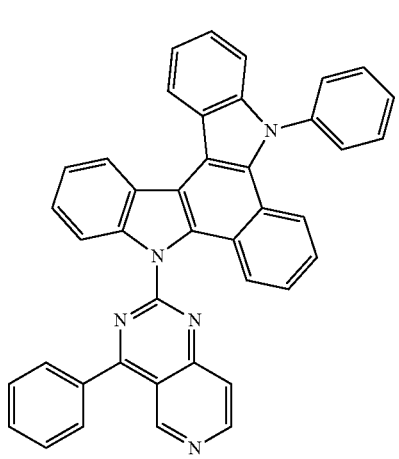
2-22
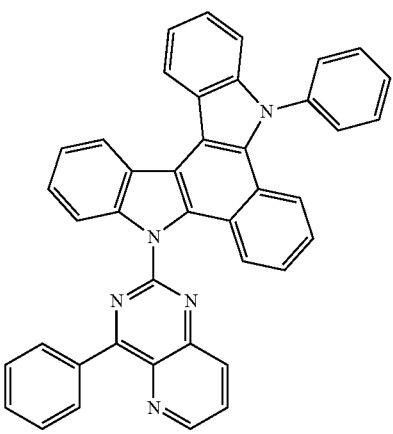
2-23
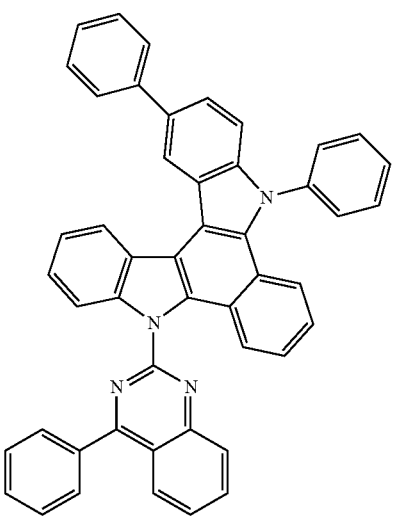
2-24
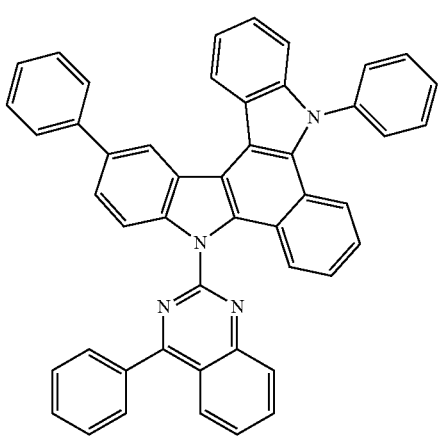

2-25
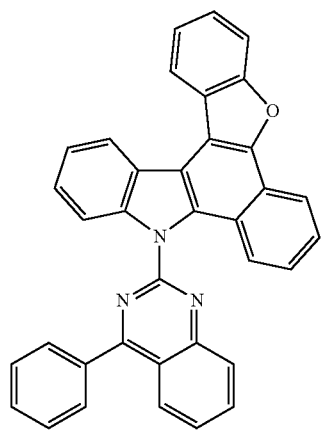
2-26
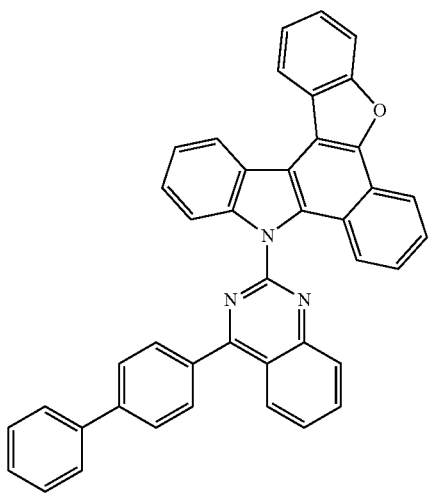
2-27
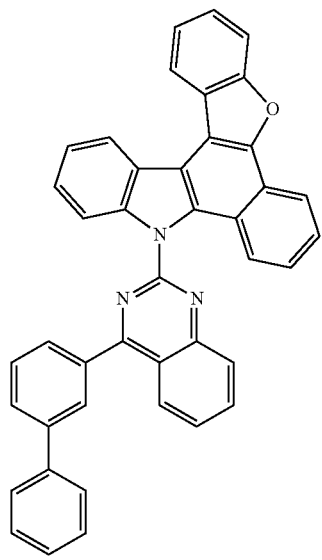
2-28
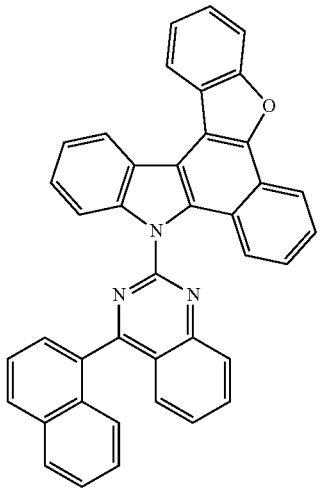
2-29
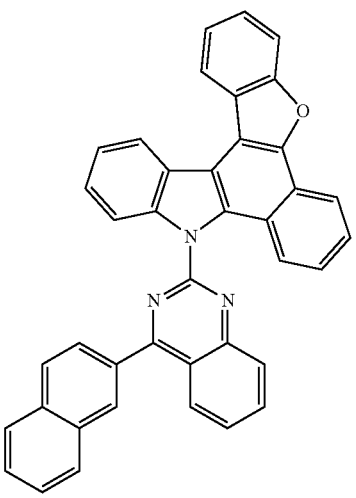
2-30
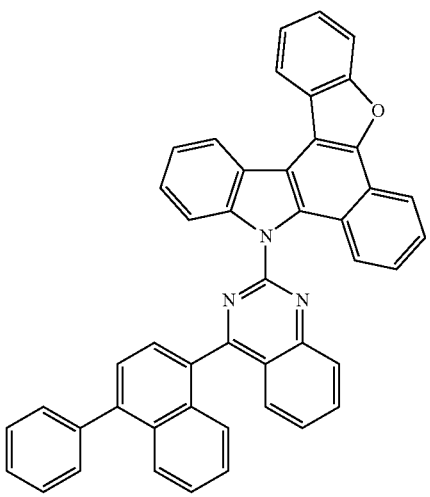

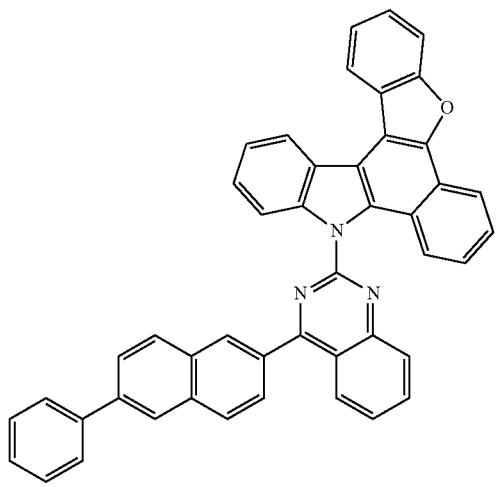 2-31
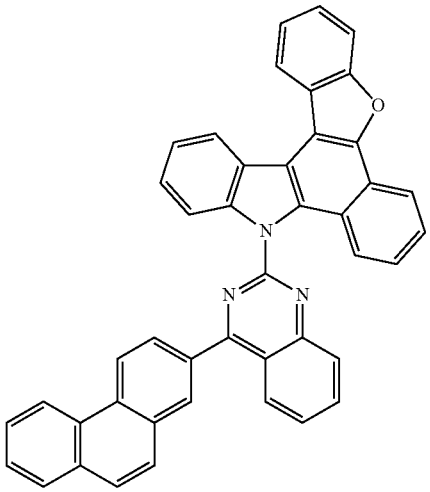 2-34
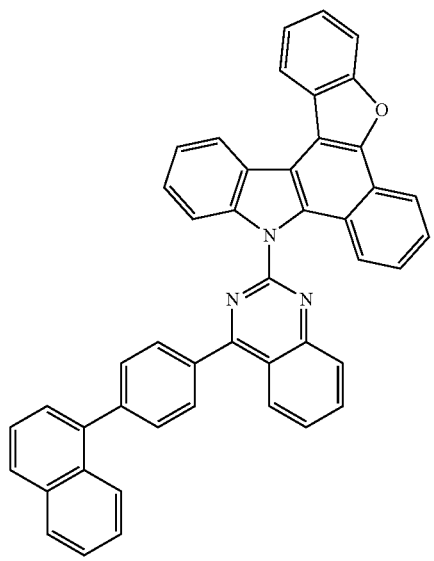 2-32
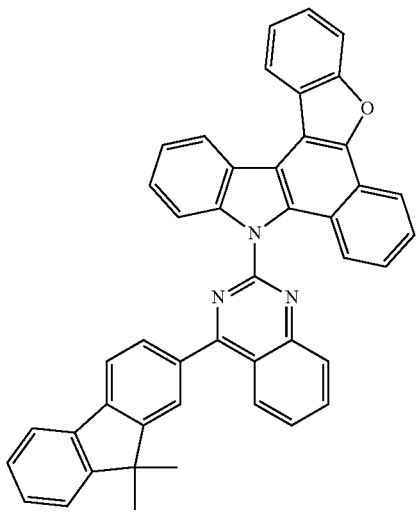 2-35
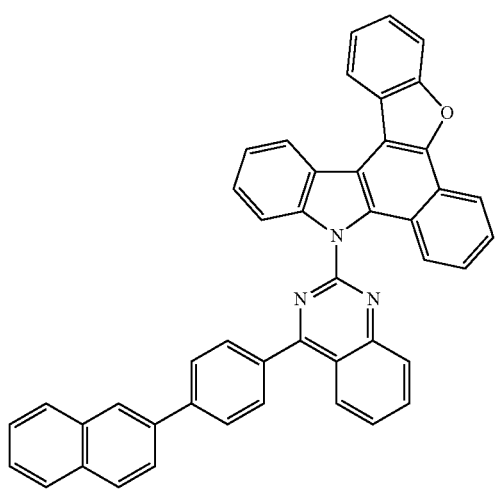 2-33
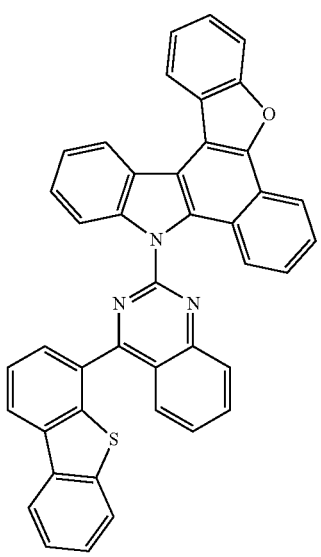 2-36

2-37
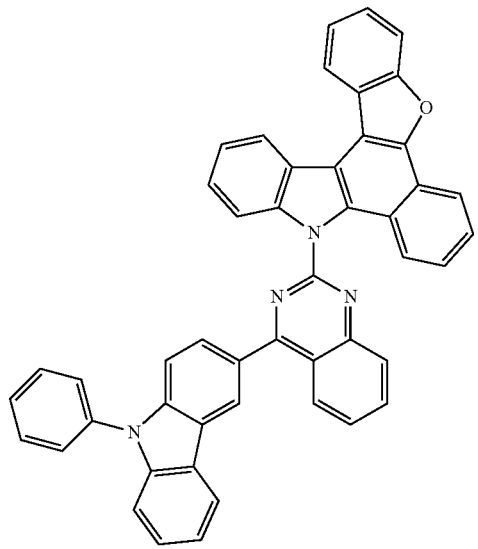
2-38
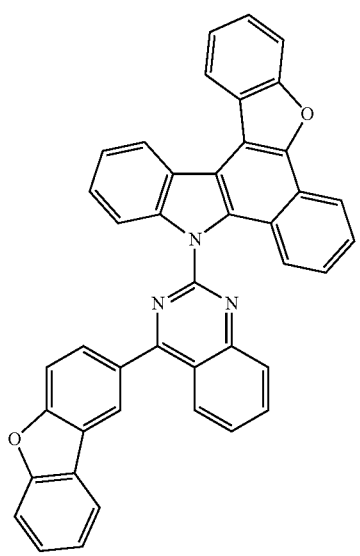
2-39
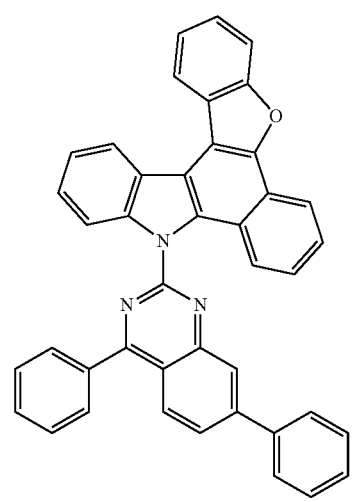
2-40
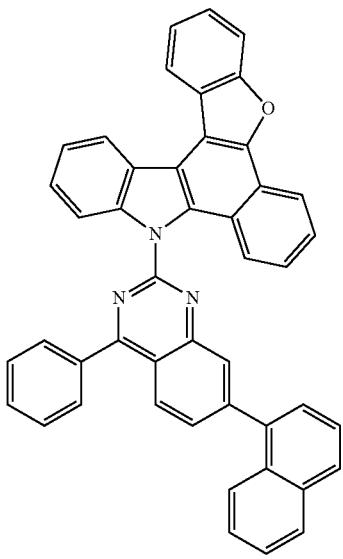
2-41
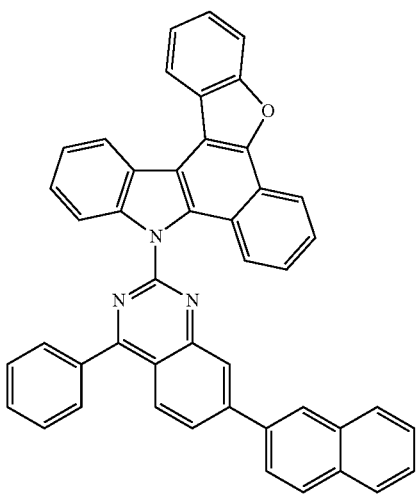
2-42

2-43
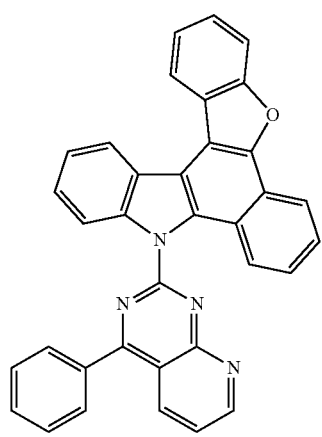
2-44
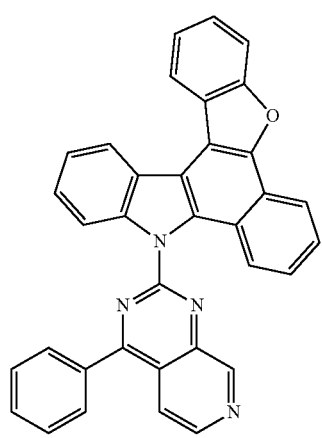
2-45
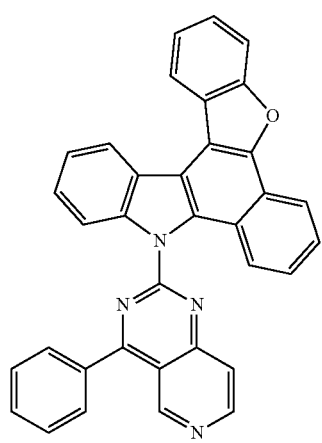
2-46
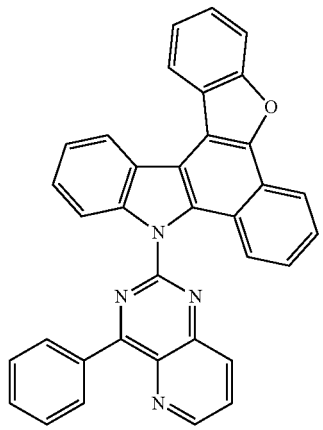
2-47
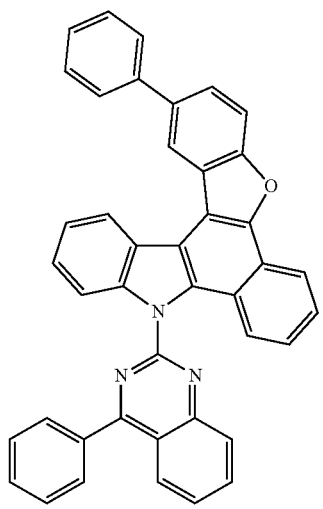
2-48
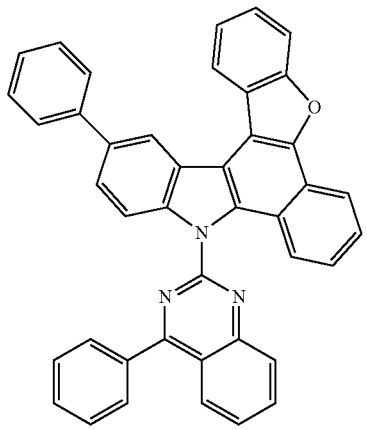
Hereinafter, Synthesis Examples of the inventive compound represented by Formula 1 according to the present invention and Preparation Examples of an organic electric element will be described in detail by way of example. However, the following examples are only for illustrative purposes and are not intended to limit the scope of the invention.

SYNTHESIS EXAMPLE

The final products according to the present invention can be synthesized by reaction between Sub 1 and Sub 2 as illustrated in, but not limited to, the following Reaction Scheme 1.

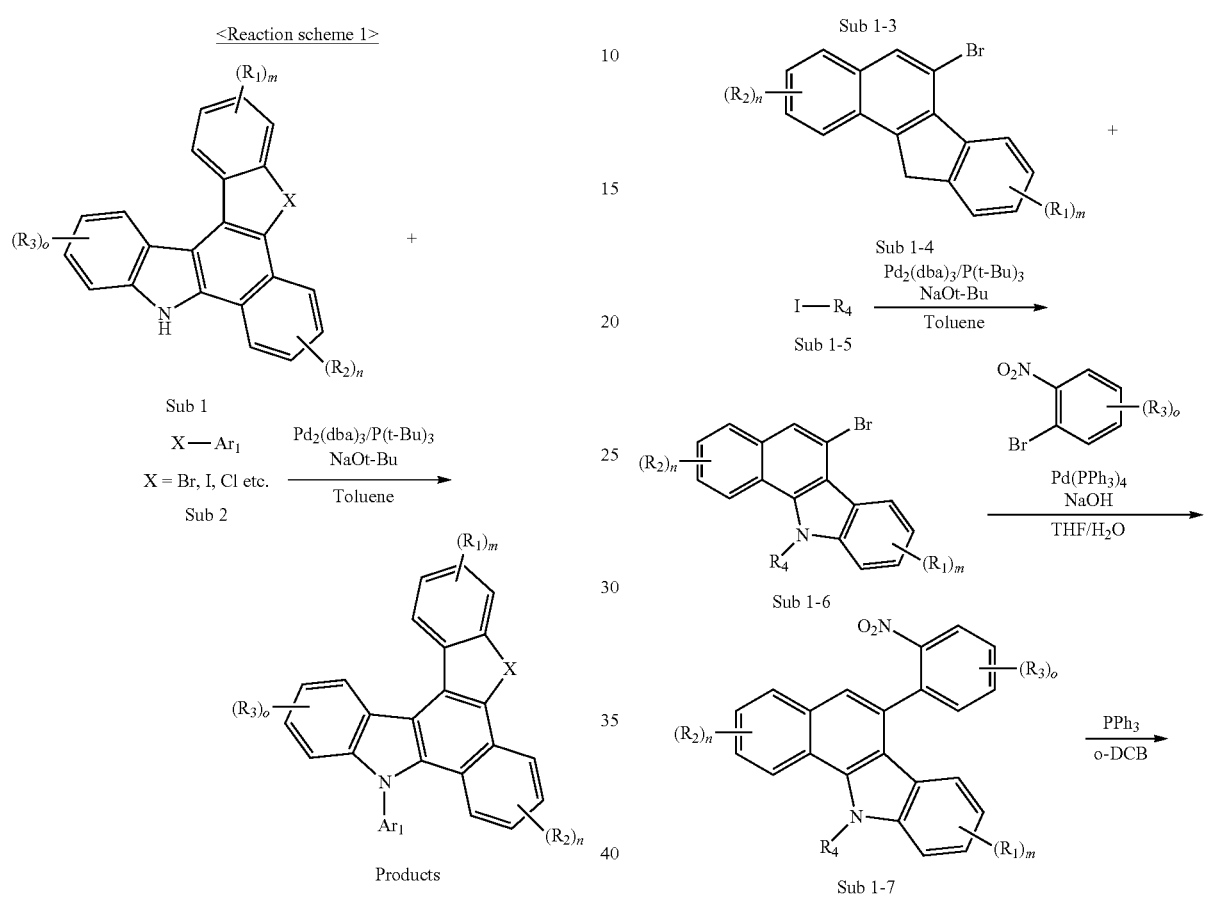

1. Synthesis Method of Sub 1

Sub 1 of the Reaction Scheme 1 can be synthesized according to, but not limited to, the following Reaction Scheme 2 and 3.

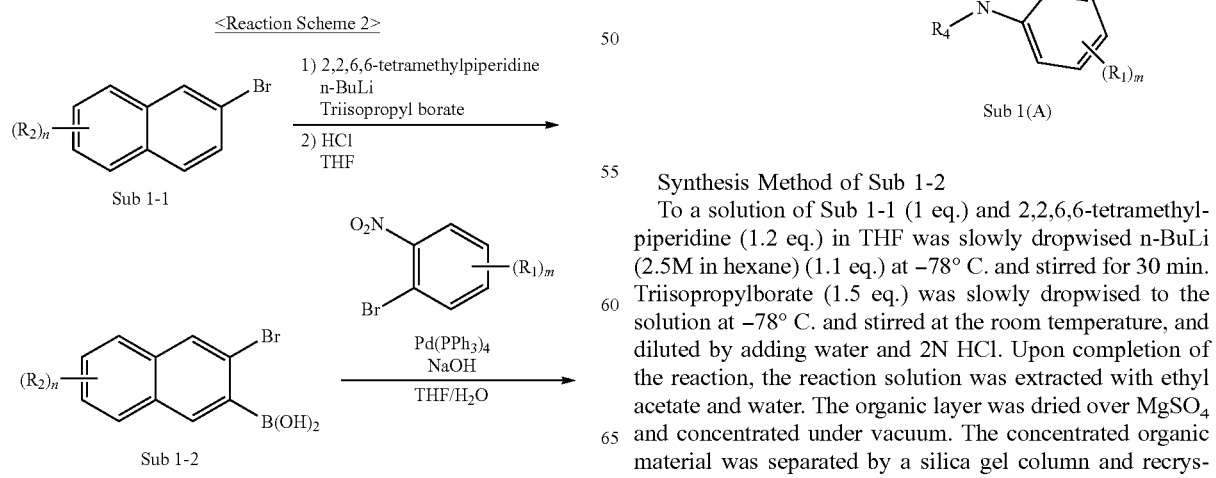

Synthesis Method of Sub 1-2

To a solution of Sub 1-1 (1 eq.) and 2,2,6,6-tetramethylpiperidine (1.2 eq.) in THF was slowly dropwised n-BuLi (2.5M in hexane) (1.1 eq.) at −78° C. and stirred for 30 min. Triisopropylborate (1.5 eq.) was slowly dropwised to the solution at −78° C. and stirred at the room temperature, and diluted by adding water and 2N HCl. Upon completion of the reaction, the reaction solution was extracted with ethyl acetate and water. The organic layer was dried over $MgSO_4$ and concentrated under vacuum. The concentrated organic material was separated by a silica gel column and recrystallization to obtain Sub 1-2.

Synthesis Method of Sub 1-3

A solution of Sub 1-2 (1 eq.), bromine compound (1 eq.), Pd(PPh₃)₄ (0.03 eq.) and NaOH (3 eq.) in anhydrous THF and trace amount of water was refluxed for 24 hour. Upon completion of the reaction, the reaction solution was cooled down to the room temperature and extracted with methylene chloride. The organic layer was washed with water, dried over MgSO₄, and then filtered and concentrated under vacuum. The concentrated organic material was separated by a silica gel column and recrystallization to obtain Sub 1-3.

Synthesis Method of Sub 1-4

A solution of Sub 1-3 and triphenylphosphine in o-dichlorobenzene was refluxed for 24 hour. Upon completion of the reaction, the solvent was removed by vacuum distillation and the concentrated organic material was separated by a silica gel column to obtain Sub 1-4.

Synthesis Method of Sub 1-6

A mixture of Sub 1-4 (1 eq.), Sub 1-5 (1.1 eq.), Pd₂(dba)₃ (0.3 eq.), 50% P(t-Bu)₃ (9 eq.) and NaOt-Bu (3 eq.) in a round bottom flask was stirred at 40° C. Upon completion of the reaction, the reaction solution was extracted with methylene chloride and water. The organic layer was dried over MgSO₄ and concentrated under vacuum, and then the produced organic material was separated by a silica gel column and recrystallization to obtain Sub 1-6.

Synthesis Method of Sub 1-7

A solution of Sub 1-6 (1 eq.), bromine compound (1 eq.), Pd(PPh₃)₄ (0.03 eq.) and NaOH (3 eq.) in anhydrous THF and trace amount of water was refluxed for 24 hour. Upon completion of the reaction, the reaction solution was cooled to the room temperature and extracted with methylene chloride. The organic layer was washed with water, dried over MgSO₄, and then, filtered and concentrated under vacuum. The produced organic material was separated by a silica gel column and recrystallization to obtain Sub 1-7.

Synthesis Method of Sub 1(A)

A solution of Sub 1-7 and triphenylphosphine in o-dichlorobenzene was refluxed for 24 hour. Upon completion of the reaction, the solvent was removed by vacuum distillation and the concentrated organic material was separated by a silica gel column to obtain Sub 1(A).

<Reaction Scheme 3>

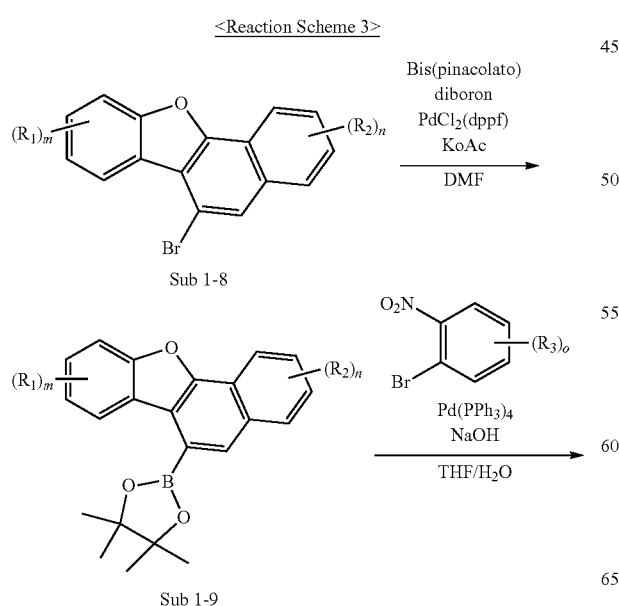

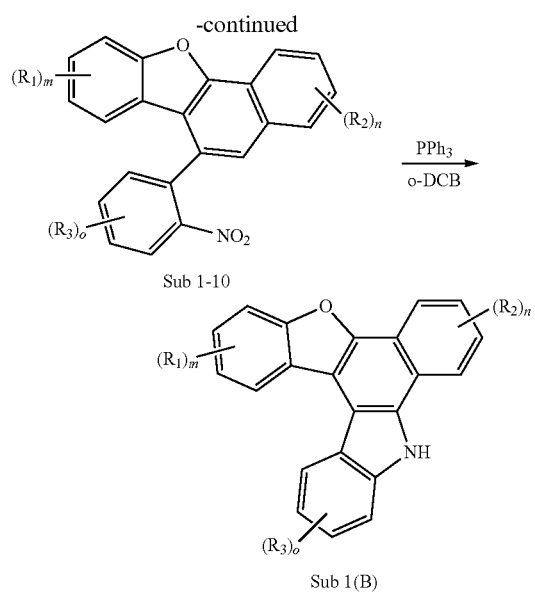

Synthesis Method of Sub 1-9

To a solution of Sub 1-8 (1 eq.) in DMF in a round bottom flask was added Bis(pinacolato)diboron (1.1 eq.), Pd(dppf)Cl₂ (0.03 eq.), KOAc (3 eq.) and stirred at 90° C. Upon completion of the reaction, DMF was removed by vacuum distillation and extracted with methylene chloride and water. The organic layer was dried over MgSO₄ and concentrated under vacuum, and then the produced organic material was separated by a silica gel column and recrystallization to obtain Sub 1-9.

Synthesis Method of Sub 1-10

A solution of Sub 1-9 (1 eq.), bromine compound (1 eq.), Pd(PPh₃)₄ (0.03 eq.) and K₂CO₃ (3 eq.) in anhydrous THF and trace amount of water was refluxed for 24 hour. Upon completion of the reaction, the reaction solution was cooled to the room temperature and extracted with methylene chloride. The organic layer was washed with water, dried over MgSO₄, filtered and concentrated under vacuum, and then the produced organic material was separated by a silica gel column to obtain Sub 1-10.

Synthesis Method of Sub 1(B)

A solution of Sub 1-10 and triphenylphosphine in o-dichlorobenzene was refluxed for 24 hour. Upon completion of the reaction, the solvent was removed by vacuum distillation and then the concentrated organic material was separated by a by a silica gel column to obtain Sub 1(B).

Meanwhile, examples of Sub 1 compounds include, but are not limited to, the following compounds, and FD-MS data of the compounds are given in Table 1 below.

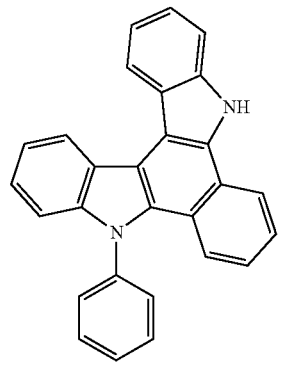

Sub 1(1)

-continued
Sub 1(2)
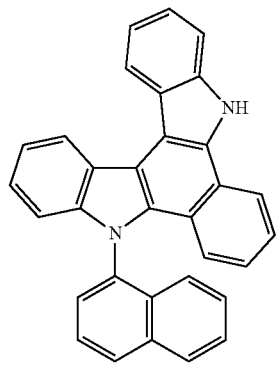
Sub 1(3)
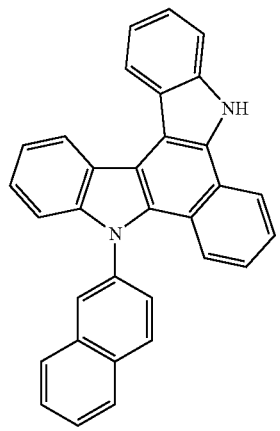
Sub 1(4)
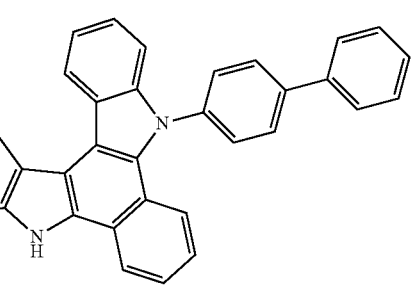
Sub 1(5)
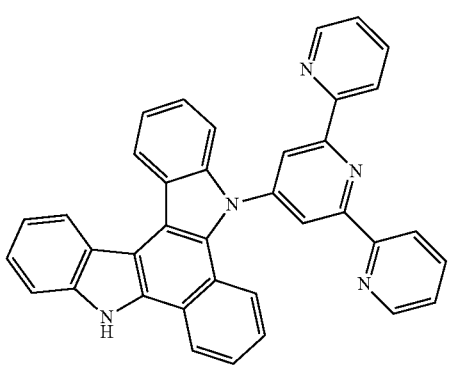
-continued
Sub 1(6)
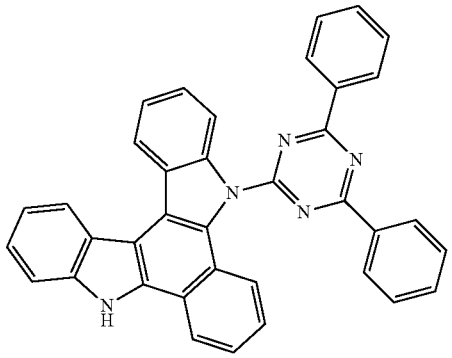
Sub 1(7)
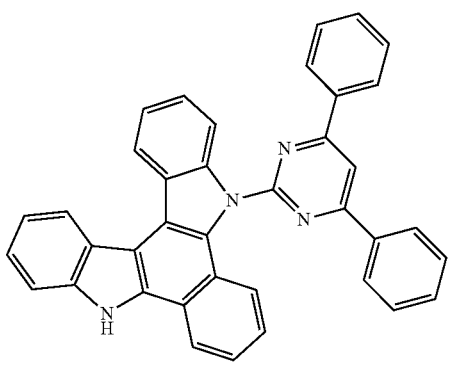
Sub 1(8)
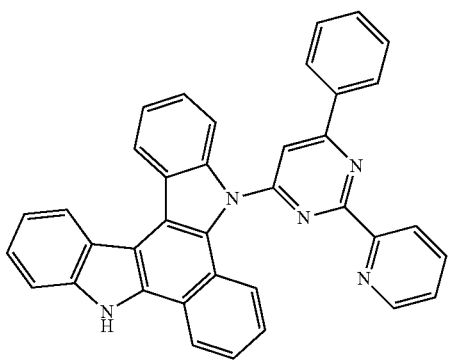
Sub 1(9)
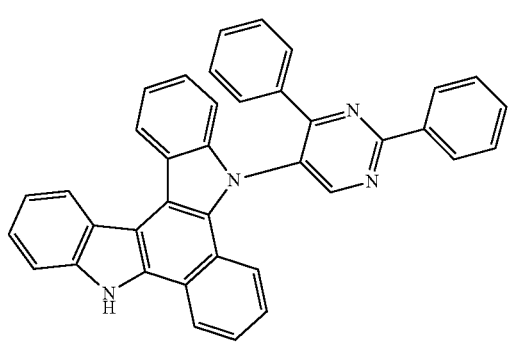

-continued
Sub 1(10)
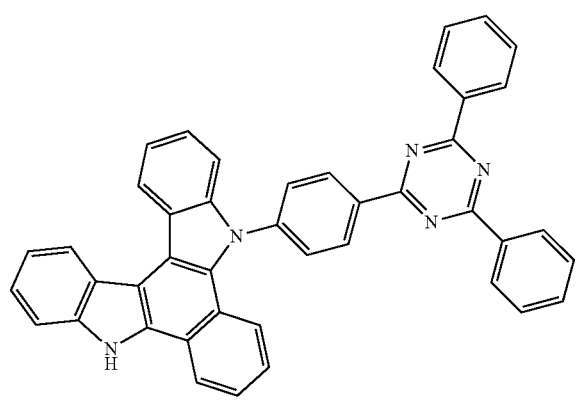
Sub 1(14)
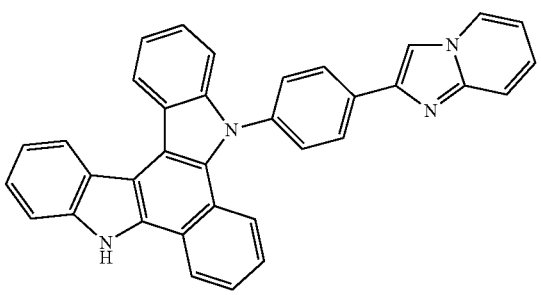
Sub 1(11)
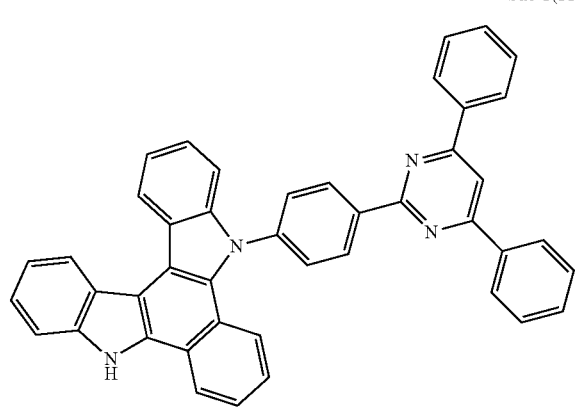
Sub 1(15)
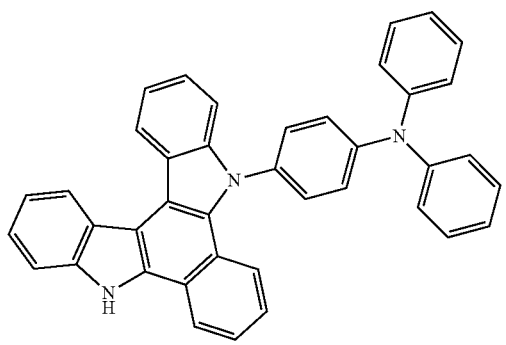
Sub 1(12)
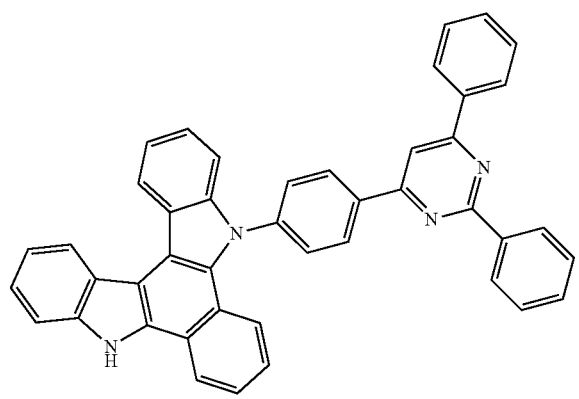
Sub 1(16)
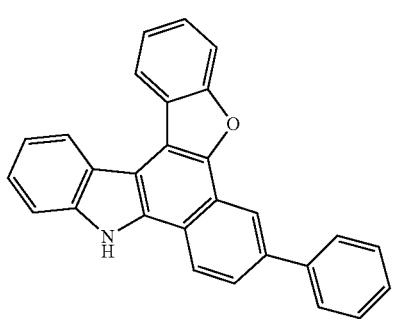
Sub 1(13)
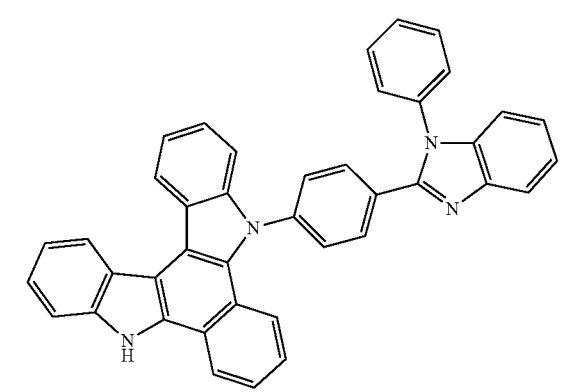
Sub 1(17)
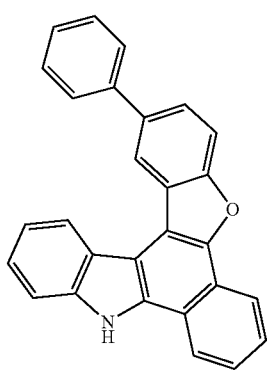

-continued

Sub 1(18)

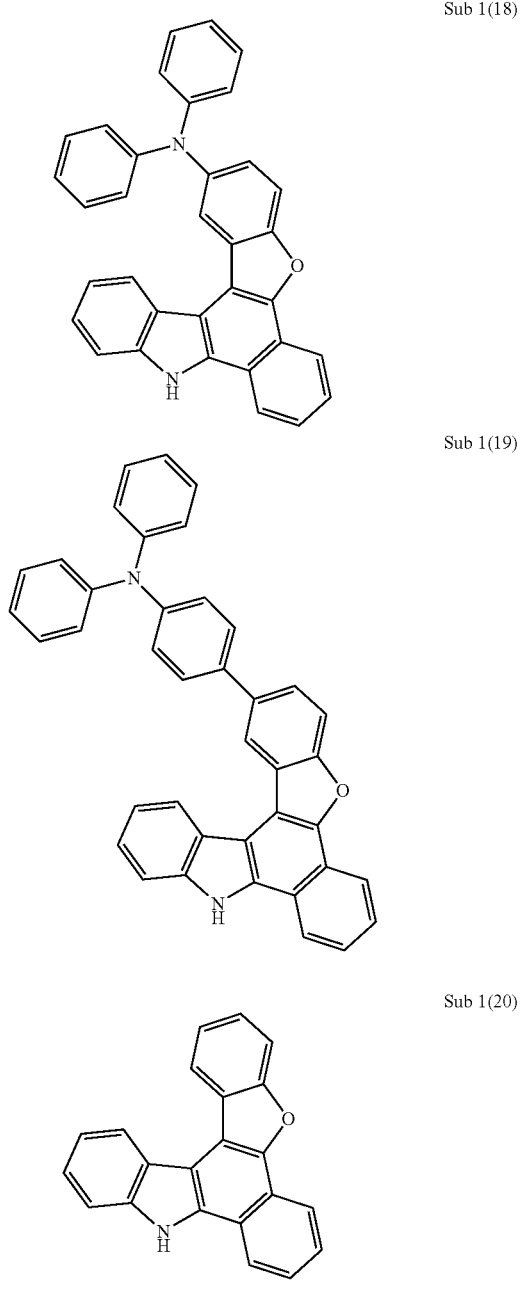

Sub 1(19)

Sub 1(20)

2. Examples of Sub 2

Examples of Sub 2 compounds include, but are not limited to, the following compounds, and FD-MS data of the compounds are given in Table 2 below.

Sub 2-1
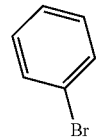

Sub 2-2
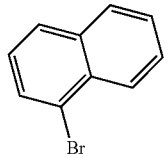

Sub 2-3
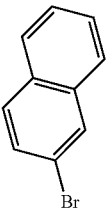

Sub 2-4
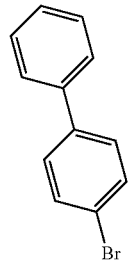

Sub 2-5
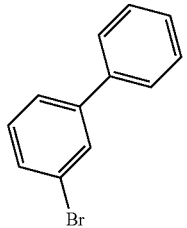

TABLE 1

| Compound | FD-MS | Compound | FD-MS |
|---|---|---|---|
| Sub 1 (1) | m/z = 382.15 ($C_{28}H_{18}N_2$ = 382.46) | Sub 1 (2) | m/z = 432.16 ($C_{32}H_{20}N_2$ = 432.51) |
| Sub 1 (3) | m/z = 432.16 ($C_{32}H_{20}N_2$ = 432.51) | Sub 1 (4) | m/z = 458.18 ($C_{34}H_{22}N_2$ = 458.55) |
| Sub 1 (5) | m/z = 537.20 ($C_{37}H_{23}N_5$ = 537.61) | Sub 1 (6) | m/z = 537.20 ($C_{37}H_{23}N_5$ = 537.61) |
| Sub 1 (7) | m/z = 536.20 ($C_{38}H_{24}N_4$ = 536.62) | Sub 1 (8) | m/z = 536.20 ($C_{38}H_{24}N_4$ = 536.62) |
| Sub 1 (9) | m/z = 536.20 ($C_{38}H_{24}N_4$ = 536.62) | Sub 1 (10) | m/z = 613.23 ($C_{43}H_{27}N_5$ = 613.71) |
| Sub 1 (11) | m/z = 612.23 ($C_{44}H_{28}N_4$ = 612.72) | Sub 1 (12) | m/z = 612.23 ($C_{44}H_{28}N_4$ = 612.72) |
| Sub 1 (13) | m/z = 574.22 ($C_{41}H_{26}N_4$ = 574.67) | Sub 1 (14) | m/z = 498.18 ($C_{35}H_{22}N_4$ = 498.58) |
| Sub 1 (15) | m/z = 549.22 ($C_{40}H_{27}N_3$ = 549.66) | Sub 1 (16) | m/z = 383.13 ($C_{28}H_{17}NO$ = 383.44) |
| Sub 1 (17) | m/z = 383.13 ($C_{28}H_{17}NO$ = 383.44) | Sub 1 (18) | m/z = 474.17 ($C_{34}H_{22}N_2O$ = 474.55) |
| Sub 1 (19) | m/z = 550.20 ($C_{40}H_{26}N_2O$ = 550.65) | Sub 1 (20) | m/z = 307.10 ($C_{22}H_{13}NO$ = 307.34) |

Sub 2-6
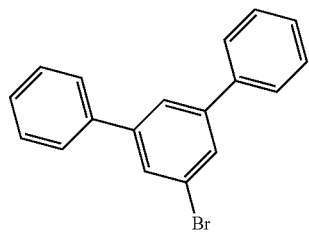
Sub 2-7
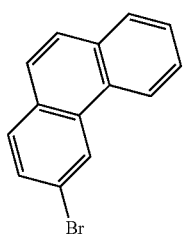
Sub 2-8
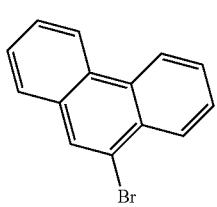
Sub 2-9
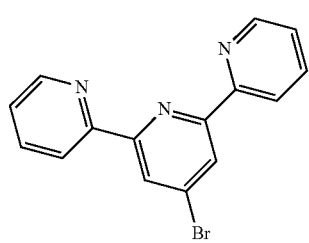
Sub 2-10
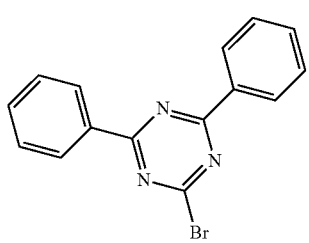
Sub 2-11
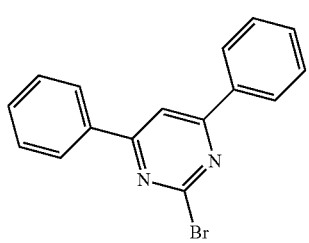
Sub 2-12
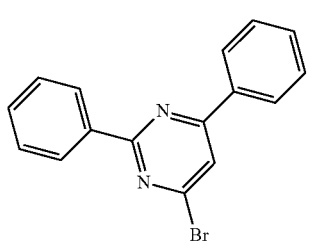
Sub 2-13
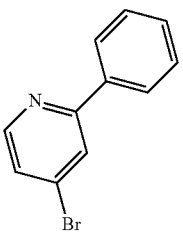
Sub 2-14
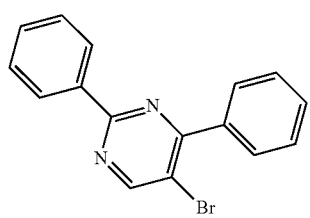
Sub 2-15
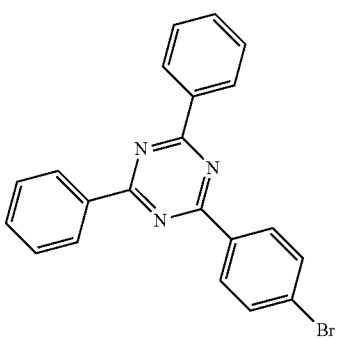
Sub 2-16
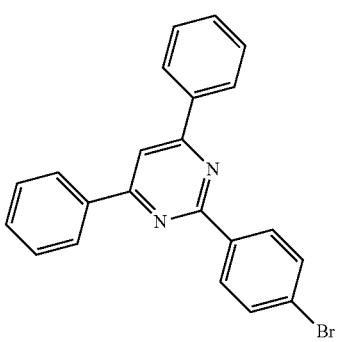
Sub 2-17
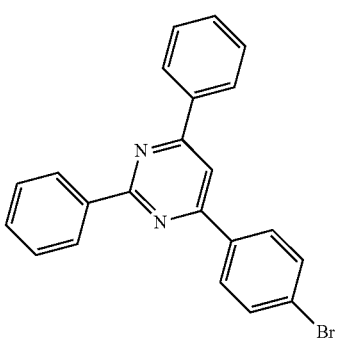

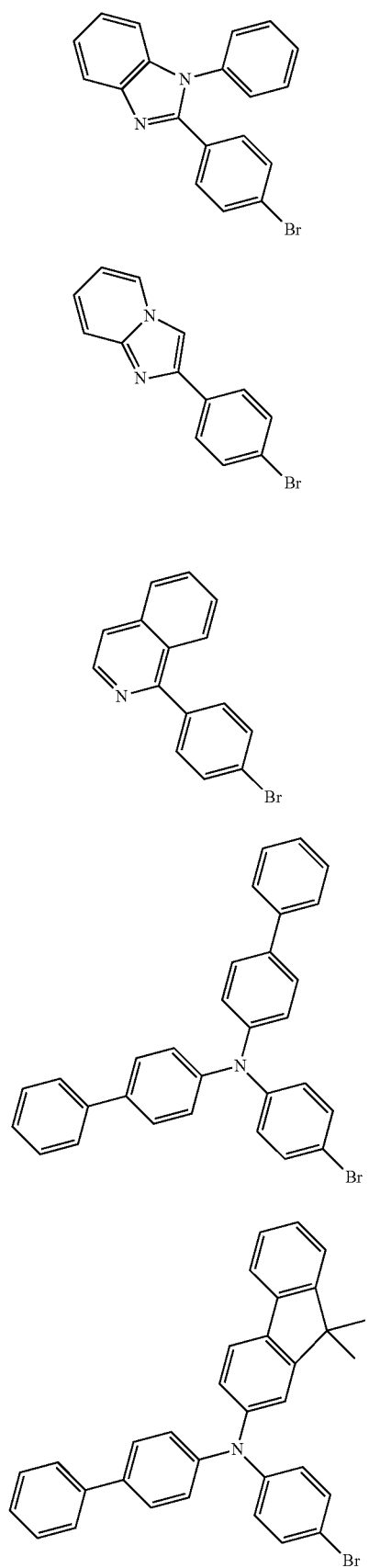
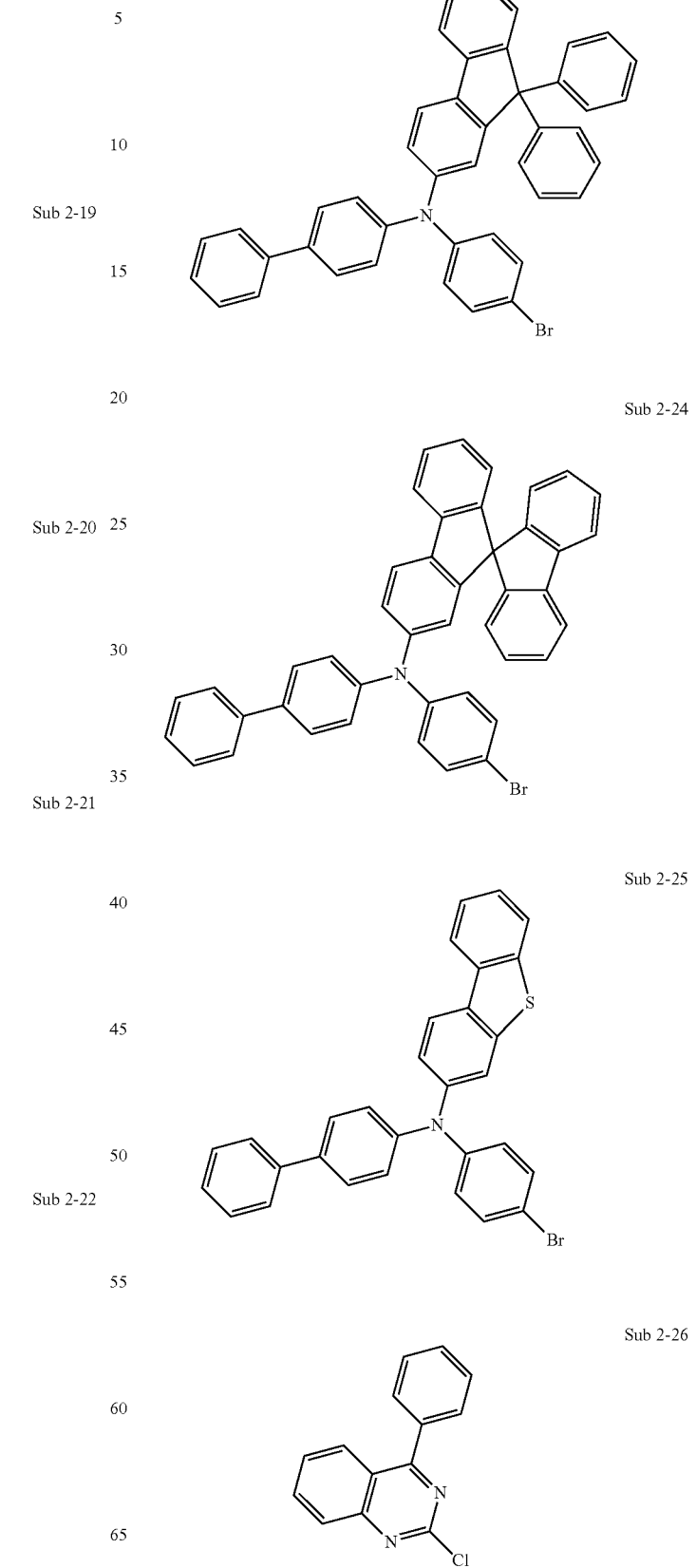

Sub 2-27
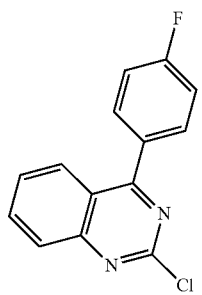
Sub 2-28
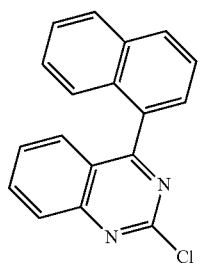
Sub 2-29
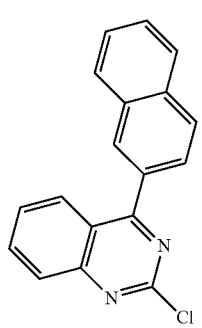
Sub 2-30
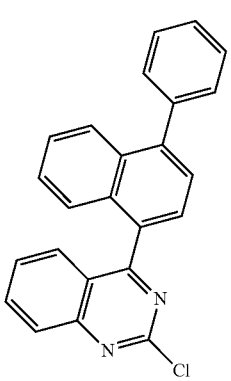
Sub 2-31
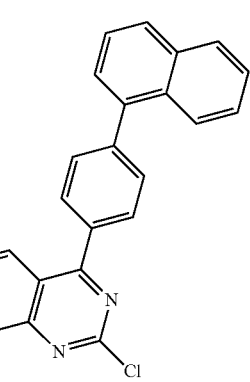
Sub 2-32
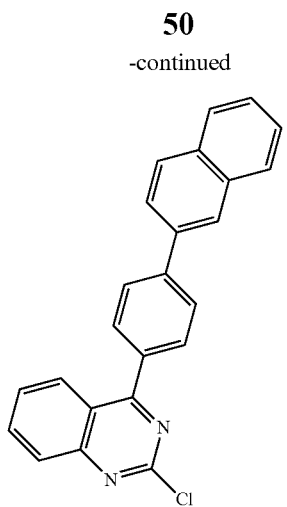
Sub 2-33
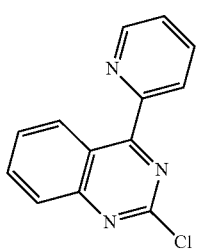
Sub 2-34
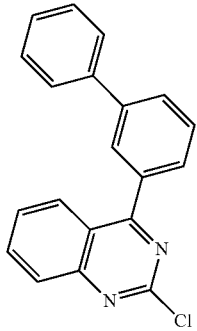
Sub 2-35
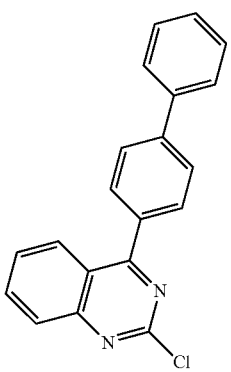

Sub 2-36
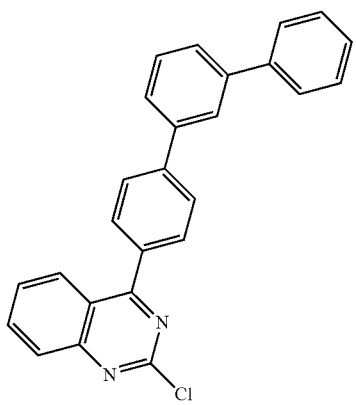
Sub 2-37
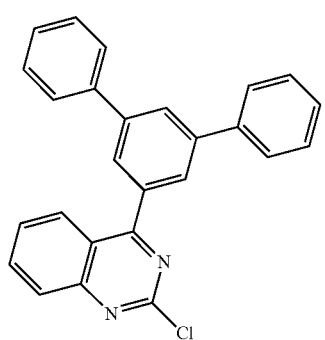
Sub 2-38
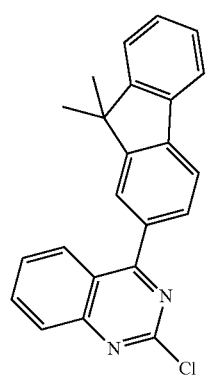
Sub 2-39
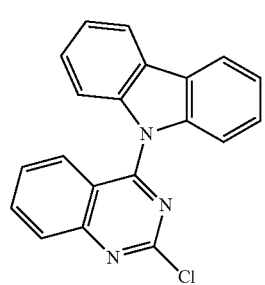
Sub 2-40
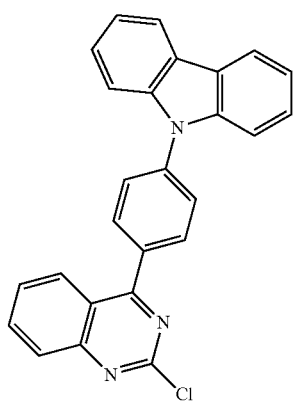
Sub 2-41
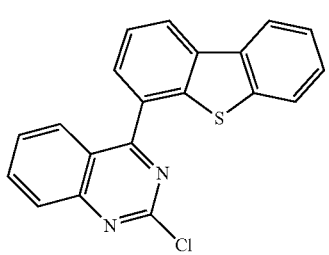
Sub 2-42
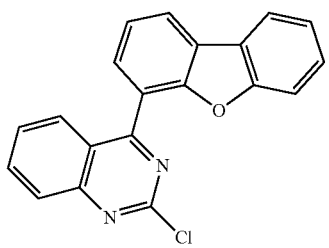
Sub 2-43
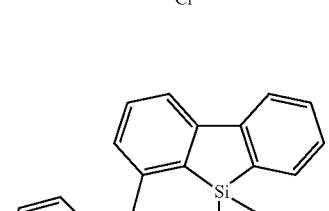
Sub 2-44
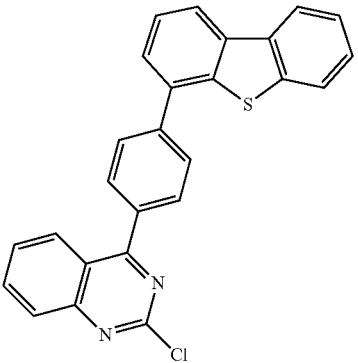

Sub 2-45
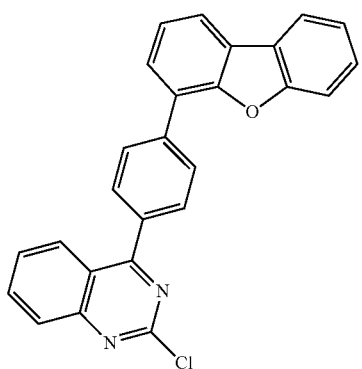
Sub 2-46
Sub 2-47
Sub 2-48
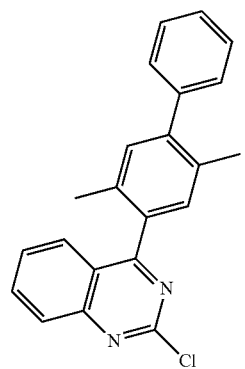
Sub 2-49
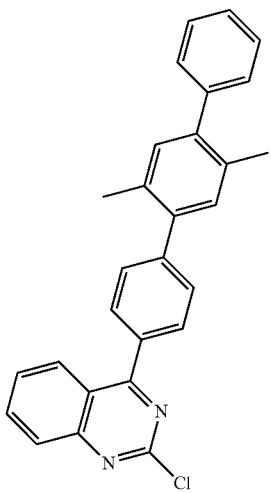
Sub 2-50
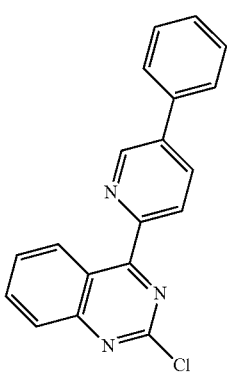
Sub 2-51
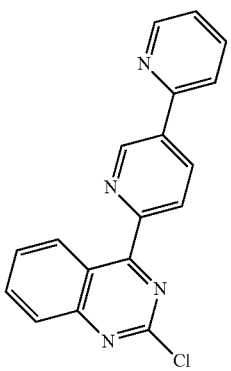
Sub 2-52
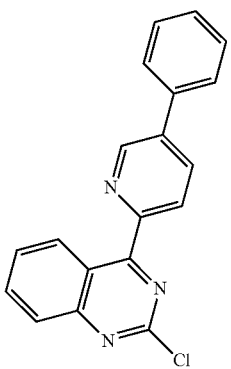

| | |
|---|---|
| Sub 2-53 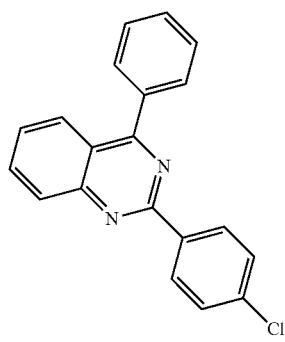 | Sub 2-58 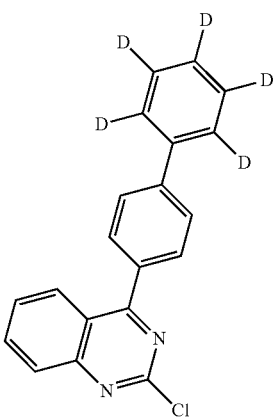 |
| Sub 2-54 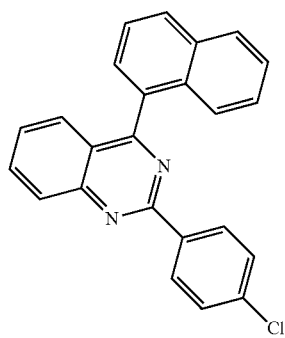 | |
| Sub 2-55 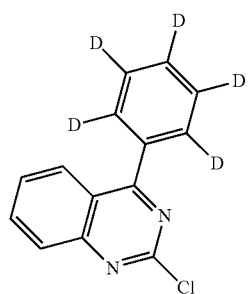 | Sub 2-59 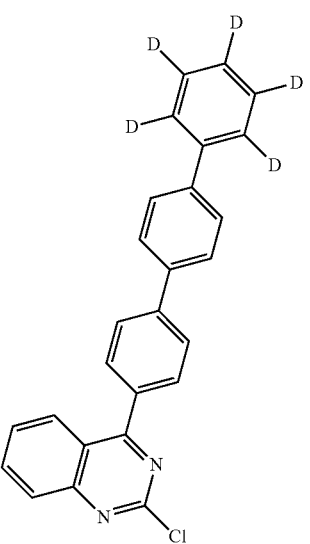 |
| Sub 2-56 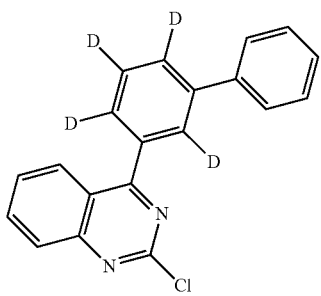 | |
| Sub 2-57 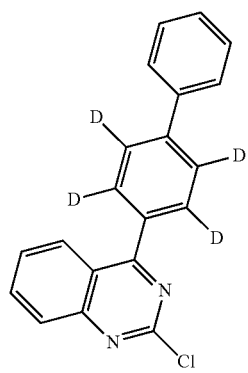 | Sub 2-60 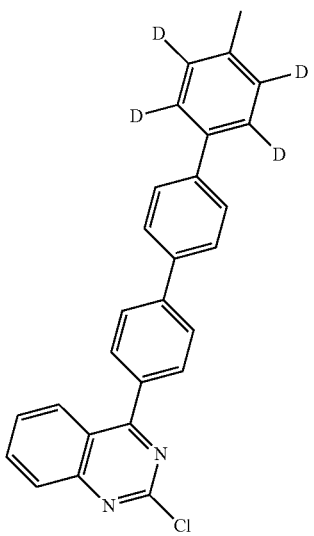 |

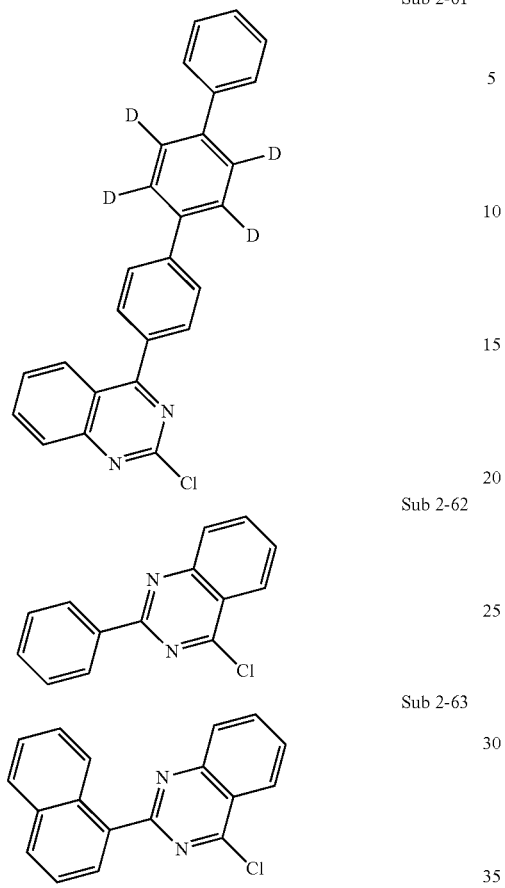

Sub 2-61

Sub 2-62

Sub 2-63

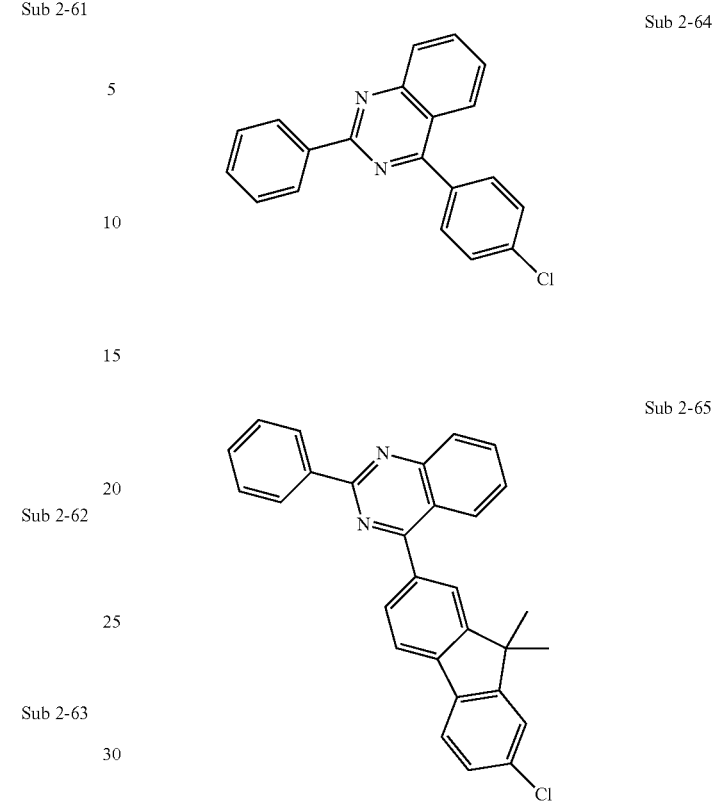

Sub 2-64

Sub 2-65

TABLE 2

| Compound | FD-MS | Compound | FD-MS |
| --- | --- | --- | --- |
| Sub 2-1 | m/z = 155.96 ($C_6H_5Br$ = 157.01) | Sub 2-2 | m/z = 205.97 ($C_{10}H_7Br$ = 207.07) |
| Sub 2-3 | m/z = 205.97 ($C_{10}H_7Br$ = 207.07) | Sub 2-4 | m/z = 231.99 ($C_{12}H_9Br$ = 233.10) |
| Sub 2-5 | m/z = 231.99 ($C_{12}H_9Br$ = 233.10) | Sub 2-6 | m/z = 308.02 ($C_{18}H_{13}Br$ = 233.10) |
| Sub 2-7 | m/z = 255.99 ($C_{14}H_9Br$ = 257.13) | Sub 2-8 | m/z = 255.99 ($C_{14}H_9Br$ = 257.13) |
| Sub 2-9 | m/z = 311.01 ($C_{15}H_{10}BrN_3$ = 312.16) | Sub 2-10 | m/z = 311.01 ($C_{15}H_{10}BrN_3$ = 312.16) |
| Sub 2-11 | m/z = 310.01 ($C_{16}H_{11}BrN_2$ = 311.18) | Sub 2-12 | m/z = 310.01 ($C_{16}H_{11}BrN_2$ = 311.18) |
| Sub 2-13 | m/z = 232.98 ($C_{11}H_8BrN$ = 234.09) | Sub 2-14 | m/z = 310.01 ($C_{16}H_{11}BrN_2$ = 311.18) |
| Sub 2-15 | m/z = 387.04 ($C_{21}H_{14}BrN_3$ = 388.26) | Sub 2-16 | m/z = 386.04 ($C_{22}H_{15}BrN_2$ = 387.27) |
| Sub 2-17 | m/z = 386.04 ($C_{22}H_{15}BrN_2$ = 387.27) | Sub 2-18 | m/z = 348.03 ($C_{19}H_{13}BrN_2$ = 349.22) |
| Sub 2-19 | m/z = 271.99 ($C_{13}H_9BrN_2$ = 273.13) | Sub 2-20 | m/z = 283.00 ($C_{15}H_{10}BrN$ = 284.15) |
| Sub 2-21 | m/z = 475.09 ($C_{30}H_{22}BrN$ = 476.41) | Sub 2-22 | m/z = 515.12 ($C_{33}H_{26}BrN$ = 516.47) |
| Sub 2-23 | m/z = 639.16 ($C_{43}H_{30}BrN$ = 640.61) | Sub 2-24 | m/z = 637.14 ($C_{43}H_{28}BrN$ = 638.59) |
| Sub 2-25 | m/z = 505.05 ($C_{30}H_{20}BrNS$ = 506.46) | Sub 2-26 | m/z = 240.05 ($C_{14}H_9ClN_2$ = 240.69) |
| Sub 2-27 | m/z = 258.04 ($C_{14}H_8ClFN_2$ = 258.68) | Sub 2-28 | m/z = 290.06 ($C_{18}H_{11}ClN_2$ = 290.75) |
| Sub 2-29 | m/z = 290.06 ($C_{18}H_{11}ClN_2$ = 290.75) | Sub 2-30 | m/z = 366.09 ($C_{24}H_{15}ClN_2$ = 366.84) |
| Sub 2-31 | m/z = 366.09 ($C_{24}H_{15}ClN_2$ = 366.84) | Sub 2-32 | m/z = 366.09 ($C_{24}H_{15}ClN_2$ = 366.84) |
| Sub 2-33 | m/z = 241.04 ($C_{13}H_8ClN_3$ = 241.68) | Sub 2-34 | m/z = 316.08 ($C_{20}H_{13}ClN_2$ = 316.78) |
| Sub 2-35 | m/z = 316.08 ($C_{20}H_{13}ClN_2$ = 316.78) | Sub 2-36 | m/z = 392.11 ($C_{26}H_{17}ClN_2$ = 392.88) |
| Sub 2-37 | m/z = 392.11 ($C_{26}H_{17}ClN_2$ = 392.88) | Sub 2-38 | m/z = 356.11 ($C_{23}H_{17}ClN_2$ = 356.85) |
| Sub 2-39 | m/z = 329.07 ($C_{20}H_{12}ClN_3$ = 329.78) | Sub 2-40 | m/z = 405.10 ($C_{26}H_{16}ClN_3$ = 405.88) |
| Sub 2-41 | m/z = 346.03 ($C_{20}H_{11}ClN_2S$ = 346.83) | Sub 2-42 | m/z = 330.06 ($C_{20}H_{11}ClN_2O$ = 330.77) |
| Sub 2-43 | m/z = 372.08 ($C_{22}H_{17}ClN_2Si$ = 372.92) | Sub 2-44 | m/z = 422.06 ($C_{26}H_{15}ClN_2S$ = 422.93) |
| Sub 2-45 | m/z = 406.09 ($C_{26}H_{15}ClN_2O$ = 406.86) | Sub 2-46 | m/z = 448.12 ($C_{28}H_{21}ClN_2Si$ = 449.02) |
| Sub 2-47 | m/z = 268.08 ($C_{16}H_{13}ClN_2$ = 268.74) | Sub 2-48 | m/z = 420.14 ($C_{28}H_{21}ClN_2$ = 344.84) |
| Sub 2-49 | m/z = 420.14 ($C_{28}H_{21}ClN_2$ = 420.93) | Sub 2-50 | m/z = 317.07 ($C_{19}H_{12}ClN_3$ = 317.77) |
| Sub 2-51 | m/z = 318.07 ($C_{18}H_{11}ClN_4$ = 318.76) | Sub 2-52 | m/z = 317.07 ($C_{19}H_{12}ClN_3$ = 317.77) |
| Sub 2-53 | m/z = 316.08 ($C_{20}H_{13}ClN_2$ = 316.78) | Sub 2-54 | m/z = 366.09 ($C_{24}H_{15}ClN_2$ = 366.84) |
| Sub 2-55 | m/z = 245.08 ($C_{14}H_4D_5ClN_2$ = 245.72) | Sub 2-56 | m/z = 320.10 ($C_{20}H_5D_4ClN_2$ = 320.81) |

TABLE 2-continued

| Compound | FD-MS | Compound | FD-MS |
|---|---|---|---|
| Sub 2-57 | m/z = 320.10 (C$_{20}$H$_5$D$_4$ClN$_2$ = 320.81) | Sub 2-58 | m/z = 320.10 (C$_{20}$H$_5$D$_4$ClN$_2$ = 320.81) |
| Sub 2-59 | m/z = 397.14 (C$_{26}$H$_{12}$D$_5$ClN$_2$ = 397.9) | Sub 2-60 | m/z = 410.15 (C$_{27}$H$_{15}$D$_4$ClN$_2$ = 410.93) |
| Sub 2-61 | m/z = 396.13 (C$_{26}$H$_{13}$D$_4$ClN$_2$ = 396.9) | | |
| Sub 2-63 | m/z = 290.06 (C$_{18}$H$_{11}$ClN$_2$ = 290.75) | Sub 2-62 | m/z = 240.05 (C$_{14}$H$_9$ClN$_2$ = 240.69) |
| Sub 2-65 | m/z = 432.14 (C$_{29}$H$_{21}$ClN$_2$ = 432.94) | Sub 2-64 | m/z = 316.08 (C$_{20}$H$_{13}$ClN$_2$ = 316.78) |

3. Synthesis Method of Product

A mixture of Sub 1 (1 eq.), Sub 2 (1.2 eq.), Pd$_2$(dba)$_3$ (0.05 eq.), P(t-Bu)$_3$ (0.1 eq.), NaOt-Bu (3 eq.) and toluene (10.5 mL/1 mmol) in a round bottom flask was reacted at 100° C. Upon completion the reaction, the reaction solution was extracted with ether and water. The organic layer was dried over MgSO$_4$ and concentrated under vacuum, and then the produced organic material was separated by a silica gel chromatography and recrystallization to obtain product.

(1) Synthesis Method of 1-1

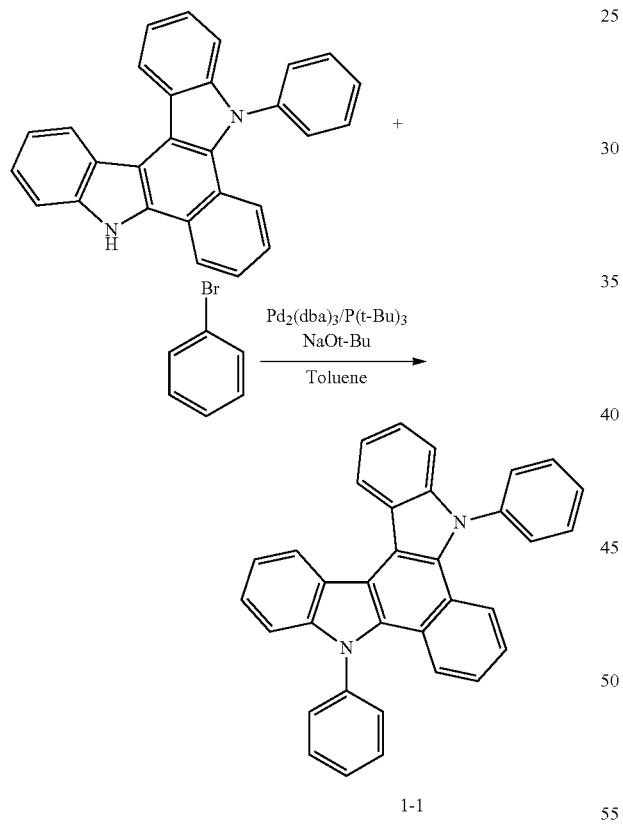

1-1

(2) Synthesis Method of 1-29

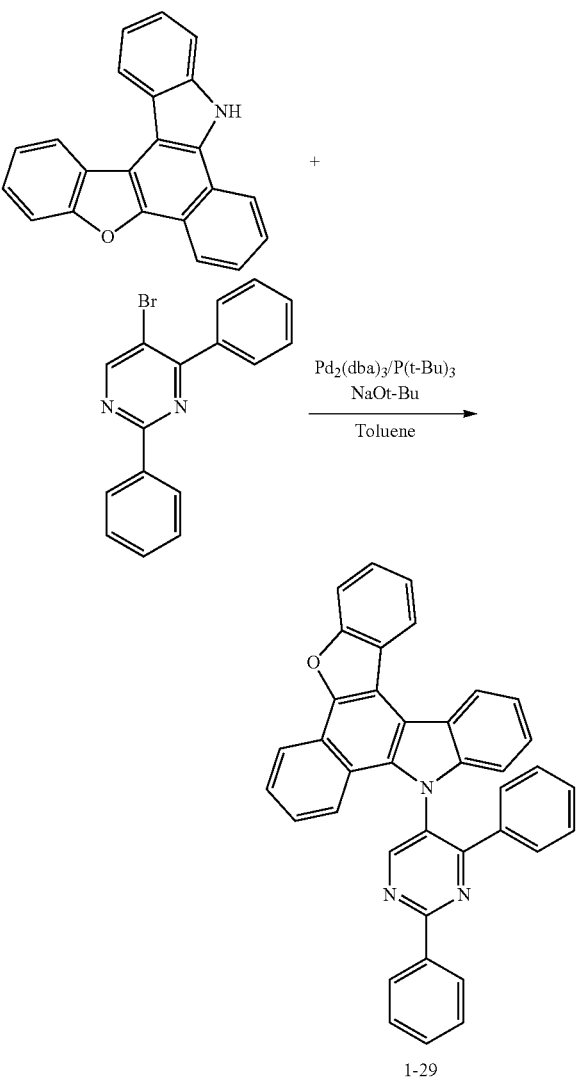

1-29

A mixture of 5-phenyl-5,10-dihydrobenzo[a]indolo[2,3-c]carbazole (7.6 g, 20 mmol), bromobenzene (3.7 g, 24 mmol), Pd$_2$(dba)$_3$ (0.03~0.05 mmol), P(t-Bu)$_3$ (0.1 eq), NaOt-Bu (3 eq) and toluene (10.5 mL/1 mmol) in a round bottom flask was reacted at 100° C. Upon completion the reaction, the reaction solution was extracted with ether and water. The organic layer was dried over MgSO$_4$ and concentrated under vacuum, and then the produced organic material was separated by a silica gel chromatography and recrystallization to obtain 6.2 g of product (yield: 68%).

A mixture of 10H-benzo[a]benzofuro[2,3-c]carbazole (6.1 g, 20 mmol), 5-bromo-2,4-diphenylpyrimidine (7.5 g, 24 mmol), Pd$_2$(dba)$_3$ (0.03~0.05 mmol), P(t-Bu)$_3$ (0.1 eq), NaOt-Bu (3 eq) and toluene (10.5 mL/1 mmol) in a round bottom flask was reacted at 100° C. Upon completion the reaction, the reaction solution was extracted with ether and water. The organic layer was dried over MgSO$_4$ and concentrated under vacuum, and then the produced organic material was separated by a silica gel chromatography and recrystallization to obtain 6.6 g of product (yield: 61%).

(3) Synthesis Method of 2-1

(4) Synthesis Method of 2-46

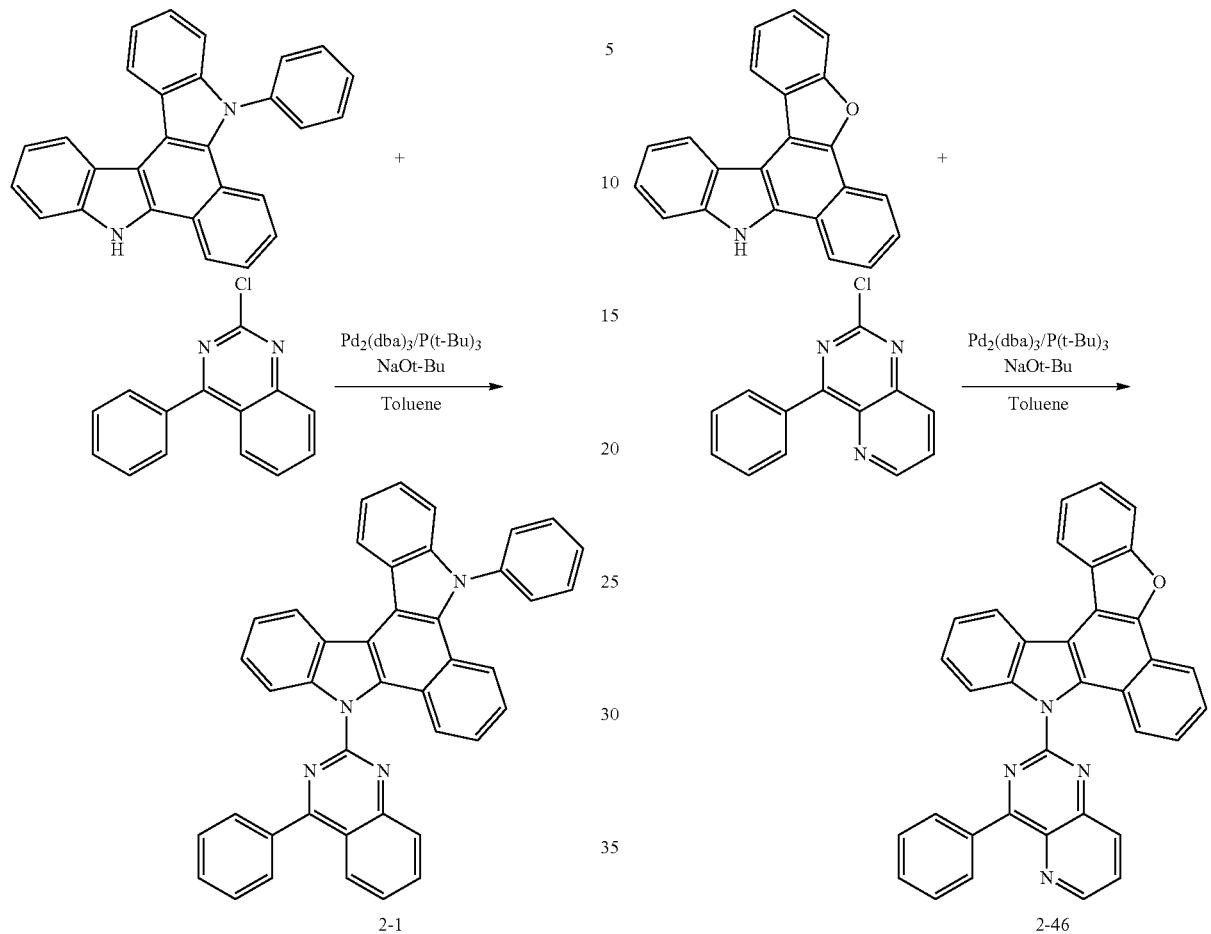

A mixture of 5-phenyl-5,10-dihydrobenzo[a]indolo[2,3-c]carbazole (7.6 g, 20 mmol), 2-chloro-4-phenylquinazoline (5.8 g, 24 mmol), $Pd_2(dba)_3$ (0.03~0.05 mmol), P(t-Bu)$_3$ (0.1 eq), NaOt-Bu (3 eq) and toluene (10.5 mL/1 mmol) in a round bottom flask was reacted at 100° C. Upon completion the reaction, the reaction solution was extracted with ether and water. The organic layer was dried over $MgSO_4$ and concentrated under vacuum, and then the produced organic material was separated by a silica gel chromatography and recrystallization to obtain 7.9 g of product (yield: 67%).

A mixture of 10H-benzo[a]benzofuro[2,3-c]carbazole (6.1 g, 20 mmol), 2-chloro-4-phenylpyrido[3,2-d]pyrimidine (5.8 g, 24 mmol), $Pd_2(dba)_3$ (0.03~0.05 mmol), P(t-Bu)$_3$ (0.1 당량), NaOt-Bu (3 당량) and toluene (10.5 mL/1 mmol) in a round bottom flask was reacted at 100° C. Upon completion the reaction, the reaction solution was extracted with ether and water. The organic layer was dried over $MgSO_4$ and concentrated under vacuum, and then the produced organic material was separated by a silica gel chromatography and recrystallization to obtain 5.9 g of product (yield: 58%).

TABLE 3

| Compound | FD-MS | Compound | FD-MS |
|---|---|---|---|
| 1-1 | m/z = 458.18 ($C_{34}H_{22}N_2$ = 458.55) | 1-2 | m/z = 508.19 ($C_{38}H_{24}N_2$ = 508.61) |
| 1-3 | m/z = 508.19 ($C_{38}H_{24}N_2$ = 508.61) | 1-4 | m/z = 534.21 ($C_{40}H_{26}N_2$ = 534.65) |
| 1-5 | m/z = 613.23 ($C_{43}H_{27}N_5$ = 613.71) | 1-6 | m/z = 613.71 ($C_{43}H_{27}N_5$ = 613.71) |
| 1-7 | m/z = 612.23 ($C_{44}H_{28}N_4$ = 612.72) | 1-8 | m/z = 612.23 ($C_{44}H_{28}N_4$ = 612.72) |
| 1-9 | m/z = 612.23 ($C_{44}H_{28}N_4$ = 612.72) | 1-10 | m/z = 689.26 ($C_{49}H_{31}N_5$ = 689.80) |
| 1-11 | m/z = 688.26 ($C_{50}H_{32}N_4$ = 688.82) | 1-12 | m/z = 688.26 ($C_{50}H_{32}N_4$ = 688.82) |
| 1-13 | m/z = 650.25 ($C_{47}H_{30}N_4$ = 650.77) | 1-14 | m/z = 574.22 ($C_{41}H_{26}N_4$ = 574.67) |
| 1-15 | m/z = 625.25 ($C_{46}H_{31}N_3$ = 625.76) | 1-16 | m/z = 534.21 ($C_{40}H_{26}N_2$ = 534.65) |
| 1-17 | m/z = 534.21 ($C_{40}H_{26}N_2$ = 534.65) | 1-18 | m/z = 625.25 ($C_{46}H_{31}N_3$ = 625.76) |
| 1-19 | m/z = 701.28 ($C_{52}H_{35}N_3$ = 701.85) | 1-20 | m/z = 610.24 ($C_{46}H_{30}N_2$ = 610.74) |
| 1-21 | m/z = 383.13 ($C_{28}H_{17}NO$ = 383.44) | 1-22 | m/z = 433.15 ($C_{32}H_{19}NO$ = 43350) |
| 1-23 | m/z = 433.15 ($C_{32}H_{19}NO$ = 43350) | 1-24 | m/z = 459.16 ($C_{34}H_{21}NO$ = 459.54) |

TABLE 3-continued

| Compound | FD-MS | Compound | FD-MS |
|---|---|---|---|
| 1-25 | m/z = 538.18 ($C_{37}H_{22}N_4O$ = 538.60) | 1-26 | m/z = 538.18 ($C_{37}H_{22}N_4O$ = 538.60) |
| 1-27 | m/z = 537.18 ($C_{38}H_{32}N_3O$ = 537.61) | 1-28 | m/z = 537.18 ($C_{38}H_{32}N_3O$ = 537.61) |
| 1-29 | m/z = 537.18 ($C_{38}H_{32}N_3O$ = 537.61) | 1-30 | m/z = 614.21 ($C_{43}H_{26}N_4O$ = 614.69) |
| 1-31 | m/z = 613.22 ($C_{44}H_{27}N_3O$ = 613.70) | 1-32 | m/z = 613.22 ($C_{44}H_{27}N_3O$ = 613.70) |
| 1-33 | m/z = 575.20 ($C_{41}H_{25}N_3O$ = 575.66) | 1-34 | m/z = 499.17 ($C_{35}H_{21}N_3O$ = 499.56) |
| 1-35 | m/z = 550.20 ($C_{40}H_{26}N_2O$ = 550.65) | 1-36 | m/z = 459.16 ($C_{34}H_{21}NO$ = 459.54) |
| 1-37 | m/z = 459.16 ($C_{34}H_{21}NO$ = 459.54) | 1-38 | m/z = 550.20 ($C_{40}H_{26}N_2O$ = 550.65) |
| 1-39 | m/z = 626.24 ($C_{46}H_{30}N_2O$ = 626.74) | 1-40 | m/z = 535.19 ($C_{40}H_{25}NO$ = 535.63) |
| 2-1 | m/z = 586.22 ($C_{42}H_{26}N_4$ = 586.68) | 2-2 | m/z = 662.25 ($C_{48}H_{30}N_4$ = 662.78) |
| 2-3 | m/z = 662.25 ($C_{48}H_{30}N_4$ = 662.78) | 2-4 | m/z = 636.23 ($C_{46}H_{28}N_4$ = 636.74) |
| 2-5 | m/z = 636.23 ($C_{46}H_{28}N_4$ = 636.74) | 2-6 | m/z = 712.26 ($C_{52}H_{32}N_4$ = 712.84) |
| 2-7 | m/z = 712.26 ($C_{52}H_{32}N_4$ = 712.84) | 2-8 | m/z = 712.26 ($C_{52}H_{32}N_4$ = 712.84) |
| 2-9 | m/z = 712.26 ($C_{52}H_{32}N_4$ = 712.84) | 2-10 | m/z = 686.25 ($C_{50}H_{30}N_4$ = 686.80) |
| 2-11 | m/z = 702.28 ($C_{51}H_{34}N_4$ = 702.84) | 2-12 | m/z = 692.20 ($C_{48}H_{28}N_4S$ = 692.83) |
| 2-13 | m/z = 751.27 ($C_{54}H_{33}N_5$ = 751.87) | 2-14 | m/z = 676.23 ($C_{48}H_{28}N_4O$ = 676.76) |
| 2-15 | m/z = 662.25 ($C_{48}H_{30}N_4$ = 662.78) | 2-16 | m/z = 636.23 ($C_{46}H_{28}N_4$ = 636.74) |
| 2-17 | m/z = 636.23 ($C_{46}H_{28}N_4$ = 636.74) | 2-18 | m/z = 662.25 ($C_{48}H_{30}N_4$ = 662.78) |
| 2-19 | m/z = 587.21 ($C_{41}H_{25}N_5$ = 587.67) | 2-20 | m/z = 587.21 ($C_{41}H_{25}N_5$ = 587.67) |
| 2-21 | m/z = 587.21 ($C_{41}H_{25}N_5$ = 587.67) | 2-22 | m/z = 587.21 ($C_{41}H_{25}N_5$ = 587.67) |
| 2-23 | m/z = 662.25 ($C_{48}H_{30}N_4$ = 662.78) | 2-24 | m/z = 662.25 ($C_{48}H_{30}N_4$ = 662.78) |
| 2-25 | m/z = 511.17 ($C_{36}H_{21}N_3O$ = 511.57) | 2-26 | m/z = 587.20 ($C_{42}H_{25}N_3O$ = 587.67) |
| 2-27 | m/z = 587.20 ($C_{42}H_{25}N_3O$ = 587.67) | 2-28 | m/z = 561.18 ($C_{40}H_{23}N_3O$ = 561.63) |
| 2-29 | m/z = 561.18 ($C_{40}H_{23}N_3O$ = 561.63) | 2-30 | m/z = 637.22 ($C_{46}H_{27}N_3O$ = 637.73) |
| 2-31 | m/z = 637.22 ($C_{46}H_{27}N_3O$ = 637.73) | 2-32 | m/z = 637.22 ($C_{46}H_{27}N_3O$ = 637.73) |
| 2-33 | m/z = 637.22 ($C_{46}H_{27}N_3O$ = 637.73) | 2-34 | m/z = 611.20 ($C_{44}H_{25}N_3O$ = 611.69) |
| 2-35 | m/z = 627.23 ($C_{45}H_{29}N_3O$ = 627.73) | 2-36 | m/z = 617.16 ($C_{42}H_{23}N_3OS$ = 617.72) |
| 2-37 | m/z = 676.23 ($C_{48}H_{28}N_4O$ = 676.76) | 2-38 | m/z = 601.18 ($C_{42}H_{23}N_3O_2$ = 601.65) |
| 2-39 | m/z = 587.20 ($C_{42}H_{25}N_3O$ = 587.67) | 2-40 | m/z = 637.22 ($C_{46}H_{27}N_3O$ = 693.73) |
| 2-41 | m/z = 637.22 ($C_{46}H_{27}N_3O$ = 637.73) | 2-42 | m/z = 587.20 ($C_{42}H_{25}N_3O$ = 587.67) |
| 2-43 | m/z = 512.16 ($C_{35}H_{20}N_4O$ = 512.56) | 2-44 | m/z = 512.16 ($C_{35}H_{20}N_4O$ = 512.56) |
| 2-45 | m/z = 512.16 ($C_{35}H_{20}N_4O$ = 512.56) | 2-46 | m/z = 512.16 ($C_{35}H_{20}N_4O$ = 512.56) |
| 2-47 | m/z = 587.20 ($C_{42}H_{25}N_3O$ = 587.67) | 2-48 | m/z = 587.20 ($C_{42}H_{25}N_3O$ = 587.67) |

Fabrication and Evaluation of Organic Electronic Element

[Example 1] Green Organic Light Emitting Diode (a Phosphorescent Host)

Organic light emitting diodes (OLEDs) were fabricated according to a conventional method by using a compound of the present invention as a phosphorescent host material. First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Subsequently, 4,4-bis[N-(1-naphthyl)-N-phenylamino]biphenyl (hereinafter abbreviated as "NPD") was vacuum-deposited with a thickness of 20 nm on the hole injection layer to form a hole transport layer. Subsequently, a light emitting layer with a thickness of 30 nm was deposited on the hole transport layer by doping the hole transport layer with the compound 1-1 of the present invention as a host material and tris(2-phenylpyridine)-iridium (hereinafter abbreviated as "Ir(ppy)$_3$") as a dopant material in a weight ratio of 95:5. Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato) aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 40] Green Organic Light Emitting Diode (a Phosphorescent Host)

The OLEDs were manufactured in the same manner as described in Example 1, except that any one of the compounds 1-2 to 1-40 of the present invention in the Table 4 below was used as the host material of the light emitting layer, instead of the inventive compound 1-1.

Comparative Example 1

An OLED was manufactured in the same manner as described in Example 1, except that the following Comparative Compound 1 was used as the host material of the light emitting layer, instead of the inventive compound 1-1.
<Comparative Compound 1>

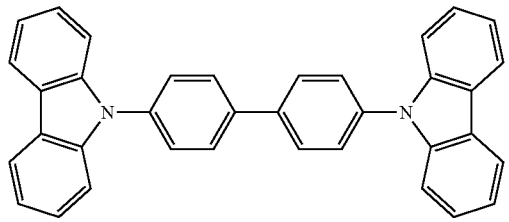 [SMILES: c1ccc2c(c1)c1ccccc1n2-c1ccc(-c2ccc(-n3c4ccccc4c4ccccc43)cc2)cc1]

Comparative Example 2

An OLED was manufactured in the same manner as described in Example 1, except that the following Comparative Compound 2 was used as the host material of the light emitting layer, instead of the inventive compound 1-1.
<Comparative Compound 2>

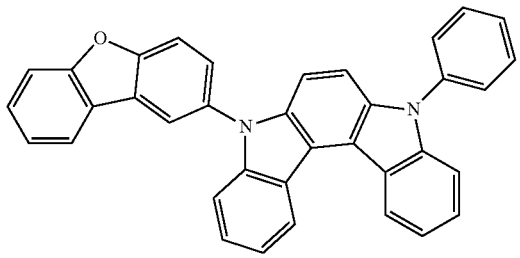 [SMILES: c1ccc(-n2c3ccccc3c3c4c5ccccc5n(-c5ccc6oc7ccccc7c6c5)c4ccc32)cc1]

Comparative Example 3

An OLED was manufactured in the same manner as described in Example 1, except that the following Comparative Compound 3 was used as the host material of the light emitting layer, instead of the inventive compound 1-1.
<Comparative Compound 3>

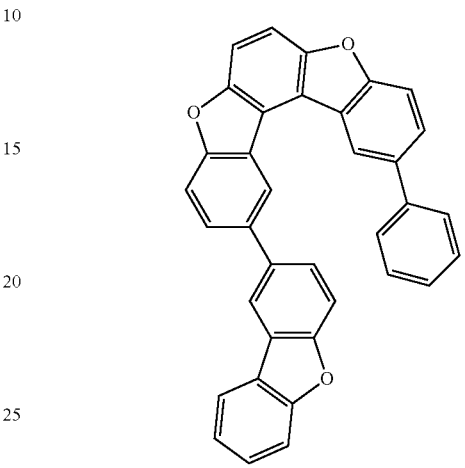

A forward bias DC voltage was applied to each of the OLEDs manufactured through the Examples 1 to 40 and the Comparative Examples 1 to 3, and electro-luminescence (EL) characteristics of the OLED were measured by PR-650 (Photoresearch). Also, T90 life span was measured by life span measuring equipment (Mcscience) at the reference brightness of 300 cd/m². Evaluation results are in the Table 4 below.

TABLE 4

|   | Compound | Voltage (V) | Current Density (mA/cm²) | Brightness (cd/m²) | Efficiency (cd/A) | Lifetime T (90) | CIE (x, y) |
|---|---|---|---|---|---|---|---|
| comp. Ex. (1) | comp. Com. 1 | 6.6 | 8.6 | 300.0 | 3.5 | 58.6 | (0.31, 0.60) |
| comp. Ex. (2) | comp. Com. 2 | 6.1 | 6.9 | 300.0 | 4.3 | 74.6 | (0.33, 0.61) |
| comp. Ex. (3) | comp. Com. 3 | 6.2 | 7.4 | 300.0 | 4.1 | 66.6 | (0.32, 0.60) |
| Ex. (1) | Com. (1-1) | 5.2 | 4.1 | 300.0 | 7.3 | 92.4 | (0.33, 0.60) |
| Ex. (2) | Com. (1-2) | 5.2 | 4.3 | 300.0 | 6.9 | 145.3 | (0.30, 0.60) |
| Ex. (3) | Com. (1-3) | 5.2 | 4.5 | 300.0 | 6.7 | 149.2 | (0.30, 0.61) |
| Ex. (4) | Com. (1-4) | 5.2 | 4.4 | 300.0 | 6.8 | 137.3 | (0.32, 0.61) |
| Ex. (5) | Com. (1-5) | 5.2 | 4.3 | 300.0 | 7.0 | 103.1 | (0.31, 0.61) |
| Ex. (6) | Com. (1-6) | 5.2 | 4.4 | 300.0 | 6.8 | 120.6 | (0.31, 0.60) |
| Ex. (7) | Com. (1-7) | 5.2 | 4.5 | 300.0 | 6.7 | 105.1 | (0.31, 0.60) |
| Ex. (8) | Com. (1-8) | 5.3 | 4.2 | 300.0 | 7.2 | 100.7 | (0.32, 0.61) |
| Ex. (9) | Com. (1-9) | 5.1 | 4.4 | 300.0 | 6.8 | 123.4 | (0.31, 0.61) |
| Ex. (10) | Com. (1-10) | 5.1 | 4.5 | 300.0 | 6.7 | 105.9 | (0.33, 0.60) |
| Ex. (11) | Com. (1-11) | 5.0 | 4.0 | 300.0 | 7.4 | 146.9 | (0.31, 0.60) |
| Ex. (12) | Com. (1-12) | 5.3 | 4.1 | 300.0 | 7.3 | 95.8 | (0.32, 0.61) |
| Ex. (13) | Com. (1-13) | 5.0 | 4.5 | 300.0 | 6.6 | 107.2 | (0.32, 0.61) |
| Ex. (14) | Com. (1-14) | 5.2 | 4.3 | 300.0 | 7.0 | 103.1 | (0.33, 0.60) |
| Ex. (15) | Com. (1-15) | 5.1 | 4.3 | 300.0 | 6.9 | 122.6 | (0.30, 0.61) |
| Ex. (16) | Com. (1-16) | 5.1 | 4.4 | 300.0 | 6.9 | 116.6 | (0.31, 0.61) |
| Ex. (17) | Com. (1-17) | 5.0 | 4.4 | 300.0 | 6.8 | 122.9 | (0.31, 0.60) |
| Ex. (18) | Com. (1-18) | 5.3 | 4.2 | 300.0 | 7.2 | 129.8 | (0.33, 0.61) |

TABLE 4-continued

| | Compound | Voltage (V) | Current Density (mA/cm²) | Brightness (cd/m²) | Efficiency (cd/A) | Lifetime T (90) | CIE (x, y) |
|---|---|---|---|---|---|---|---|
| Ex. (19) | Com. (1-19) | 5.2 | 4.1 | 300.0 | 7.4 | 113.0 | (0.32, 0.61) |
| Ex. (20) | Com. (1-20) | 5.1 | 4.4 | 300.0 | 6.7 | 116.6 | (0.33, 0.60) |
| Ex. (21) | Com. (1-21) | 5.4 | 5.0 | 300.0 | 6.0 | 148.5 | (0.30, 0.61) |
| Ex. (22) | Com. (1-22) | 5.5 | 4.8 | 300.0 | 6.2 | 100.4 | (0.31, 0.61) |
| Ex. (23) | Com. (1-23) | 5.6 | 5.0 | 300.0 | 6.0 | 130.1 | (0.31, 0.60) |
| Ex. (24) | Com. (1-24) | 5.4 | 4.9 | 300.0 | 6.1 | 122.4 | (0.33, 0.61) |
| Ex. (25) | Com. (1-25) | 5.5 | 4.9 | 300.0 | 6.2 | 136.1 | (0.32, 0.60) |
| Ex. (26) | Com. (1-26) | 5.3 | 4.9 | 300.0 | 6.1 | 149.8 | (0.32, 0.61) |
| Ex. (27) | Com. (1-27) | 5.5 | 4.8 | 300.0 | 6.2 | 92.6 | (0.33, 0.60) |
| Ex. (28) | Com. (1-28) | 5.6 | 4.8 | 300.0 | 6.3 | 110.1 | (0.30, 0.60) |
| Ex. (29) | Com. (1-29) | 5.6 | 4.8 | 300.0 | 6.3 | 105.6 | (0.30, 0.61) |
| Ex. (30) | Com. (1-30) | 5.4 | 4.8 | 300.0 | 6.2 | 148.1 | (0.32, 0.61) |
| Ex. (31) | Com. (1-31) | 5.5 | 4.9 | 300.0 | 6.1 | 147.9 | (0.31, 0.61) |
| Ex. (32) | Com. (1-32) | 5.6 | 4.8 | 300.0 | 6.3 | 111.1 | (0.31, 0.60) |
| Ex. (33) | Com. (1-33) | 5.4 | 4.8 | 300.0 | 6.3 | 108.0 | (0.31, 0.60) |
| Ex. (34) | Com. (1-34) | 5.5 | 4.7 | 300.0 | 6.4 | 149.9 | (0.32, 0.61) |
| Ex. (35) | Com. (1-35) | 5.6 | 4.6 | 300.0 | 6.5 | 149.4 | (0.31, 0.61) |
| Ex. (36) | Com. (1-36) | 5.3 | 4.7 | 300.0 | 6.4 | 148.6 | (0.33, 0.60) |
| Ex. (37) | Com. (1-37) | 5.5 | 4.9 | 300.0 | 6.2 | 137.4 | (0.31, 0.60) |
| Ex. (38) | Com. (1-38) | 5.4 | 4.6 | 300.0 | 6.5 | 136.1 | (0.32, 0.61) |
| Ex. (39) | Com. (1-39) | 5.5 | 4.6 | 300.0 | 6.5 | 149.1 | (0.32, 0.61) |
| Ex. (40) | Com. (1-40) | 5.3 | 5.0 | 300.0 | 6.0 | 148.5 | (0.33, 0.60) |

As shown in the Table 4 above, the OLEDs using the materials for OLEDs of the present invention as green light emitting layer materials were found to be high luminous efficiency, low driving voltage, and to be significantly improved in life span.

In particular, the Comparative compounds 2 and 3 comprising 5-membered heterocyclic ring and 5-ring fused heterocyclic ring as a core, were shown much better results than the comparative compound 1, CBP, that is a type of biscarbazole. And the compounds of the present invention comprising 6-ring fused heterocyclic ring fused one more benzene ring, were shown lower driving voltage, higher luminous efficiency and life span. The reason may be that added benzene ring to the fused ring may enhance thermal stability and cause good energy balance by sharing a proper energy level with adjacent layer.

[Example 41] Red Organic Light Emitting Diode (a Phosphorescent Host)

Organic light emitting diodes (OLEDs) were fabricated according to a conventional method by using a compound of the present invention as a phosphorescent host material. First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 20 nm on the hole injection layer to form a hole transport layer. Subsequently, a light emitting layer with a thickness of 30 nm was deposited on the hole transport layer by doping the hole transport layer with the compound 2-1 of the present invention as a host material and bis-(1-phenylisoquinolyl)iridium(III)acetylacetonate (hereinafter abbreviated as "(piq)$_2$Ir(acac)") as a dopant material in a weight ratio of 95:5. Next, a film of BAlq was vacuum-deposited with a thickness of 10 nm on the light emitting layer to form a hole blocking layer, and a film of Alq$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 42] to [Example 88] Red Organic Light Emitting Diode (a Phosphorescent Host)

The OLEDs were manufactured in the same manner as described in Example 41, except that any one of the compounds 2-2 to 2-48 of the present invention in the Table 5 below was used as the host material of the a light emitting layer, instead of the inventive compound 2-1.

Comparative Example 4

An OLED was manufactured in the same manner as described in Example 41, except that Comparative Compound 1 represented above was used as the host material of the a light emitting layer, instead of the inventive compound 2-1.

Comparative Example 5

An OLED was manufactured in the same manner as described in Example 41, except that Comparative Compound 2 represented above was used as the host material of the a light emitting layer, instead of the inventive compound 2-1.

Comparative Example 6

An OLED was manufactured in the same manner as described in Example 41, except that Comparative Compound 3 represented above was used as the host material of the a light emitting layer, instead of the inventive compound 2-1.

A forward bias DC voltage was applied to each of the OLEDs manufactured through the Examples 41 to 88 and Comparative Examples 4 to 6, and electro-luminescence (EL) characteristics of the OLED were measured by PR-650 (Photoresearch). Also, T90 life span was measured by lifespan measuring equipment (Mcscience) at the reference brightness of 300 cd/m². Evaluation results are in the Table 5 below.

TABLE 5

| | Compound | Voltage (V) | Current Density (mA/cm$^2$) | Brightness (cd/m$^2$) | Efficiency (cd/A) | Lifetime T (90) | CIE (x, y) |
|---|---|---|---|---|---|---|---|
| comp. Ex. (4) | comp. Com. 1 | 6.8 | 8.6 | 300.0 | 3.5 | 58.6 | (0.66, 0.32) |
| comp. Ex. (5) | comp. Com. 2 | 6.2 | 6.9 | 300.0 | 4.3 | 74.6 | (0.67, 0.32) |
| comp. Ex. (6) | comp. Com. 3 | 6.4 | 7.4 | 300.0 | 4.1 | 66.6 | (0.66, 0.32) |
| Ex. (41) | Com. (2-1) | 5.2 | 4.1 | 300.0 | 7.3 | 97.0 | (0.66, 0.32) |
| Ex. (42) | Com. (2-2) | 5.1 | 4.4 | 300.0 | 6.9 | 133.7 | (0.66, 0.32) |
| Ex. (43) | Com. (2-3) | 5.5 | 4.5 | 300.0 | 6.7 | 109.8 | (0.67, 0.32) |
| Ex. (44) | Com. (2-4) | 5.3 | 4.2 | 300.0 | 7.1 | 134.0 | (0.66, 0.32) |
| Ex. (45) | Com. (2-5) | 5.2 | 4.4 | 300.0 | 6.9 | 122.2 | (0.66, 0.33) |
| Ex. (46) | Com. (2-6) | 5.2 | 4.5 | 300.0 | 6.6 | 141.0 | (0.66, 0.32) |
| Ex. (47) | Com. (2-7) | 5.5 | 4.3 | 300.0 | 7.0 | 146.9 | (0.65, 0.32) |
| Ex. (48) | Com. (2-8) | 5.4 | 4.0 | 300.0 | 7.4 | 112.3 | (0.66, 0.32) |
| Ex. (49) | Com. (2-9) | 5.2 | 4.3 | 300.0 | 7.0 | 94.4 | (0.66, 0.33) |
| Ex. (50) | Com. (2-10) | 5.3 | 4.0 | 300.0 | 7.4 | 134.4 | (0.66, 0.32) |
| Ex. (51) | Com. (2-11) | 5.3 | 4.4 | 300.0 | 6.8 | 105.4 | (0.65, 0.32) |
| Ex. (52) | Com. (2-12) | 5.4 | 4.2 | 300.0 | 7.1 | 134.6 | (0.66, 0.32) |
| Ex. (53) | Com. (2-13) | 5.2 | 4.1 | 300.0 | 7.3 | 148.4 | (0.66, 0.32) |
| Ex. (54) | Com. (2-14) | 5.4 | 4.4 | 300.0 | 6.9 | 90.6 | (0.67, 0.32) |
| Ex. (55) | Com. (2-15) | 5.5 | 4.2 | 300.0 | 7.2 | 131.2 | (0.66, 0.32) |
| Ex. (56) | Com. (2-16) | 5.5 | 4.1 | 300.0 | 7.3 | 110.2 | (0.66, 0.33) |
| Ex. (57) | Com. (2-17) | 5.4 | 4.5 | 300.0 | 6.7 | 125.6 | (0.66, 0.32) |
| Ex. (58) | Com. (2-18) | 5.3 | 4.1 | 300.0 | 7.3 | 125.4 | (0.65, 0.32) |
| Ex. (59) | Com. (2-19) | 5.4 | 4.4 | 300.0 | 6.7 | 128.2 | (0.66, 0.32) |
| Ex. (60) | Com. (2-20) | 5.3 | 4.1 | 300.0 | 7.4 | 133.2 | (0.66, 0.33) |
| Ex. (61) | Com. (2-21) | 5.3 | 4.5 | 300.0 | 6.7 | 122.2 | (0.66, 0.32) |
| Ex. (62) | Com. (2-22) | 5.4 | 4.1 | 300.0 | 7.4 | 145.4 | (0.65, 0.32) |
| Ex. (63) | Com. (2-23) | 5.2 | 4.2 | 300.0 | 7.1 | 148.7 | (0.66, 0.32) |
| Ex. (64) | Com. (2-24) | 5.3 | 4.0 | 300.0 | 7.4 | 96.3 | (0.66, 0.32) |
| Ex. (65) | Com. (2-25) | 5.6 | 4.8 | 300.0 | 6.2 | 97.9 | (0.66, 0.32) |
| Ex. (66) | Com. (2-26) | 5.7 | 4.6 | 300.0 | 6.5 | 121.3 | (0.65, 0.32) |
| Ex. (67) | Com. (2-27) | 5.8 | 4.8 | 300.0 | 6.3 | 138.7 | (0.66, 0.32) |
| Ex. (68) | Com. (2-28) | 5.7 | 4.7 | 300.0 | 6.4 | 132.7 | (0.66, 0.33) |
| Ex. (69) | Com. (2-29) | 5.6 | 5.0 | 300.0 | 6.1 | 120.1 | (0.66, 0.32) |
| Ex. (70) | Com. (2-30) | 5.8 | 4.9 | 300.0 | 6.1 | 146.2 | (0.65, 0.32) |
| Ex. (71) | Com. (2-31) | 5.7 | 4.8 | 300.0 | 6.2 | 142.6 | (0.66, 0.32) |
| Ex. (72) | Com. (2-32) | 5.7 | 4.8 | 300.0 | 6.3 | 112.6 | (0.66, 0.32) |
| Ex. (73) | Com. (2-33) | 5.8 | 4.7 | 300.0 | 6.4 | 113.6 | (0.67, 0.32) |
| Ex. (74) | Com. (2-34) | 5.6 | 4.9 | 300.0 | 6.1 | 113.3 | (0.66, 0.32) |
| Ex. (75) | Com. (2-35) | 5.7 | 4.7 | 300.0 | 6.3 | 112.3 | (0.66, 0.33) |
| Ex. (76) | Com. (2-36) | 5.7 | 4.9 | 300.0 | 6.2 | 103.3 | (0.66, 0.32) |
| Ex. (77) | Com. (2-37) | 5.7 | 4.8 | 300.0 | 6.3 | 140.7 | (0.65, 0.32) |
| Ex. (78) | Com. (2-38) | 5.7 | 4.8 | 300.0 | 6.3 | 145.7 | (0.66, 0.32) |
| Ex. (79) | Com. (2-39) | 5.7 | 4.9 | 300.0 | 6.1 | 129.2 | (0.66, 0.33) |
| Ex. (80) | Com. (2-40) | 5.7 | 4.9 | 300.0 | 6.1 | 111.1 | (0.66, 0.32) |
| Ex. (81) | Com. (2-41) | 5.6 | 4.7 | 300.0 | 6.4 | 111.4 | (0.65, 0.32) |
| Ex. (82) | Com. (2-42) | 5.6 | 4.9 | 300.0 | 6.2 | 130.5 | (0.66, 0.32) |
| Ex. (83) | Com. (2-43) | 5.6 | 4.7 | 300.0 | 6.4 | 128.7 | (0.66, 0.32) |
| Ex. (84) | Com. (2-44) | 5.7 | 4.8 | 300.0 | 6.3 | 124.0 | (0.66, 0.32) |
| Ex. (85) | Com. (2-45) | 5.6 | 4.8 | 300.0 | 6.3 | 112.2 | (0.67, 0.32) |
| Ex. (86) | Com. (2-46) | 5.8 | 4.9 | 300.0 | 6.1 | 136.5 | (0.66, 0.32) |
| Ex. (87) | Com. (2-47) | 5.8 | 4.8 | 300.0 | 6.3 | 120.0 | (0.66, 0.33) |
| Ex. (88) | Com. (2-48) | 5.7 | 4.7 | 300.0 | 6.4 | 109.0 | (0.66, 0.32) |

As shown in the Table 5 above, the OLEDs using the materials for OLEDs of the present invention as red light emitting layer materials were found to be high luminous efficiency, and to be significantly improved in life span and color purity.

In particular, the Comparative compounds 2 and 3 comprising 5-membered heterocyclic ring and 5-ring fused heterocyclic ring as a core, were shown much better results than the comparative compound 1, CBP, that is a type of biscarbazole. And the compounds of the present invention comprising 6-ring fused heterocyclic ring substituted by quinazoline derivatives and fused one more benzene ring were shown the best result as a red host. And the reason may be the same the results as explained in the green light emitting layer.

It is obvious that even when the inventive compounds are used in other organic material layers of an OLED, for example, a hole injection layer, a hole transport layer, an electron injection layer, an electron transport layer, the same effects can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

[Formula 1]

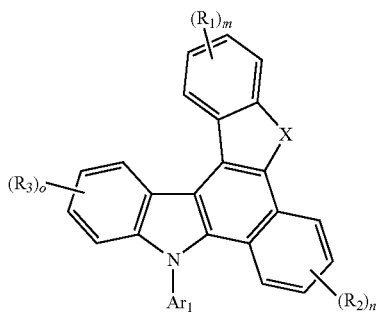

wherein, m, n and o are each an integer from 1 to 4, $R_1$ to $R_3$ are independently selected from the group consisting of hydrogen, deuterium, tritium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a fluorenyl group, -$L_1$—N($Ar_2$)($Ar_3$), and any two adjacent groups of $R_1$ to $R_3$ are optionally linked together to form at least one fused ring, with the proviso that, $R_1$ to $R_3$ that don't form a fused ring are as defined above, X is $NR_4$ or O (oxygen), herein, $R_4$ is selected from the group consisting of a $C_6$-$C_{60}$ aryl group, a $C_2$-$C_{60}$ heterocyclic group containing at least one heteroatom selected from the group consisting of O, N, S, Si, and P, $C_1$-$C_{50}$ alkyl group, a fluorenyl group, and -$L_1$—N($Ar_2$)($Ar_3$), $Ar_1$ is selected from the group consisting of a $C_6$-$C_{60}$ aryl group, a $C_2$-$C_{60}$ heterocyclic group containing at least one heteroatom selected from the group consisting of O, N, S, Si, and P, $C_1$-$C_{50}$ alkyl group, a fluorenyl group, and -$L_1$—N($Ar_2$)($Ar_3$), $Ar_2$ and $Ar_3$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, and a fluorenyl group, $L_1$ is selected from the group consisting of a single bond, a $C_6$-$C_{60}$ arylene group, a $C_2$-$C_{60}$ heteroarylene group containing at least one heteroatom selected from O, N, S, Si, and P, and a fluorenylene group, with the proviso that, the arylene group, heterocyclic group, and fluorenylene group may be respectively substituted by one or more substituents selected from the group consisting of a nitro group, a cyano group, a halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group and an amino group, and with the proviso that, the aryl group, fluorenyl group, heterocyclic group and alkyl group may be respectively substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

2. The compound as claimed in claim 1, wherein the compound is represented by one of Formulas below:

[Formula 2]

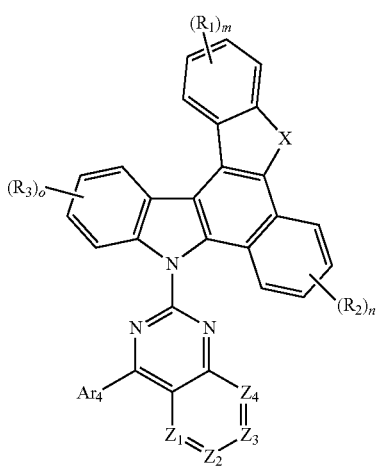

[Formula 3]

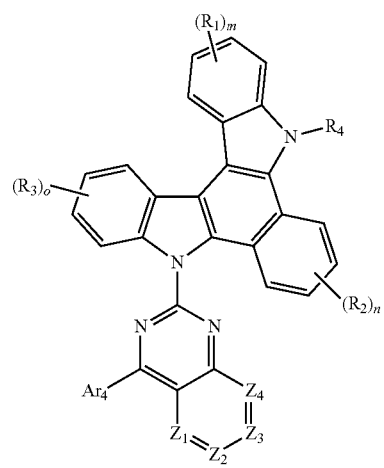

[Formula 4]

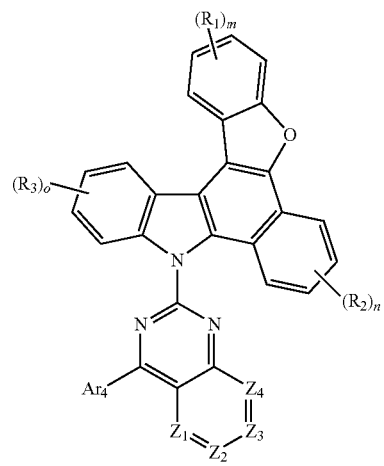

in Formulas 2 to 4, $R_1$ to $R_4$, X, m, n and o are as defined in claim 1, $Ar_4$ is selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group and a fluorenyl group, and $Z_1$ to $Z_4$ are independently $CR_5$ or N, here, $R_5$ may be selected from the group consisting of hydrogen, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, and a fluorenyl group.

3. The compound as claimed in claim 1, being any one of the compounds below:

1-1
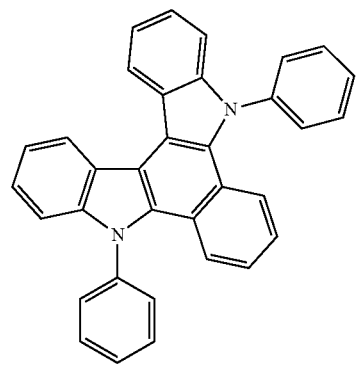

1-2
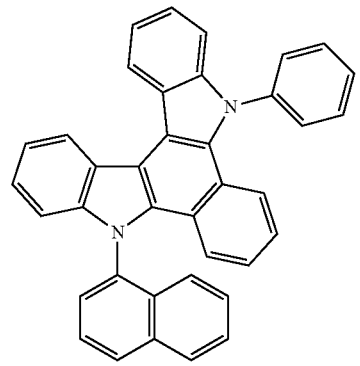

1-3
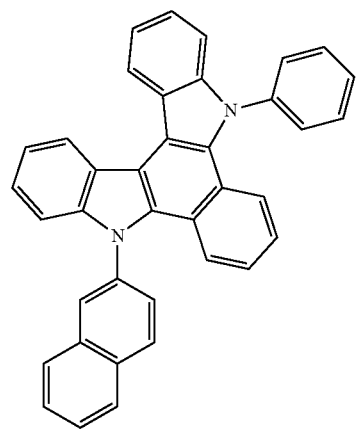

1-4
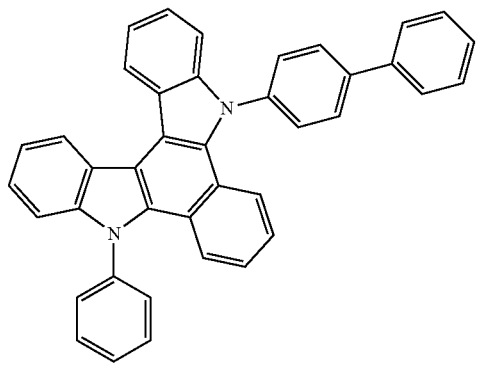

1-5
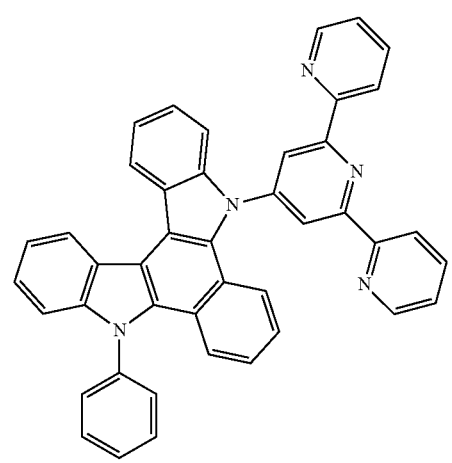

1-6
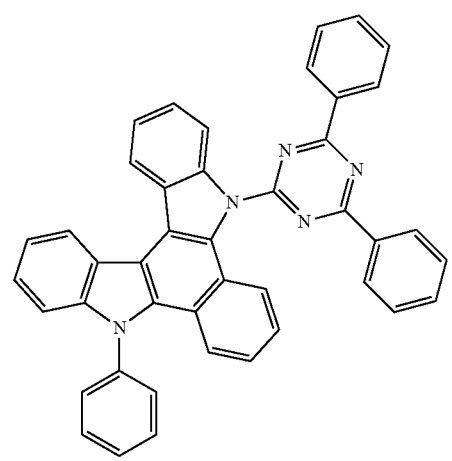

-continued
1-7
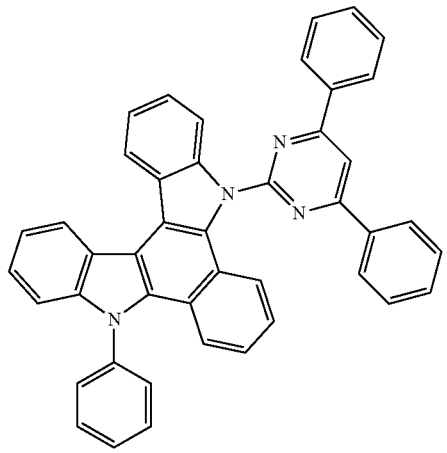
1-8
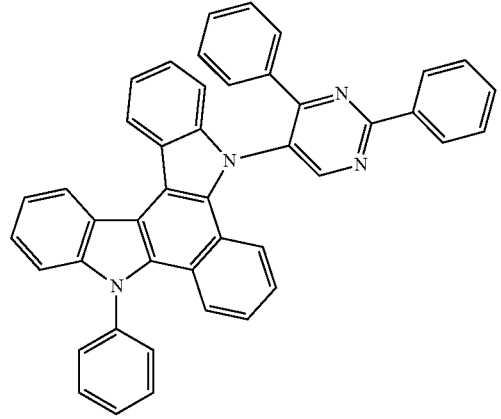
1-9
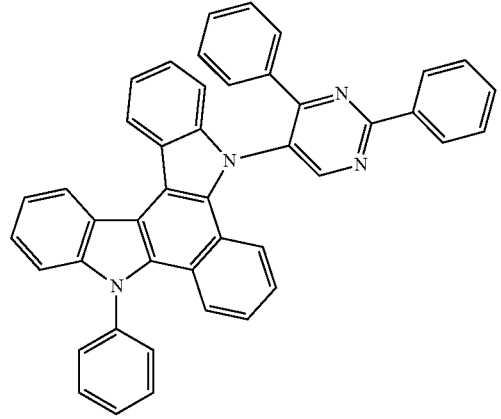
-continued
1-10
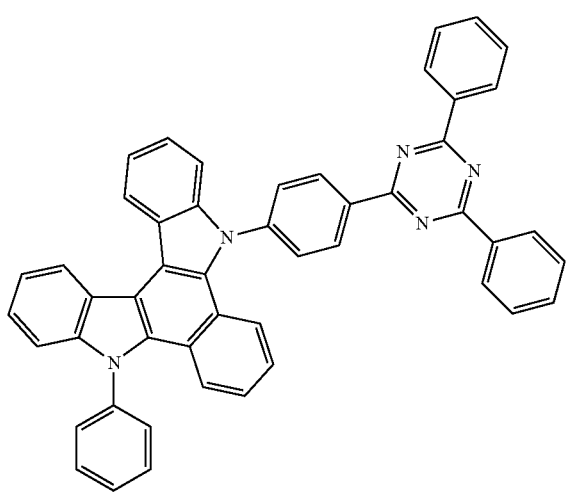
1-11
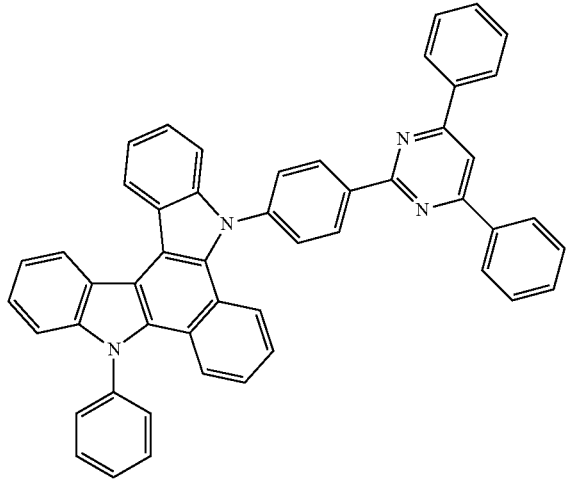
1-12
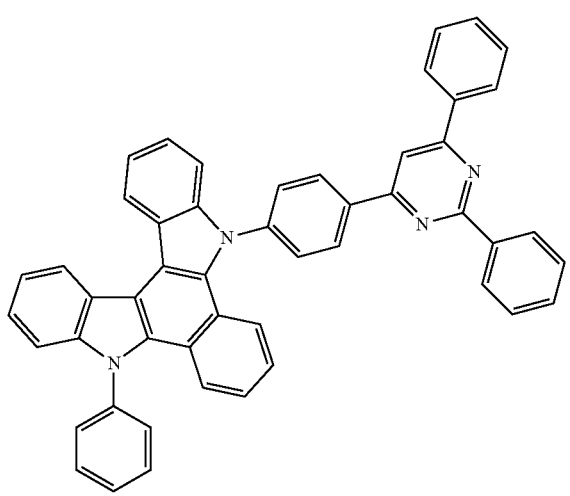

-continued
1-13
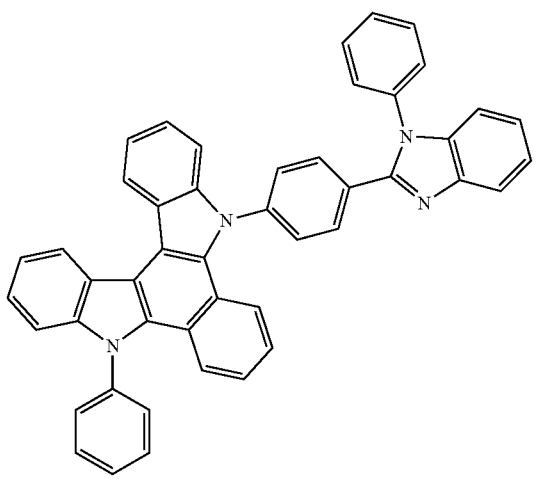
1-14
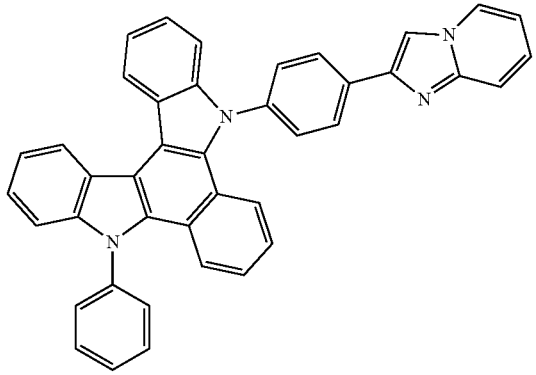
1-15
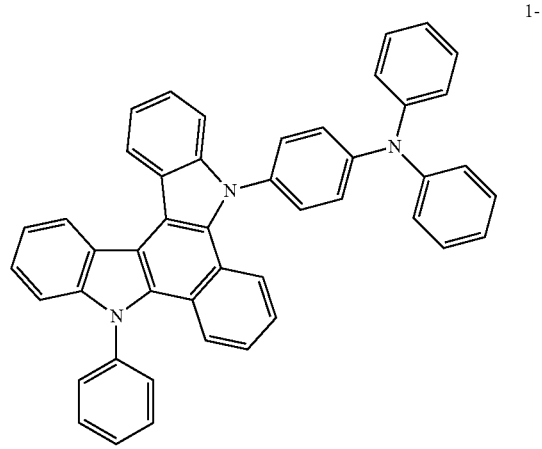
1-16
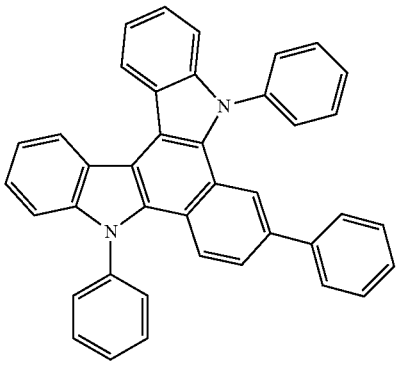
1-17
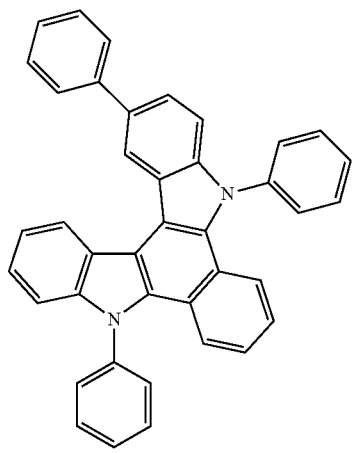
1-18

1-19
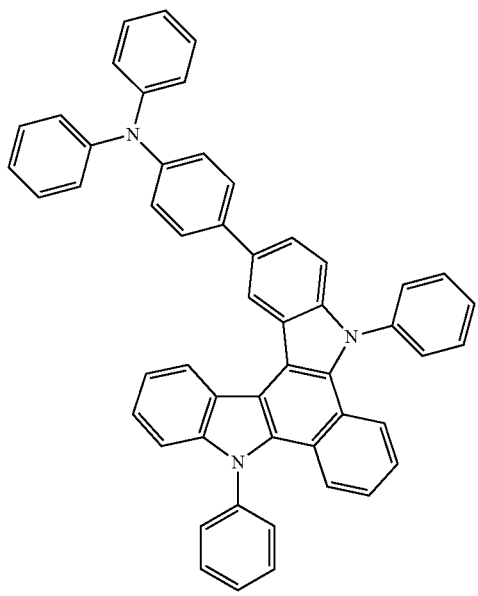
1-20
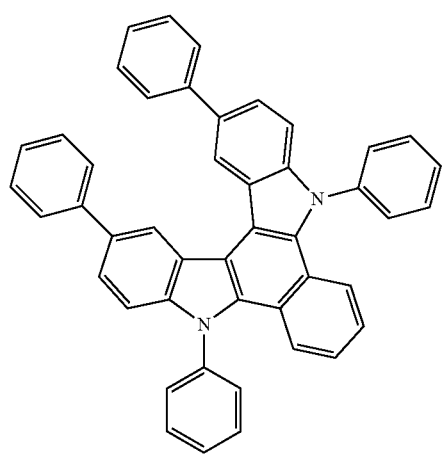
1-21
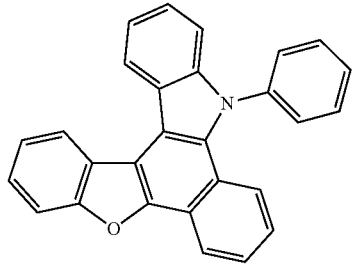
1-22
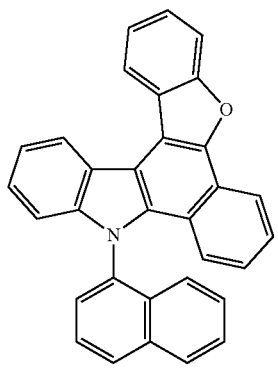
1-23
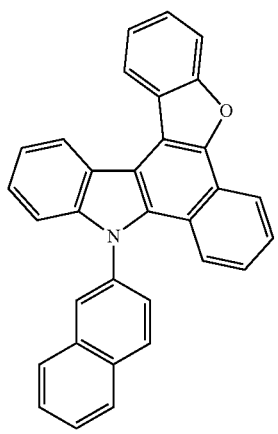
1-24
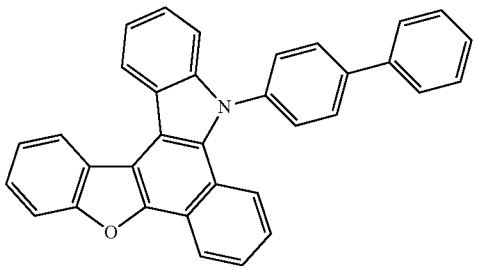
1-25
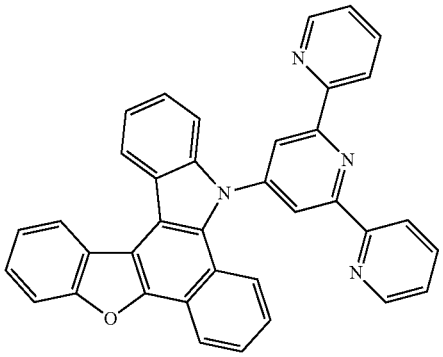

1-26
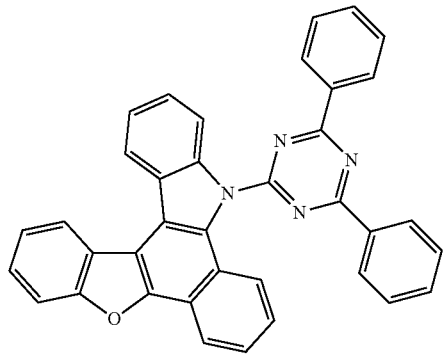
1-27
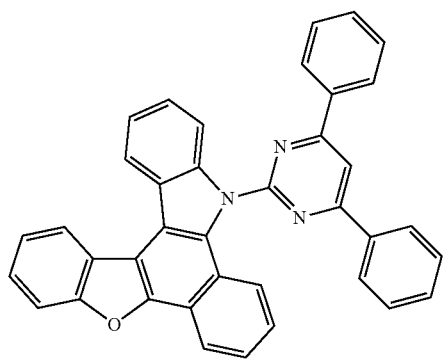
1-28
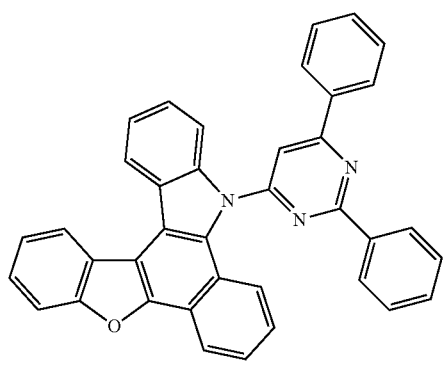
1-29
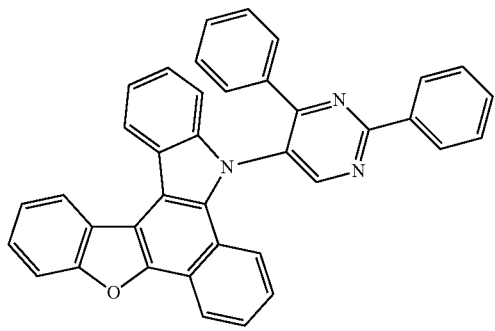
1-30
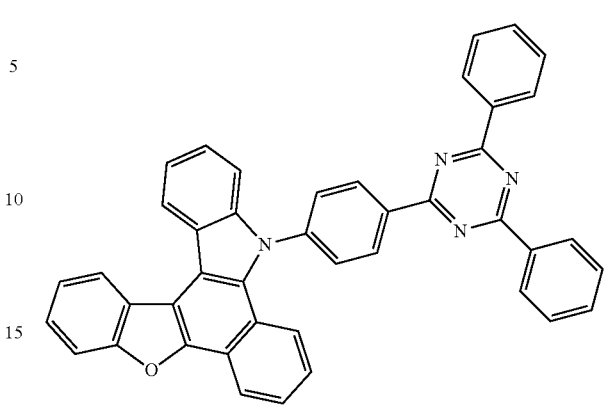
1-31
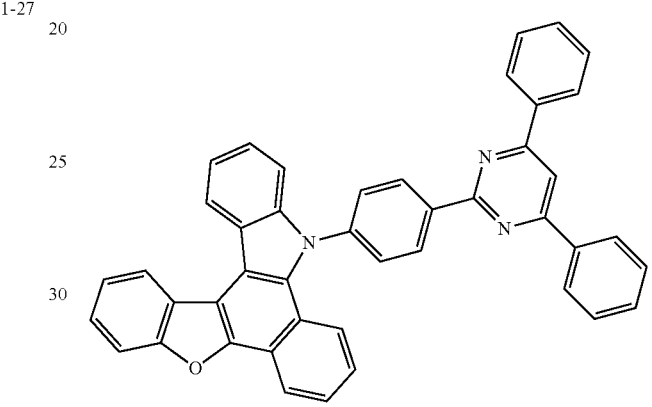
1-32
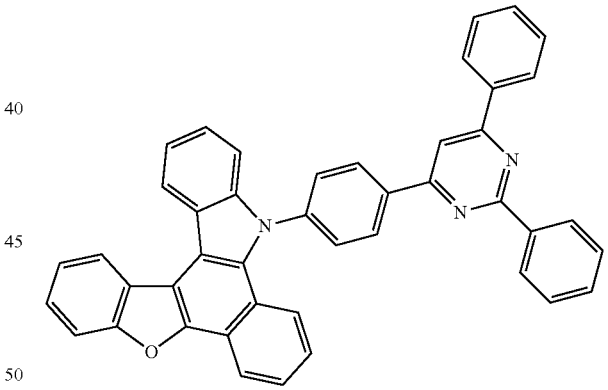
1-33
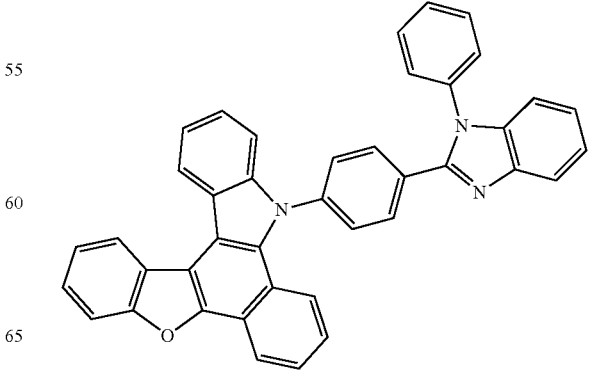

1-34
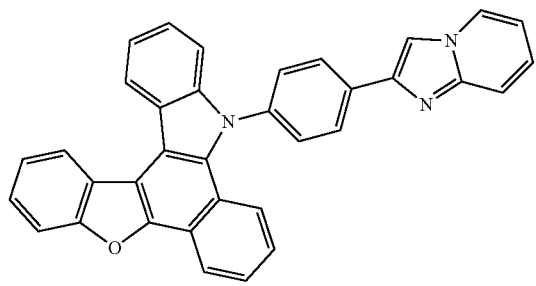
1-35
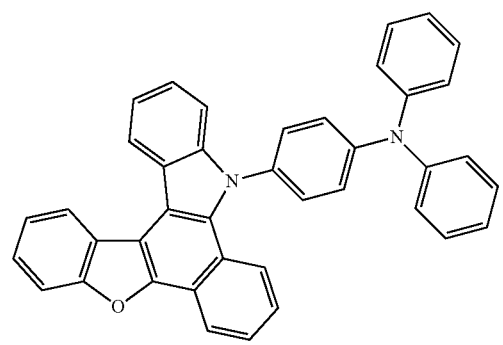
1-36
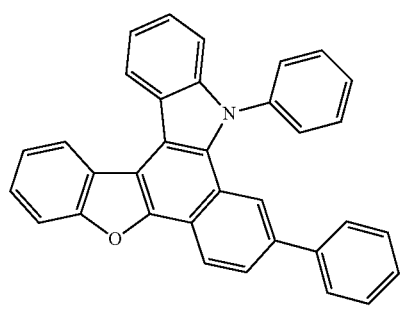
1-37
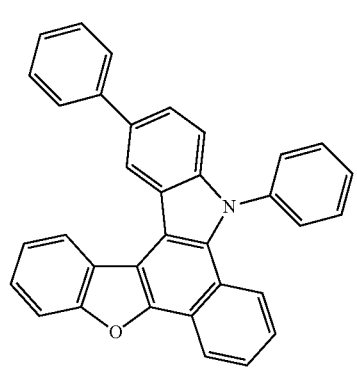
1-38
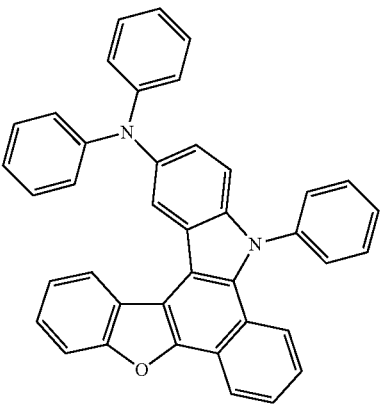
1-39
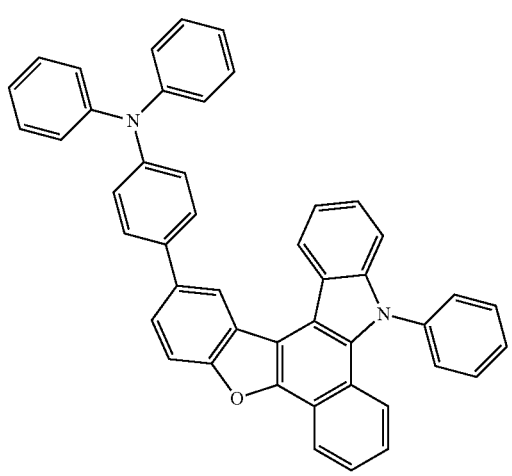
1-40
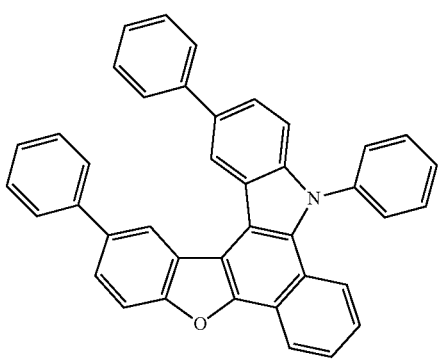
2-1
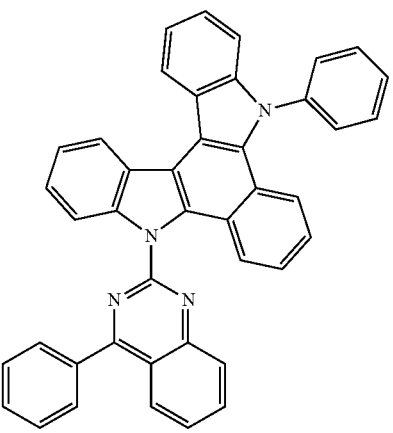

2-2
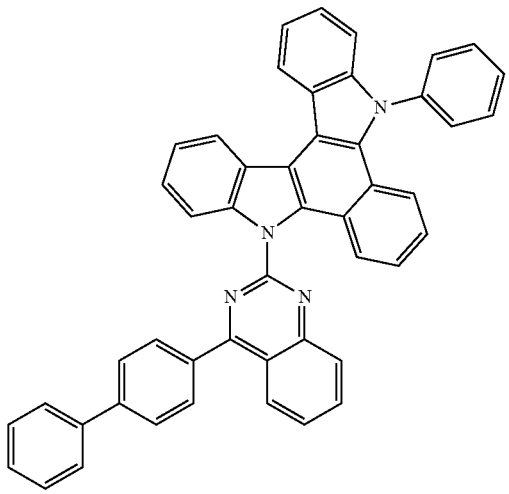
2-3
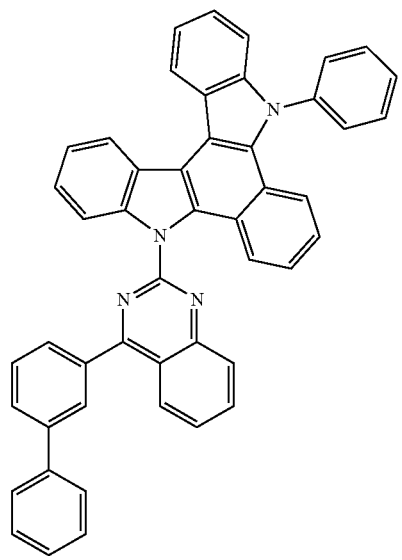
2-4
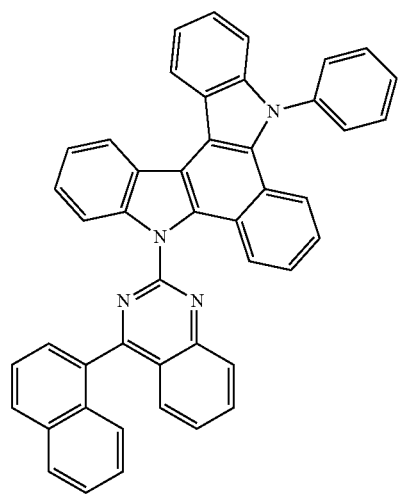
2-5
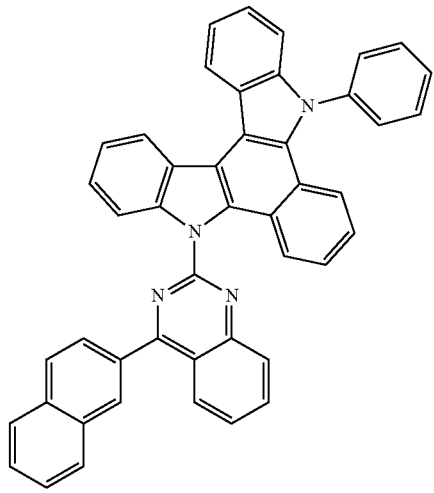
2-6
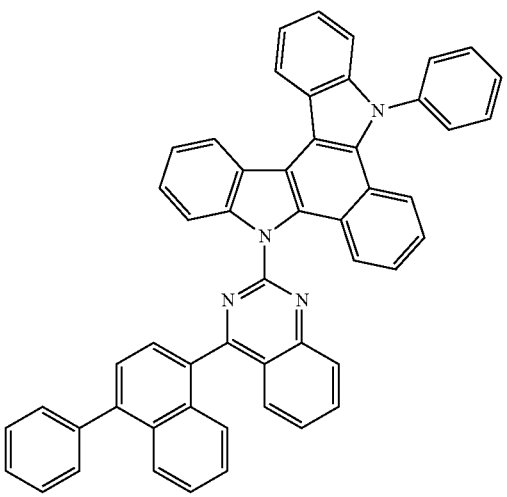
2-7
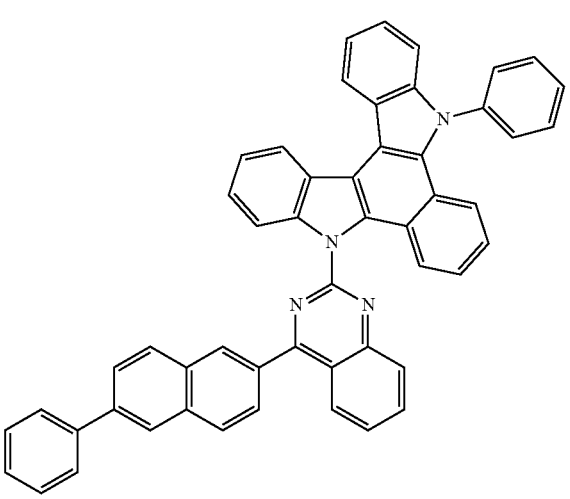

2-8
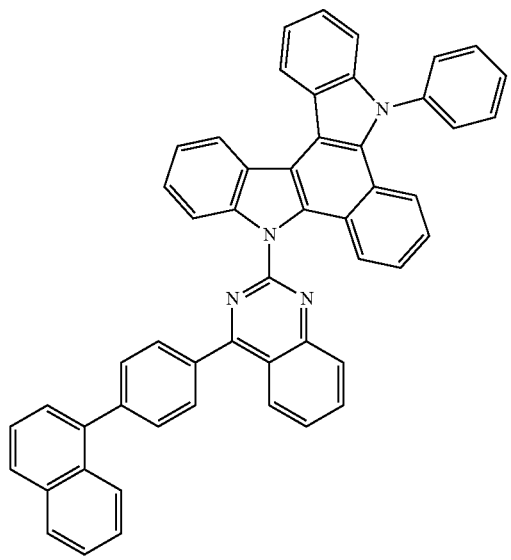
2-11
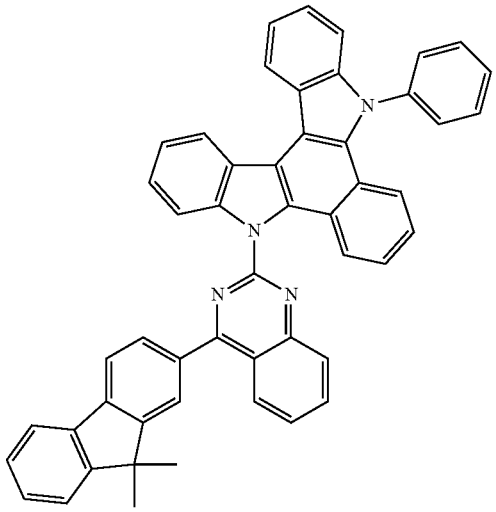
2-9
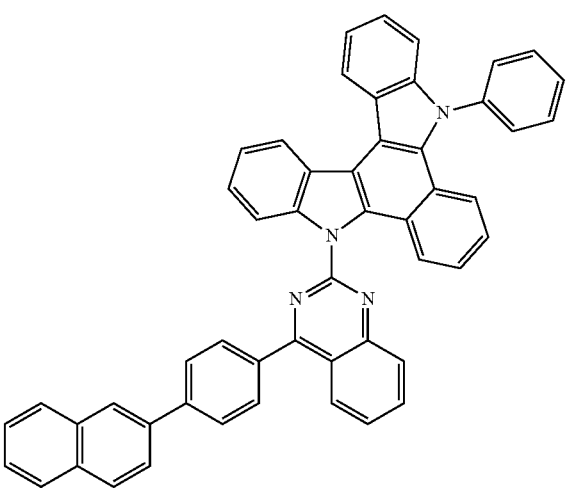
2-12
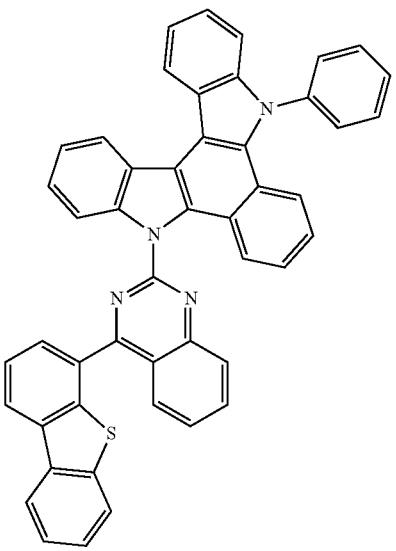
2-10
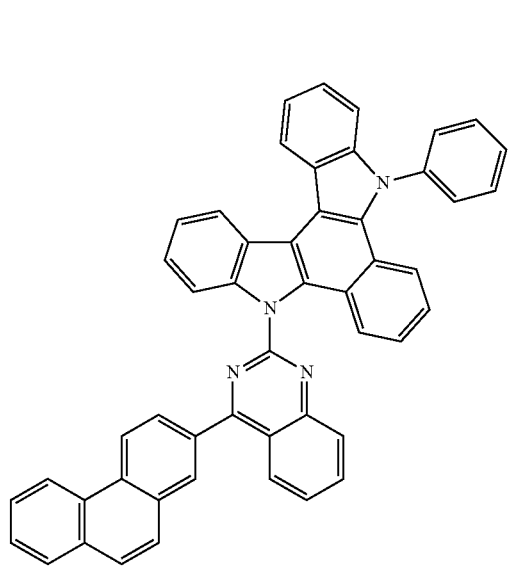
2-13
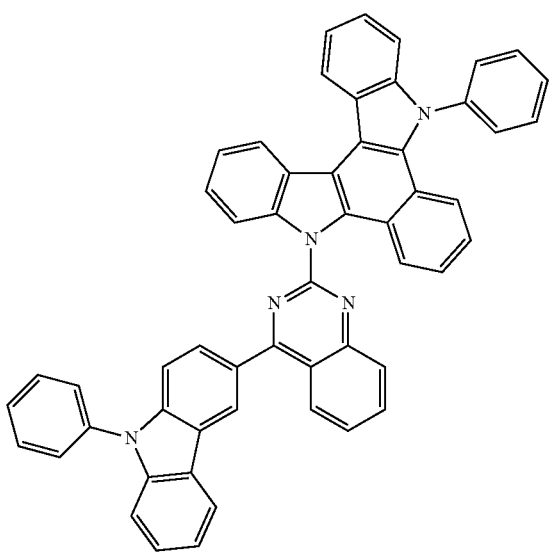

2-14
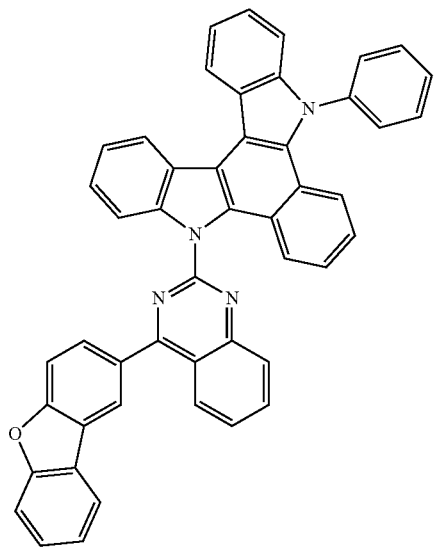
2-17
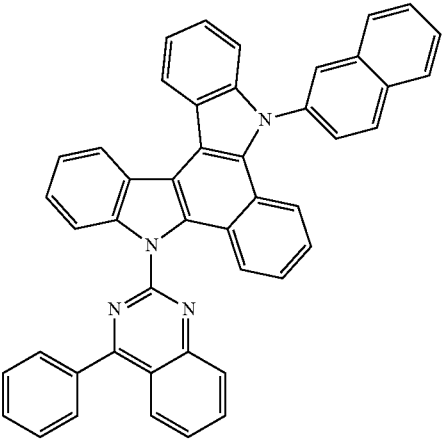
2-15
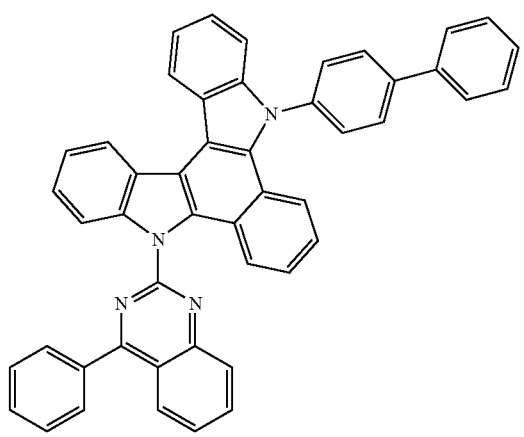
2-18
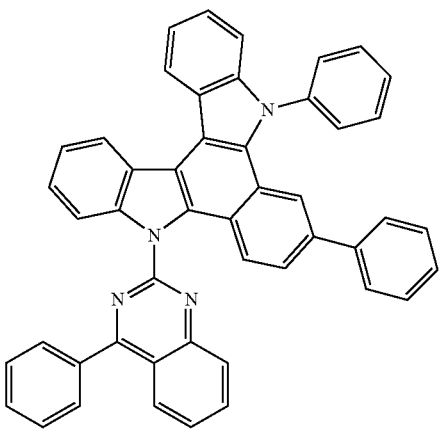
2-16
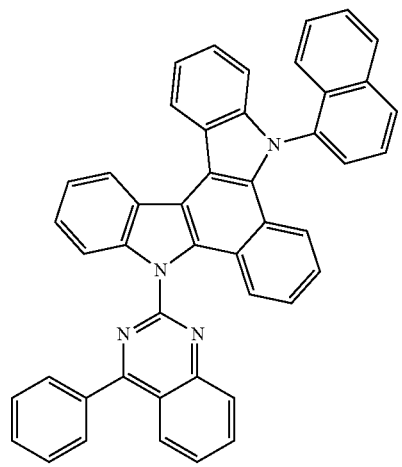
2-19
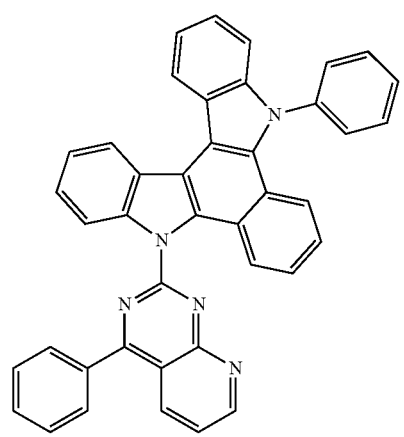

-continued
2-20
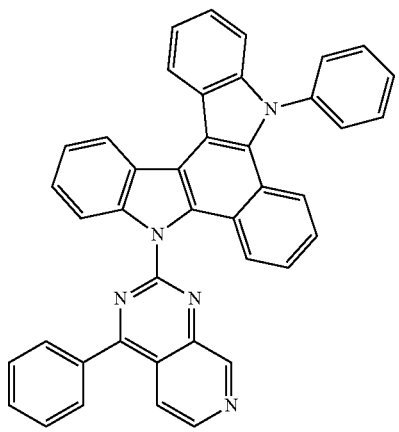
2-21
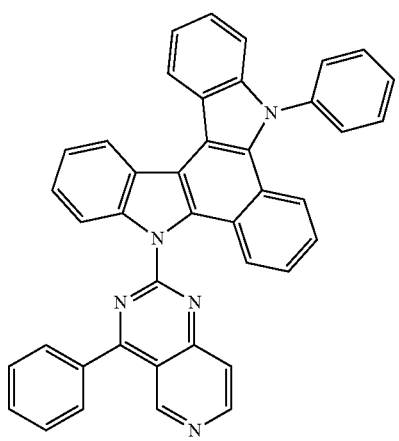
2-22
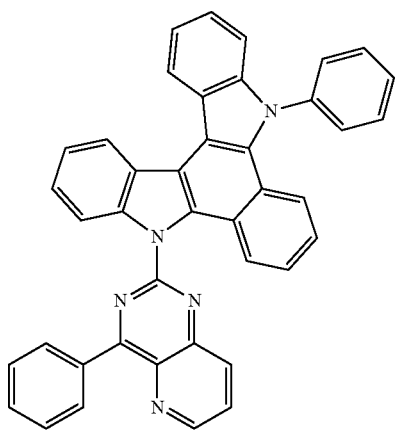
-continued
2-23
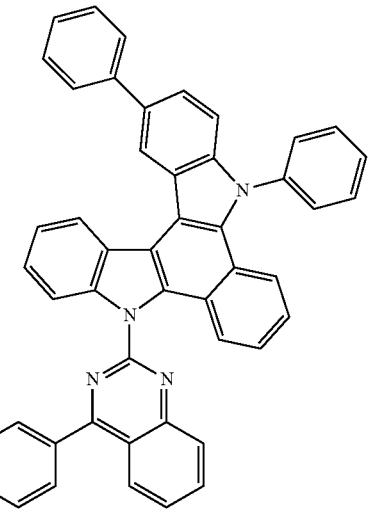
2-24
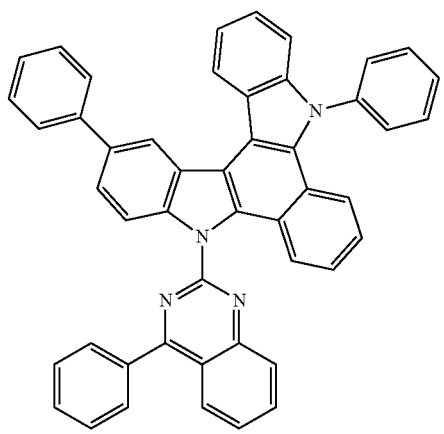
2-25
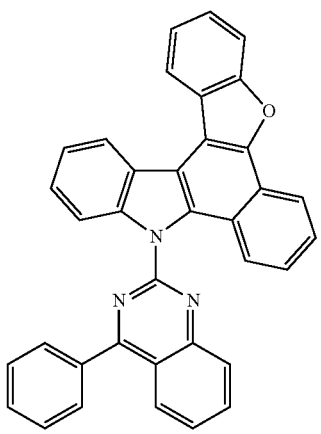

-continued
2-26
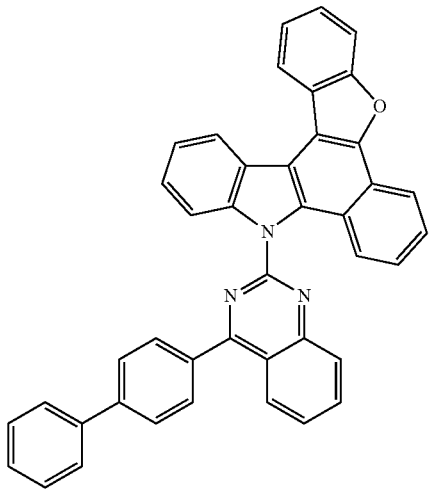
2-27
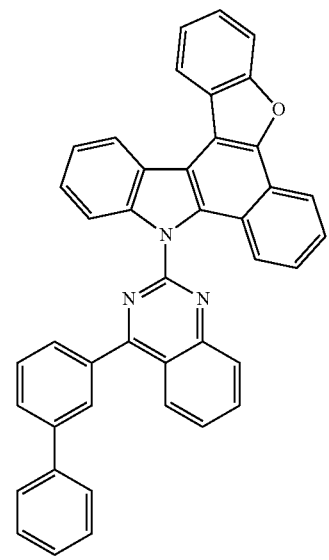
2-28
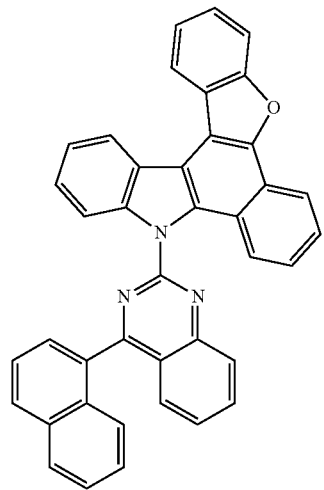
-continued
2-29
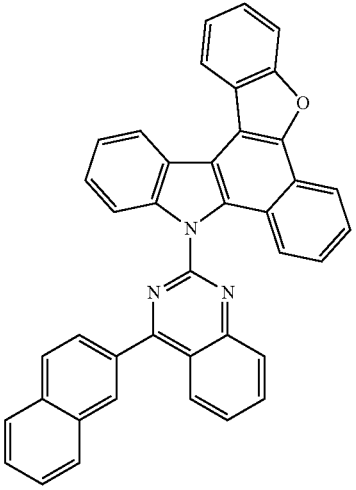
2-30
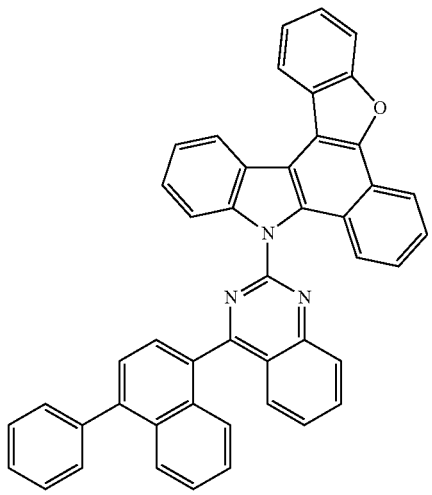
2-31
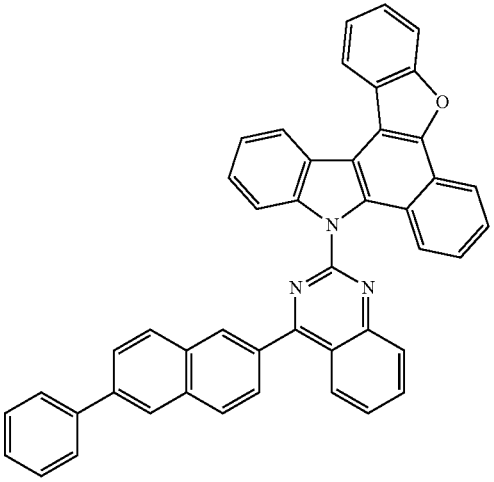

-continued
2-32
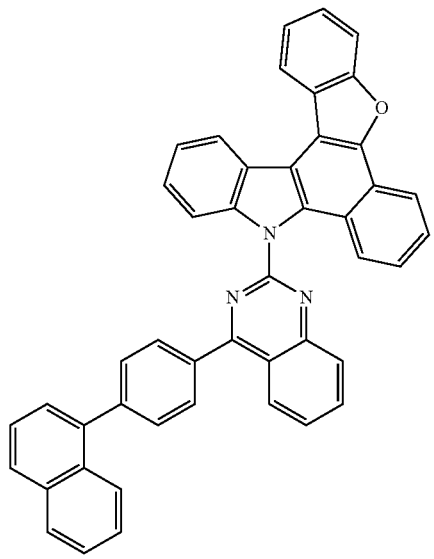
2-33
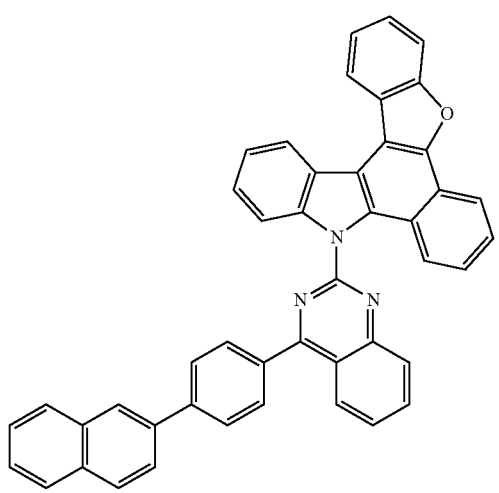
2-34
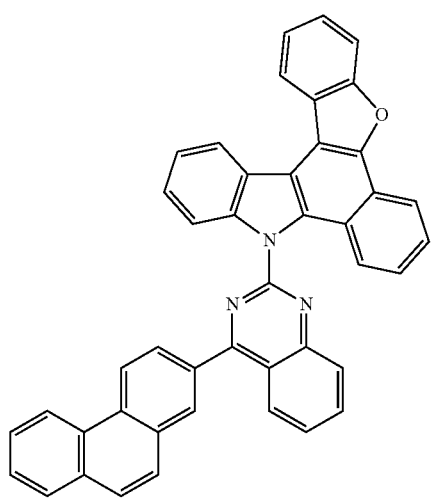
-continued
2-35
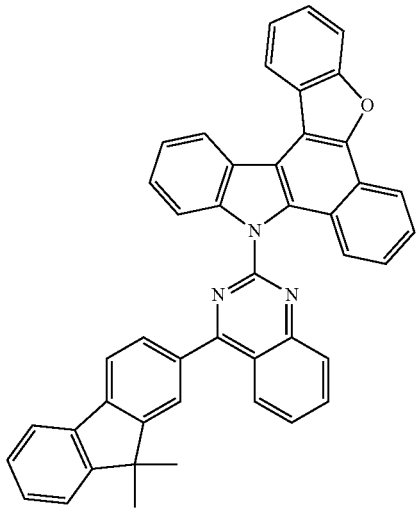
2-36
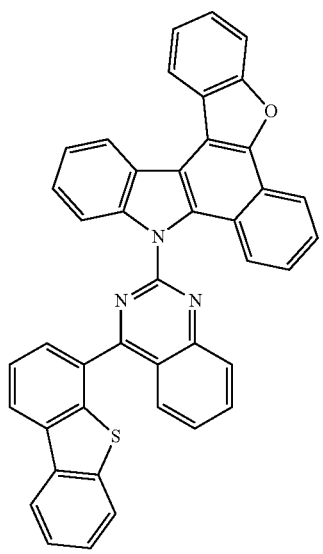
2-37
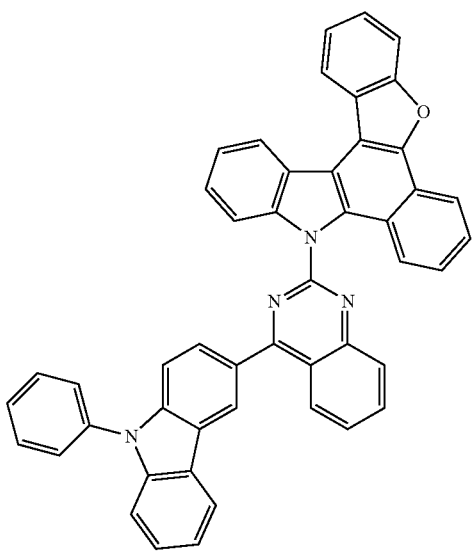

2-38
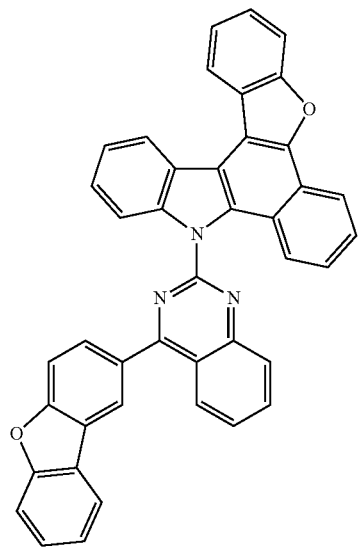
2-39
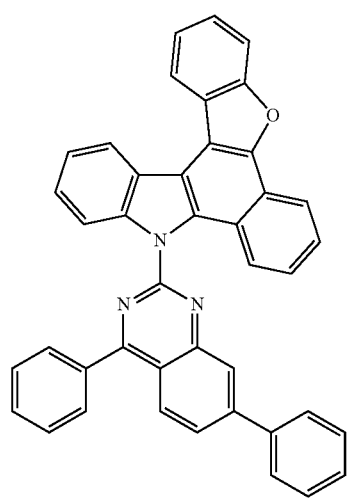
2-40
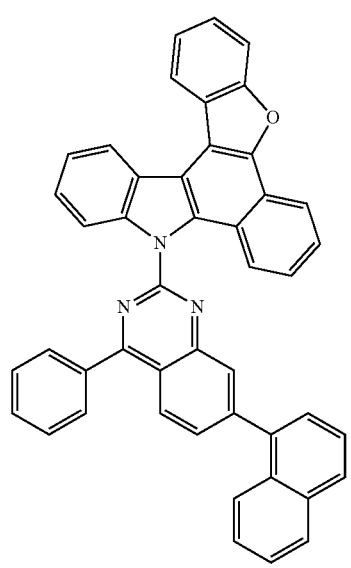
2-41
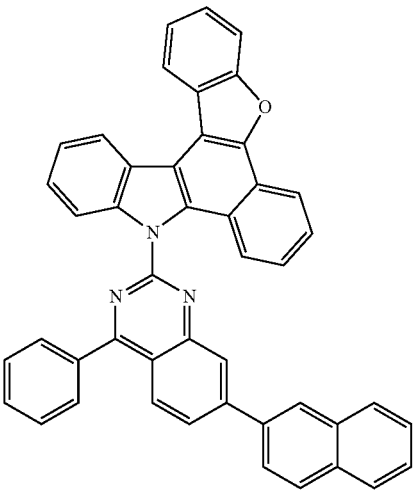
2-42
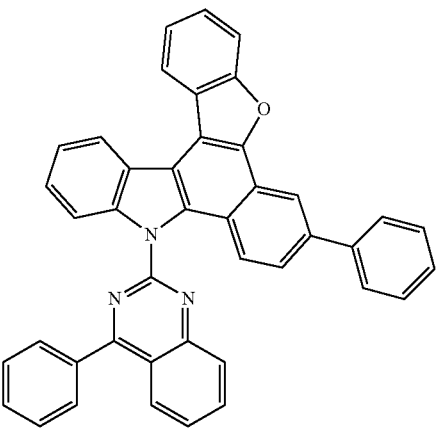
2-43
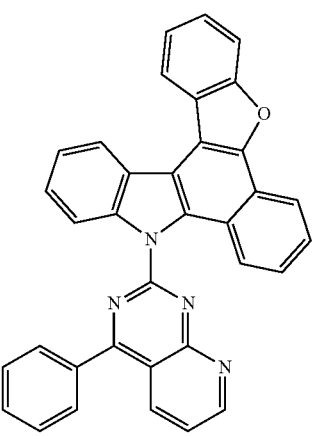

-continued 2-44
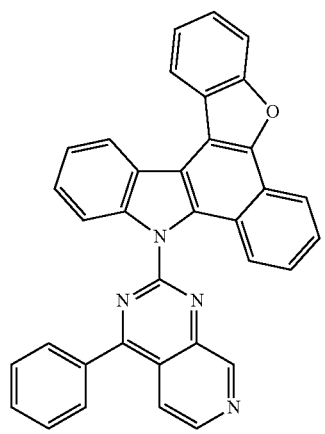

2-45
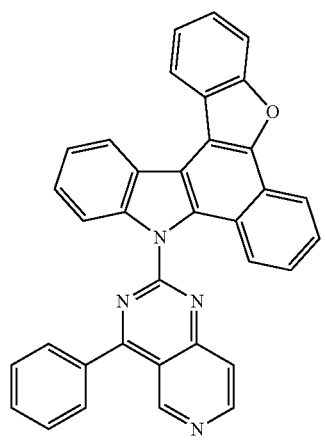

2-46
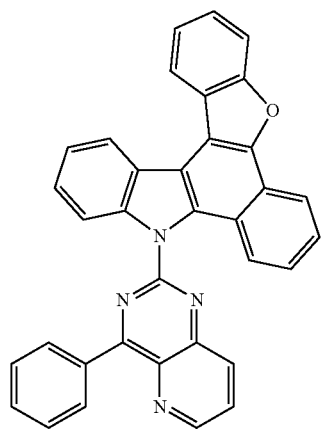

-continued 2-47
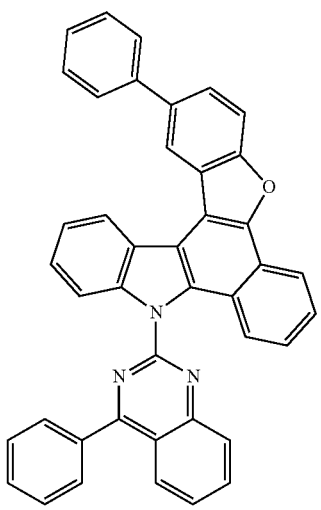

2-48
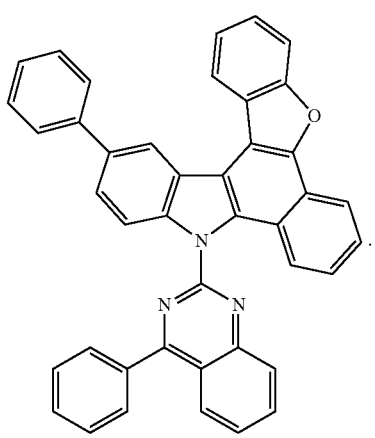

4. An organic electric element comprising a first electrode, a second electrode, and an organic material layer disposed between the first electrode and the second electrode, wherein the organic material layer comprises the compound as claimed in claim 1.

5. The organic electric element as claimed in claim 4, wherein the organic material layer is formed by a soluble process.

6. The organic electric element as claimed in claim 4, wherein the organic material layer comprises a light emitting layer, and the compound is used as a host material of the light emitting layer.

7. An electronic device comprising a display device, which comprises the organic electric element as claimed in claim 4, and a control unit for driving the display device.

8. The electronic device as claimed in claim 7, wherein the organic electric element comprises at least one of an organic light emitting diode, an organic solar cell, an organic photo conductor, an organic transistor, and an element for monochromatic or white illumination.

* * * * *